(12) United States Patent
Sachs et al.

(10) Patent No.: US 8,087,938 B2
(45) Date of Patent: Jan. 3, 2012

(54) COMPUTER SYSTEM AND METHOD FOR TRAINING CERTIFYING OR MONITORING HUMAN CLINICAL RATERS

(75) Inventors: Gary Steven Sachs, Lincoln, MA (US); Roy Howard Perlis, Cambridge, MA (US); Daniel V. DeBonis, II, Boston, MA (US)

(73) Assignee: USC Specialty Clinical Services, LLC, Wayne, PA (US)

( * ) Notice: Subject to any disclaimer, the term of this patent is extended or adjusted under 35 U.S.C. 154(b) by 1039 days.

(21) Appl. No.: 11/966,439

(22) Filed: Dec. 28, 2007

(65) Prior Publication Data

US 2008/0312958 A1 Dec. 18, 2008

Related U.S. Application Data

(63) Continuation of application No. 10/282,215, filed on Oct. 28, 2002, now Pat. No. 7,315,725.

(60) Provisional application No. 60/340,113, filed on Oct. 26, 2001.

(51) Int. Cl.
 *G09B 7/00* (2006.01)
(52) U.S. Cl. ....................................................... 434/323
(58) Field of Classification Search .......... 434/322–323, 434/350, 354; 705/2
 See application file for complete search history.

(56) References Cited

U.S. PATENT DOCUMENTS

| | | | |
|---|---|---|---|
| 5,471,382 A * | 11/1995 | Tallman et al. | ............... 600/300 |
| 5,473,537 A | 12/1995 | Glazer et al. | |
| 5,553,609 A | 9/1996 | Chen et al. | |
| 5,764,923 A | 6/1998 | Tallman et al. | |
| 6,071,236 A | 6/2000 | Iliff | |
| 6,081,786 A | 6/2000 | Barry et al. | |
| 6,120,440 A | 9/2000 | Goknar | |
| 6,126,596 A | 10/2000 | Freedman | |
| 6,234,964 B1 | 5/2001 | Iliff | |
| 6,246,975 B1 | 6/2001 | Rivonelli et al. | |
| 6,289,353 B1 | 9/2001 | Hazlehurst et al. | |
| 6,524,241 B2 | 2/2003 | Iliff | |
| 6,546,230 B1 | 4/2003 | Allison | |
| 6,817,980 B2 | 11/2004 | Iliff | |
| 2002/0032581 A1 | 3/2002 | Reitberg | |
| 2002/0077853 A1 | 6/2002 | Boru et al. | |
| 2002/0095313 A1 | 7/2002 | Haq | |
| 2002/0192159 A1 | 12/2002 | Reitberg | |

OTHER PUBLICATIONS

Anderson, D.L., "Development of an Instrument to Measure Pain in Rheumatoid Arthritis: Rheumatoid Arthritis Pain Scale (RAPS)," Arthritis Care and Research, 45:317-323 (2001).
Bardwell et al., "Rheumatoid Arthritis Severity Scale: a brief, physician-completed scale not confounded by patient self-report of psychological functioning," Rheumatology, 41:38-45 (2002).

(Continued)

*Primary Examiner* — Xuan Thai
*Assistant Examiner* — Evan Page
(74) *Attorney, Agent, or Firm* — Woodcock Washburn LLP

(57) ABSTRACT

A method and system are disclosed for computerized training, monitoring, certification or re-certification of human raters in clinical trials. The invention provides an interactive computerized interview that can be compared scores obtained by human raters to monitor and train clinical raters on a continuing basis in order to reduce rater drift and variance during clinical trials. Remediation can be automatically flagged or provided to improve a deviating rater's performance. Computerized assessment of symptom severity is provided without the need for human clinical raters. The system and method enable screening of prospective patients for inclusion or exclusion from a clinical trial by automatically obtaining computerized ratings of symptom severity.

32 Claims, 42 Drawing Sheets

OTHER PUBLICATIONS

Brown et al., "Placebo Response in Depression: A Search for Predictors," Psychiatry Research, 26:259-264 (1988).
Christo et al., "Validation of the Christo Inventory for Substance-misuse Services (CISS): a simple outcome evaluation tool,," Drug and Alcohol Dependence, 59:189-197 (2000).
Crippa et al., "A structured interview guide increases Brief Psychiatric Rating Scale reliability in raters with low clinical experience," Acta Psychiatricia Scan., 103:465-470 (2001).
Devins et al., "Structure of Lifestyle Disruptions in Chronic Disease," Medical Care, 39(10):1097-1104 (2001).
Duffy et al., "The Utility of the Arthritis Impact Measurement Scales for Patients with Psoriatic Arthritis," Journal of Rheumatology, 19(11):1727-1732 (1992).
Folstein et al., "'Mini-Mental State', A Practical Method for Grading the Cognitive State of Patients for the Clinician," J. Psychiat. Res., 12:189-198 (1975).
Heinik et al., "Comparison of a Clock Drawing Test in Elderly Schizophrenia and Alzheimer's Disease Patients: A Preliminary Study," International Journal of Geriatric Psychiatry, 15:638-643 (2000).
Keck et al., "Placebo Effect in Randomized, Controlled Maintenance Studies of Patients with Bipolar Disorder," Biol. Psychiatry, 47:756-761 (2000).
Keck et al., "Placebo Effect in Randomized, Controlled Studies of Acute Bipolar Mania and Depression," Biol. Psychiatry, 47:748-755 (2000).
Leon et al., "More Reliable Outcome Measures Can Reduce Sample Size Requirements," Arch. Gen. Psychiatry, 52:867-871 (1995).
Lerner et al., "The Work Limitations Questionnaire's validity and reliability among patients with osteoarthritis," Journal of Clinical Epidemiology, 35:197-208 (2002).
Lopez-Navidad, A., "Chronic "brain death": meta-analysis and conceptual consequences," Neurology, 53:1369 (1999).
Maj et al., "Reliability and validity of the DSM-IV diagnostic category of schizoaffective disorder: Preliminary data," Journal of Affective Disorders, 57:95-98 (2000).
Meadows et al., "Assessing perceived need for mental health care in a community survey: development of the Perceived Need for Care Questionnaire (PNCQ)," Psychiatry Psychiatr. Epidomeiol., 35:427-435 (2000).
Meenan et al., "The Content and Properties of a Revised and Expanded Arthritis Impact Measurement Scales Health Status Questionnaire," Arthritis & Rheumatism, 35:1-10 (1992).
Meyer et al., "Validating mini-mental status, cognitive capacity screening and Hamilton depression scales utilizing subjects with vascular headaches," International Journal of Geriatric Psychiatry, 16:430-435 (2001).
Mino et al., "Evaluation of expressed emotion (EE) status in mood disorders in Japan: inter-rater reliability and characteristics of EE," Psychiatry Research, 94:221-227 (2000).
Montgomery & Asberg, "A New Depression Scale Designed to be Sensitive to Change," Brit. J. Psychiatry, 134:382-389 (1979).
Muller et al., "Evaluation of standardized rater training for the Positive and Negative Syndrome Scale (PANSS)," Schizophrenia Research, 32:151-160 (1998).
Muller et al., "Improvement of inter-rater reliability of PANSS items and subscales by a standardized rater training," Acta. Psychiatrica Scand., 98:135-139 (1998).
Mulsant et al., "Interrater Reliability in Clinical Trials of Depressive Disorders," Am J. Psychiatry, 159(9):1598-1600 (2002).
Perkins et al., "Penny-Wise and Pound-Foolish: The Impact of Measurement Error on Sample Size Requirements in Clinical Trials," Biol. Psychiatry, 47:762-766 (2000).
Quitkin et al., "Validity of Clinical Trials of Antidepressants," Am. J. Psychiatry, 157:327-337 (2000).
Quitkin, F.M., "Placebos, Drug Effects, and Study Design: A Clinician's Guide," Am. J. Psychiatry, 156(6):829-836 (1999).
Rigby et al., "Quality of life assessment in MND: development of a Social Withdrawal Scale," Journal of Neurological Sciences, 169:26-34 (1999).
Robinson et al., "Concerns About Clinical Drug Trials," Journal of Clinical Psychopharmacology, 20(6):593-596 (2000).
Rock et al., "HoNOS:is there any point in training clinicians?," Journal of Psychiatric and Mental Health Nursing, 8:405-409 (2001).
Royall et al., "CLOX: an executive clock drawing task," Journal Neurosurg. Psychiatry, 64:588-594 (1998).
Salaffi et al., "Validation of an Italian version of the Arthritis Impact Measurement Scales 2 (Italian-AIMS2) for patients with osteoarthritis of the knee," Rheumatology, 39:720-727 (2000).
Schatzberg et al., "Use of Placebo Control Groups in Evaluating Efficacy of Treatment of Unipolar Major Depression," Biol. Psychiatry, 47:736-744 (2000).
Scholte et al., "DSM-IV Related ADHD Symptom Ratings by Professional Caretakers in Residential Treatment Centres," J. Child Psychol. Psychiat., 42:341-346 (2001).
Schulman, K.I., "Clock-Drawing: Is it the Ideal Cognitive Screening Test?," Int. J. Geriat. Psychiatry, 15:548-561 (2000).
Shear et al., "Reliability and Validity of a Structured Interview Guide for the Hamilton Anxiety Rating Scale (SIGH-A)," Depression and Anxiety, 13:166-178 (2001).
Shiels et al., "The inter-rater reliability of a generic measure of severity of illness," Family Practice, 14(6)466-471 (1997).
Storey et al., "A comparison of five clock scoring methods using ROC (receiver operating characteristic) curve analysis," International Journal of Geriatric Psychiatry, 16:394-399 (2001).
Sulter et al., "Use of the Barthel Index and Modified Rankin Scale in Acute Stroke Trials," Stroke, 30:1538-1541 (1999).
Susser et al., "Reliability of the Life Chart Schedule for assessment of the long-term course of schizophrenia," Schizophrenia Research, 42:67-77 (2000).
Swann et al., "Mania: gender, transmitter function, and response to treatment," Psychiatry Research, 88:55-61 (1999).
Thase, M.E., "How Should Efficacy Be Evaluated in Randomized Clinical Trials of Treatments for Depression?," J. Clin. Psychiatry, 60(Suppl 4):23-31 (1999).
The European Agency for the Evaluation of Medicinal Products, EMEA, pp. 1/9-9/9 (2001).
The European Agency for the Evaluation of Medicinal Products, pp. 1/10-10/10 (1998).
Tohen et al., "Olanzapine versus haloperidol in schizoaffective disorder, bipolar type," Journal of Affective Disorders, 67:133-140 (2001).
Trivedi et al., "Does a Placebo Run-In or a Placebo Treatment Cell Affect the Efficacy of Antidepressant Medications?," Neuropsychopharmacology, 11(1):33-43 (1994).
Wade et al., "The Barthel ADL Index: a standard measure of physical disability," Int. Disabil. Stud., 10:64-67 (1998).
Ware et al., "The SF-36 Arthritis-Specific Health Index (ASHI)," Medical Care, 37(5):MS40-MS50 (1999).
Williams, J.B.W., "Standardizing the Hamilton Depression Rating Scale: past, present, and future," Eur. Arch. Psychiatry Clin. Neurosci., 251(Suppl. 2):11/6-11/12 (2001).
Yesavage et al., "Development and Validation of a Geriatric Depression Screening Scale: A Preliminary Report," J. Psychiat. Res., 17:37-49 (1983).
Young et al., "A Rating Scale for Mania: Reliability, Validity and Sensitivity," Brit. J. Psychiat., 133:429-435 (1978).

* cited by examiner

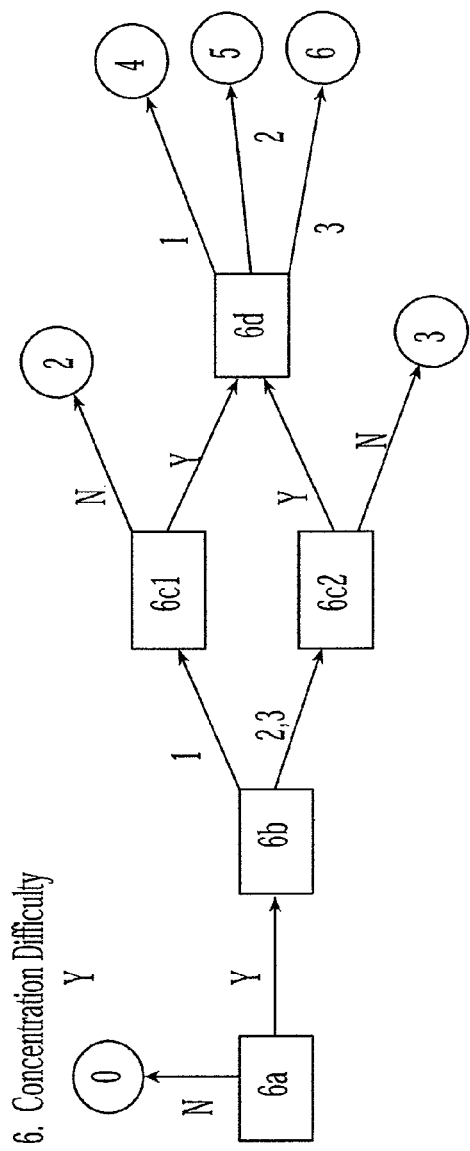

6. Concentration Difficulty

0 No difficulties concentration
2 Occasional difficulties in collecting one's thoughts
4 Difficulties in concentrating and sustaining thought which reduces the ability to read or hold a conversation
6 Unable to read or converse without great difficulty a. "Did you have any difficulty concentrating or collecting your thoughts this week?" (Y/N)
b. "How often was this a problem for you?" (occasionally=1, sometimes=2, often=3)
c. "Did this problem interfere with having conversations, or with reading? (Y/N)
d. "How much did this problem interfere with having conversations, or with reading?" (just a little=1, a fair amount=2, a great deal=3);

*Fig. 21*

13. Somatic Symptoms

COMPUTER SYSTEM AND METHOD FOR TRAINING CERTIFYING OR MONITORING HUMAN CLINICAL RATERS

CROSS-REFERENCE TO RELATED APPLICATIONS

This application is a continuation of U.S. application Ser. No. 10/282,215, filed Oct. 28, 2002, which claims the benefit under 35 U.S.C. §119(e) of U.S. Provisional Application No. 60/340,113, filed Oct. 26, 2001. The entire disclosures of each of these applications are hereby incorporated herein by reference.

FIELD OF THE INVENTION

The present invention relates to computerized systems and methods for training, monitoring, certifying or re-certifying human raters of clinical symptoms, to interactive computerized interviews with patients for measuring symptom severity, and to computerized systems and methods for using script-based interviews for clinical evaluation of patients.

BACKGROUND OF THE INVENTION

The failure of clinical trials to detect significant differences in efficacy between treatment groups is a well-recognized and increasingly costly impediment to clinical drug development (Robinson & Rickels, 2000, *Journal of Psychopharmacology* 20:593-596). The difficulty is particularly acute in clinical trials of psychiatric drugs, where placebo response rates of 30-40% or more are not uncommon (Thase, 1999, *Journal of Clinical Psychiatry* 60 (Suppl. 4): 23-31; Trivedi & Rush, 1994, *Neuropsychopharm* 11(1): 33-43; Quitkin et al., 2000, *Am. J. Psychiatry.* 157: 327-337), making discrimination of active drug effects especially demanding. Some studies of major depression have reported placebo response rates as high as 70% (Brown et al., 1988, *Psychiatry Res.* 26: 259-264).

Placebo-controlled trials are increasingly difficult to justify on ethical grounds when an effective treatment is known (Quitkin, 1999, *Am. J. Psychiatry* 156: 829-836). In order to assure assay sensitivity, and/or in response to regulatory requirements, more trials are incorporating active comparators—drugs which are known to have efficacy in treating a particular disorder. In such trials sensitivity assumes an even more important role for detecting the small differences between two positive outcomes.

To enhance the statistical power of a given clinical trial, investigators can simply include greater numbers of patients. However, this approach has several major drawbacks. First, it adds substantially to the cost of performing clinical trials, as the cumulative per-subject costs often represent the majority of the total costs of a trial. More importantly, this approach requires that larger numbers of patients be exposed to experimental drugs, or drugs that may not yet have shown clear benefit for their illness. Unfortunately, increasing the number of patients is also associated with an increased placebo response rate (Keck et al. 2000, *Biol. Psychiatry* 47: 748-755; Keck et al., 2000, *Biol. Psychiatry* 47: 756-761; Shatzberg & Kraemer, 2000, *Biol. Psychiatry* 47: 736-744), thereby negating to some extent the benefit of an increased sample size.

Another mechanism for enhancing the power of a clinical trial involves improving the reliability of outcome measurements (Leon et al., 1995, *Arch. Gen. Psychiatry* 52: 867-871). When outcome measurements require human evaluation of clinical status, reliability depends on the skills of the human raters performing the evaluation. Improving and/or making the skills of human raters reliable and sensitive present a significant hurdle in designing, conducting, and even analyzing clinical trials.

Another feature of clinical trials is the need for one or more launch meetings to, inter alia, train raters, provide information to study coordinators and leaders, and discuss the underlying methodology. Such launch meetings for training raters can be quite expensive, particularly if many such meetings are required.

Current Methods of Rater Training

Although many clinical trials depend on raters, previously known methods leave much to be desired. In psychiatric clinical trials, for example, ratings by human raters are often the primary outcome measures. Despite the critical role of human raters, large clinical trials typically offer only cursory rater training at a study launch meeting just prior to rater certification. Over the course of a 1-3 day launch meeting, the time allotment for training and rater certification is usually 2-4 hours. In addition, experience shows that human raters are frequently unaware how important it is to the success of a study that rater reliability be maintained.

Often current rater training may be limited to reading though items on the rating scale(s). Some trials offer raters verbal and written conventions to help standardize the approach to common rater dilemmas (e.g., round up when rating falls between two anchor points, rate each item independently of contribution of concomitant drugs or general medical conditions). Trials generally do not provide raters with scripts for the primary outcome measures or other instruction for limiting the variation in a scale score due to the interview itself.

Problems in Rater Training

Initial rater training, though necessary, is often of limited value. The interval between the launch meeting and local site enrollment of patients into the clinical trial is seldom less than three weeks and is often more than three months. Even when training manuals are provided, the raters often fail to consult them.

Variations in scoring conventions from one trial to another may further dilute the benefits of initial rater training. As a result, raters may deviate from the training instructions. It is not unusual to find, for example, raters in a study using the Young Mania Rating Scale (YMRS) (Young et al., 1978, *Br. J. Psychiatric.* 133: 429-435) applying scoring conventions that were taught in a previous training session for a completely different study that used another rating scale such as the Schedule for Affective Disorders and Schizophrenia, Current symptom version ("SADS-C") mania rating scale.

Even the most skillful training at a launch meeting cannot train raters who do not attend the meeting. Some studies cope with this problem by staging multiple launch meetings, but this is expensive and does not address the need (which commonly arises) to hire additional raters after study start-up. Variations between the different launch meetings (which may be conducted by different personnel) may result in further rater variability.

Problems in Rater Certification

Rater certification refers to the process by which rater performance is documented to be within an acceptable range. Common practice for certification requires raters to score a rating scale based on viewing a videotaped patient interview. Certification is typically based on achieving agreement as determined by calculation of an intra-class correlation coefficient or more often by reference to an expert consensus score that serves as a "gold standard." Most clinical trials attempt to certify raters at the launch meeting itself, and require raters to meet a certification standard when tested on a single occasion. Since certification is typically carried out immediately following the training, the frequency at which raters achieve the targets of certification is likely to be much higher than might be expected with a delay between launch meeting and certification.

There is thus a need to improve the certification of raters, and to reduce the time between certification and clinical administration of ratings scales. There is also a need to permit certification outside of a clinical launch meeting environment.

The Need for Improved Rater Reliability

The need for standardized rater training has been described (Muller & Wetzel, 1998, *Acta. Psychiatr. Scand.* 98: 135-139). To minimize measurement error, investigators seek more consistent and better-trained raters. Unfortunately, since most large trials occur over a long period of time and involve multiple centers, each with its own raters, the logistical obstacles to standardized training continue to be serious hurdles.

Even modest gains in rater reliability can reduce result in substantial reduction in the sample size requirement, time, cost and risk of failure that can thwart development of promising therapeutic agents. For example, Perkins et al. (*Biol. Psychiatry* 47: 762-766 (2000)) calculated that an improvement in reliability from R=0.7 to R=0.9 could reduce sample size requirements by 22%. This may often translate into significant cost savings.

In psychiatric trials (i.e., trials of therapy for a psychiatric disorder), where objective biological outcome measures may be lacking, reliability may be particularly poor, as investigators typically rely on rating scales completed by human clinicians. Seeking to quantify subjective experiences or behavior introduces substantial measurement error. Thus, the need for increased rater reliability is even greater in psychiatric trials.

Problems of Ongoing Reliability

Certification of raters under controlled conditions leaves room for error and abuse as well as simple incompetence during the actual conduct of study ratings. Many studies utilize raters operating under considerable time pressure. Experience indicates that rating scale scores are significantly correlated with the duration of the rating interview and that time allotted for the interview tends to decrease over the course of a study. Attempting to interview patients in a fixed time tends to lower the scores of symptomatic patients, reducing potential drug-placebo differences.

Audio or video taping of interviews could effectively ameliorate this problem, but is a costly, time intensive, and intrusive methodology that requires an elaborate system of expert review, resolution of differences and remediation. Each tape must be reviewed in its entirety by an expert, or panel of experts, effectively doubling or tripling the amount of time required to obtain a particular rating. Moreover, this methodology is often unacceptable to patients and raters. Awareness of the tape recording may alter patient behavior (and the resulting ratings). For example the patient may feel more self-conscious about discussing sensitive or embarrassing topics while being recorded.

There is thus a need for efficient monitoring of raters during the course of a trial in order to detect rater drift and variance so that remediation efforts and recertification may be instituted when necessary.

Problems of Recertification

Re-certification of raters refers to the process by which previously certified raters are reexamined to confirm that their ratings remain calibrated to study standards. This process aims to measure and reduce the tendency for raters to drift away from the rating norms established at study start-up. In theory, this is a relatively simple process that can be accomplished by having raters rate videotapes for which consensus or "gold standard" ratings have been established.

Despite the desirability of re-certification, few studies ever recertify raters. The simple requirement for additional tapes with gold standard rating is not particularly challenging. More significant obstacles include the expense of reassembling the raters in a central location or coordinating rater schedules with those of a visiting monitor. Additionally, there is a risk that failure of a single rater to recertify may cripple a site in the midst of study operations.

There is thus a need for a re-certification process that is more convenient and better integrated into the conduct of clinical trials.

SUMMARY OF THE INVENTION

In one aspect, the present invention provides a computerized system and method for training, monitoring, certification or re-certification of clinical raters by presenting to a rater one or more segments of a simulated or recorded patient interview, obtaining from the rater one or more scores in response to the presented interview segment or segments, and comparing the one or more rater scores with one or more reference ratings for the presented interview segment or segments. In one embodiment, the reference rating is an expert rating or a consensus rating by a plurality of experts. In another embodiment, the reference rating is a consensus score of a plurality of raters, for example a rating determined by intra-class correlation of scores entered by a plurality of raters. The invention is suitable for training, monitoring, certifying or recertifying raters at a plurality of distinct locations or at a plurality of times and advantageously provides different raters with individually paced training, monitoring or certification sessions. The invention facilitates the provision of individual sessions at a plurality of places and/or times to suit the convenience of individual raters.

In a second aspect, the invention provides a computerized system and method for evaluating or quantifying the severity of a condition (including a previously diagnosed condition such as a psychiatric or other illness) through a automated interview that may be termed an interactive computer interview (ICI). The system elicits information from the subject in response to prompts comprising an interactive interview and determines a computerized symptom severity rating or score for the subject in accordance with a clinical rating scale. During the interactive computer interview, the system preferably uses branching logic whereby a question or prompt is selected for presentation to the subject from a variety of alternative question or prompts, based on the subject's response to a prior question or prompt (e.g. the immediately preceding question or prompt). This process of selection can be iteratively performed for any desired number of cycles. Preferably, the interview is automatically terminated when sufficient information has been gathered, according to previously determined criteria. The interactive computer interview is thus tailored for the subject, without the need to present all possible questions or prompts to the subject and/or without the need to present a predetermined number of questions or prompts to the subject.

In a third aspect, the invention provides a system and method for monitoring, certifying, recertifying or improving the performance of clinical raters, on a continuing basis if desired. This advantageously assists diverging raters to reduce the variance of their symptom severity scores or ratings from reference ratings (which may be consensus standard or expert ratings obtained by conducting one or more human clinical interviews, or ratings determined by one more interactive computer interviews). The system compares one or more scores by the rater with one or more reference ratings to determine whether the score(s) of a given rater show a variance from the reference rating(s) that exceeds a given threshold. Based on the results of the comparison, the frequency of computerized rating may be adjusted. If the difference between the computerized rating and the score determined by the human rater exceeds a defined threshold (e.g. a predetermined limit), the system can optionally suggest or initiate remediation to improve the human rater's performance. The remedial plan may be implemented by a rating instructor (e.g. the system can generate a script for a telephone call), or by providing the deviating rater with electronic access to stored conventions explaining how those items should be scored.

In a fourth aspect, the invention provides a computerized system and method for evaluating a subject for inclusion in or exclusion from a clinical trial. The subject is evaluated by eliciting information from the subject by means of an interactive computer interview. Rating scale information calculated from the responses of the subject in accordance with a clinical rating scale permits comparison with one or more predetermined criteria to indicate whether or not the subject qualifies for inclusion in the clinical trial.

In a fifth aspect, the invention provides a computerized system and method for evaluating the severity of an individual's symptoms prior to or following administration of a therapy (e.g. a medication) or a placebo. This evaluation is based on a comparison of rating scale information determined by an interactive computer interview with the results of a prior interactive computer interview or with at least one predetermined criterion, e.g., consensus of one or more experts. Thus, the severity of the individual's symptoms may be evaluated or serially followed without the involvement of a human clinical rater.

In a sixth aspect, the invention provides a system and method for training (or retraining) a clinical rater to conduct a script- (or semi-script-) based clinical rating session. In one embodiment the system prompts the rater with a question to ask the patient, and based on the patient's response entered by the rater, prompts the rater with the appropriate next question to ask the patient. In another embodiment, the system is used in the absence of a patient to allow a rater to be trained in the logic and language of a scripted interview, for example by presenting to the rater one or more stored segments of an actual or simulated patient interview.

The invention also provides a computer programmed with executable instructions for carrying out the steps of the methods described herein. Such instructions may be useful in configuring hardware or in executing the logic for the cooperation of a plurality of components, and may be stored on a computer readable medium, e.g., in the memory of a computer or a computer network, whether as routines, as program modules, or in any convenient format. The invention further provides a computer-readable medium comprising instructions for causing a computer to carry out the steps of the methods described herein.

BRIEF DESCRIPTION OF THE DRAWINGS

FIG. 21 illustrates a flowchart for a script associated with the MADRS to measure the "concentration difficulty" item.

DESCRIPTION OF THE PREFERRED EMBODIMENTS

Figure 1:
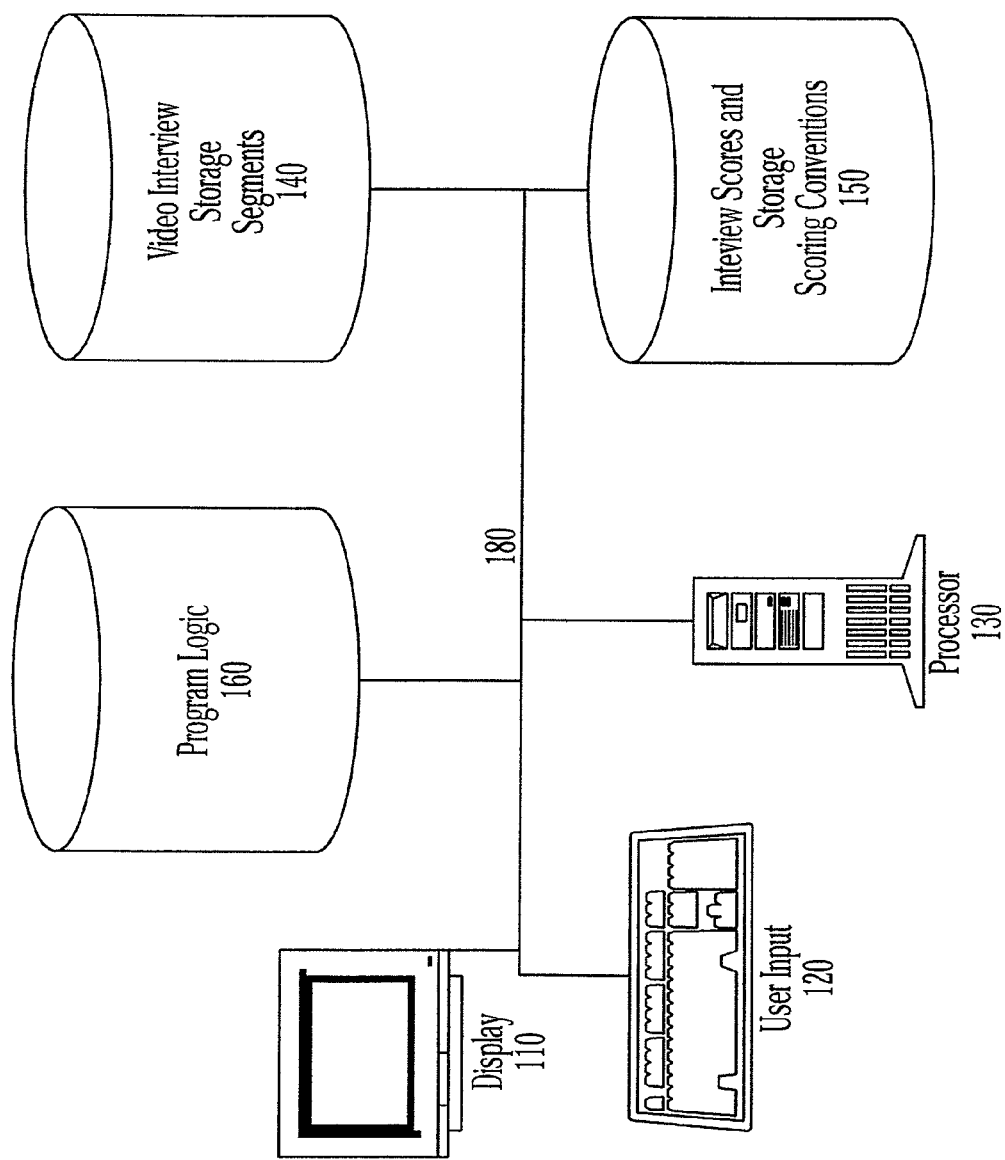
FIG. 1 schematically depicts a system architecture for one preferred embodiment of the invention.

The system of the present invention comprises a plurality of components for computerized processing such that the components cooperate to implement the presently disclosed methods. The components in the system may be hardware, which may include an output device (e.g. a display device such as a screen, monitor or television, or a loudspeaker or telephone), a workstation, an input device (e.g., a keyboard, numerical keypad, dial, touch screen, touch pad, pointing device such as a mouse, microphone or telephone), software (typically for configuring the hardware), and preferably are a combination of hardware and software.

An exemplary system for implementing the invention comprises two or more components cooperating to implement the methods of the invention in a suitable computing environment, e.g., in the general context of computer-executable instructions. Generally, computer-executable instructions may be organized in the form of program modules, programs, objects, components, data structures, etc. for performing tasks or implementing data and objects.

Although implemented with the aid of a computing device, the invention may be implemented with a wide variety of such devices including personal computers, hand-held devices, multi-processor systems, microprocessor based or programmable consumer electronics, network PCs, minicomputers, mainframe computers, and the like. The invention may also be practiced in distributed computing environments where tasks are performed by remote processing devices that are linked through a communications network. The communication between various components in a suitable system may be synchronous or asynchronous or a combination thereof. In a distributed computing environment, program modules or data may be located in local or remote memory storage devices.

An exemplary system for implementing the invention includes a suitably configured general purpose computing device. A conventional computing environment typically may include a processing unit, a system memory, and a bus that couples two or more components. The system bus may be any of several types of bus structures including a memory bus or memory controller, a peripheral bus, and a local bus using any of a variety of bus architectures. The system memory includes read only memory (ROM) and random access memory (RAM). A basic input/output system (BIOS), containing the basic routines that help to transfer information between elements within the computing environment, such as during start-up, is stored in the ROM. The computing environment further includes a hard disk drive for reading from and writing to a hard disk, a magnetic disk drive for reading from or writing to a removable magnetic disk, or an optical disk drive for reading from or writing to a removable optical disk such as a CD ROM or other optical media.

The storage devices, such as the hard disk drive, magnetic disk drive, and optical disk drive may be connected to the system bus by a hard disk drive interface and a magnetic and/or optical disk drive interface, respectively. The drives and their associated computer-readable media provide nonvolatile storage of computer readable instructions, data structures, program modules and other data for the computing environment. Although the exemplary environment described herein employs a hard disk, it will be appreciated by those skilled in the art that other types of computer readable media which can store data that is accessible by a computer, such as a removable magnetic disk, and a removable optical disk, magnetic cassettes, flash memory cards, digital video disks, Bernoulli cartridges, random access memories, read only memories, and the like may also be used in the exemplary operating environment.

The computing environment may include computer readable media such as volatile or nonvolatile, removable or non-removable media implemented in any technology or method for information storage such as computer instructions, data structures, program modules and the like. Computer storage media includes, but is not limited to, RAM, ROM, EEPROM, flash memory, or other memory technology, CD-ROM, CD-RW disks, Digital versatile disks ("DVD") etc. that can be used to store and access the information. Communication media typically includes computer readable instructions, data structures, program modules or data in a modulated data signal such as a carrier wave.

A number of program modules may be stored on the hard disk, magnetic disk, optical disk, ROM or RAM, including an operating system, one or more applications programs, other program modules, and program data for implementing the methods of the present invention. A user may enter commands and information through input devices such as a keyboard and a pointing device. Other input devices (not shown) may include a microphone, joystick, game pad, satellite dish, scanner, or the like. These and other input devices are often connected to the processing unit through an interface, such as a serial port interface that is coupled to the system bus. Increasingly, such devices are being connected by the next generation of interfaces, such as a universal serial bus (USB) with a root hub/Host, and to which other hubs and devices may be connected. Other interfaces that may be used include parallel ports, game ports, and the FireWire, i.e., the IEEE 1394 specification. Output devices include a monitor or other type of display device may also be connected to the system bus via an interface, such as a video adapter. In addition to the monitor, personal computers typically include other peripheral output devices, such as printers, projectors, and the like.

The computing environment may be networked using logical connections to one or more remote computers, such as a remote computer. The remote computer may be a server, a router, a network PC, a peer device or other network node, and typically includes many or all of the elements described above relative to the computing environment. The logical connections underlying the computing environment may include a local area network (LAN) and a wide area network (WAN) with wired or wireless links. Such networking environments are commonplace in offices, enterprise-wide computer networks, intranets and the Internet with client-server or peer-to-peer networking protocols. USB provides another way to connect to a network by either using a communication link via a wireless link, a modem, an ISDN connection and the like, or even a hub that can be connected to two computers.

When used with an underlying LAN networking environment, the computing environment is connected to the local network through a network interface or adapter. When used in a WAN networking environment, the computing environment typically includes a modem or other means for establishing communications over the WAN. The modem, which may be internal or external, is connected to the system bus via the serial port interface. In a networked environment, program modules depicted relative to the computing environment, or portions thereof, may be stored in the remote memory storage device. It will be appreciated that the network connections shown are exemplary and other means of establishing a communications link between the computers may be used.

Turning to the drawings, wherein like reference numerals refer to like elements, in a preferred embodiment, the present invention may be implemented using the hardware and software schematically illustrated in FIG. 1. An output device, display 110 and user input device 120 are operatively coupled to processor 130. Also coupled to processor 130 is program logic 160, audio, video or multimedia interview segments storage 140, and interview scores and scoring conventions storage 150.

In one preferred embodiment, these components comprise a personal computer, such as an IBM PC compatible equipped for digital video, or multimedia display, and optional speakers for audio output, and a CD-ROM or DVD storage device for audio, video or multimedia storage, and a hard disk for interview scores and scoring convention storage. In another embodiment, display 110 and user input device 120 comprise an World Wide Web client such as a PC running Web browser software, and Audio, Video or Multimedia Interview Segments Storage and Interview Scores and Scoring Conventions Storage 150 comprise disk storage on a HTTP server. Since, alternative embodiments of the invention may employ peer-to-peer networking, the invention is not limited to client-server based communications.

The HTTP server preferably can accept input from fields displayed in a web-page and provide a result based thereon. In addition, logic executed on the server and/or client side allows the web-page to check information and process it, for instance, to implement scripts or semi-scripts. Scripts provide preset logic (e.g. branching logic) for determining the next question or set of questions from the answers to preceding question or set of questions. Semi-scripts allow for greater flexibility by suggesting the next set of questions rather than determining them in response to the answers, hence allowing for human input in selecting the next set of questions, e.g., drop down menus. It should be noted that the human rater or subject may interpret answers to the questions in the course of assigning a score or a classification independent of the use of scripts or semi-scripts or an open format for posing questions. Such human interventions do not preclude the use of scripts or semi-scripts.

The communication between various hardware and software components may be based on, for instance, optical, electronic, wireless technologies, or combination of such technologies. Example technologies include wireless local area networks (WLANs) using HIPERLAN/2, the IEEE 802.11a, the IEEE 802.11b, or the Bluetooth specification and local area networks (LANs). Such networks may optionally be secured, e.g., by implementing virtual private networks, requiring passwords, employing encryption, or actual physical separation, and the like. Moreover, the Internet may optionally be employed to further extend the reach of the system to include additional distributed resources. It will be apparent to those of skill in the art that a wide variety of hardware and software may be adapted to implement the present invention. The coupling of the devices depicted in FIG. 1 is by way of logical network 180. Logical network 180 represents networking interconnections such as one or more of client-server, peer-to-peer, point-to-point connections, synchronous link, asynchronous link, LAN, WAN, or WLAN and the like.

In one aspect, the invention comprises a system for rater certification and re-certification. The system preferably comprises storage 140 for audios, videos, or multimedia of patient interviews for computer controlled delivery (e.g., via streaming video), and processor 130 configured to execute program logic 160. Program logic 160 comprises a training program, which allows raters to interactively complete rating scales based on the encoded interviews. The system further comprises a comparison program that compares these ratings to consensus ratings and provides appropriate feedback.

In one preferred embodiment, a plurality of patient interviews, e.g., three patient interviews for the Young Mania Rating Scale (Young et al., *Br. J. Psychiatric.*, 1978; 133: 429-435) and/or three patient interviews for Montgomery-Asberg Depression Rating Scale (MADRS; Montgomery & Asberg, *Brit. J. Psychiatry,* 1979; 134: 382-389) are digitally recorded and stored in audio, video, or multimedia storage 140 in a digital format for computerized interactive delivery. Benchmark scores are determined by a consensus of a plurality of experts, preferably one, two, three, four, or five experts, for a plurality of scoring items in the recorded interviews and recorded in storage 150, preferably in a database. In addition, for a plurality of scoring items on the rating scale or scales, consensus conventions used to determine the benchmark score are recorded in the database. The digitized interviews are incorporated into a multimedia rater certification or re-certification session that allows a rater to interactively input scores for scoring items on the rating scale(s).

The input scores are provided to a rating comparison program that compares the rater scores with the benchmark scores. Based on the comparison between the raters scores and stored consensus scores, the system determines whether the human rater can be certified. Optionally, the rater is interactively provided with indications of the benchmark scores and the benchmark conventions if the rater's score is discordant with the benchmark score or differs from the benchmark score by more than a threshold limit (which may or may not be a predetermined limit).

Figure 2:
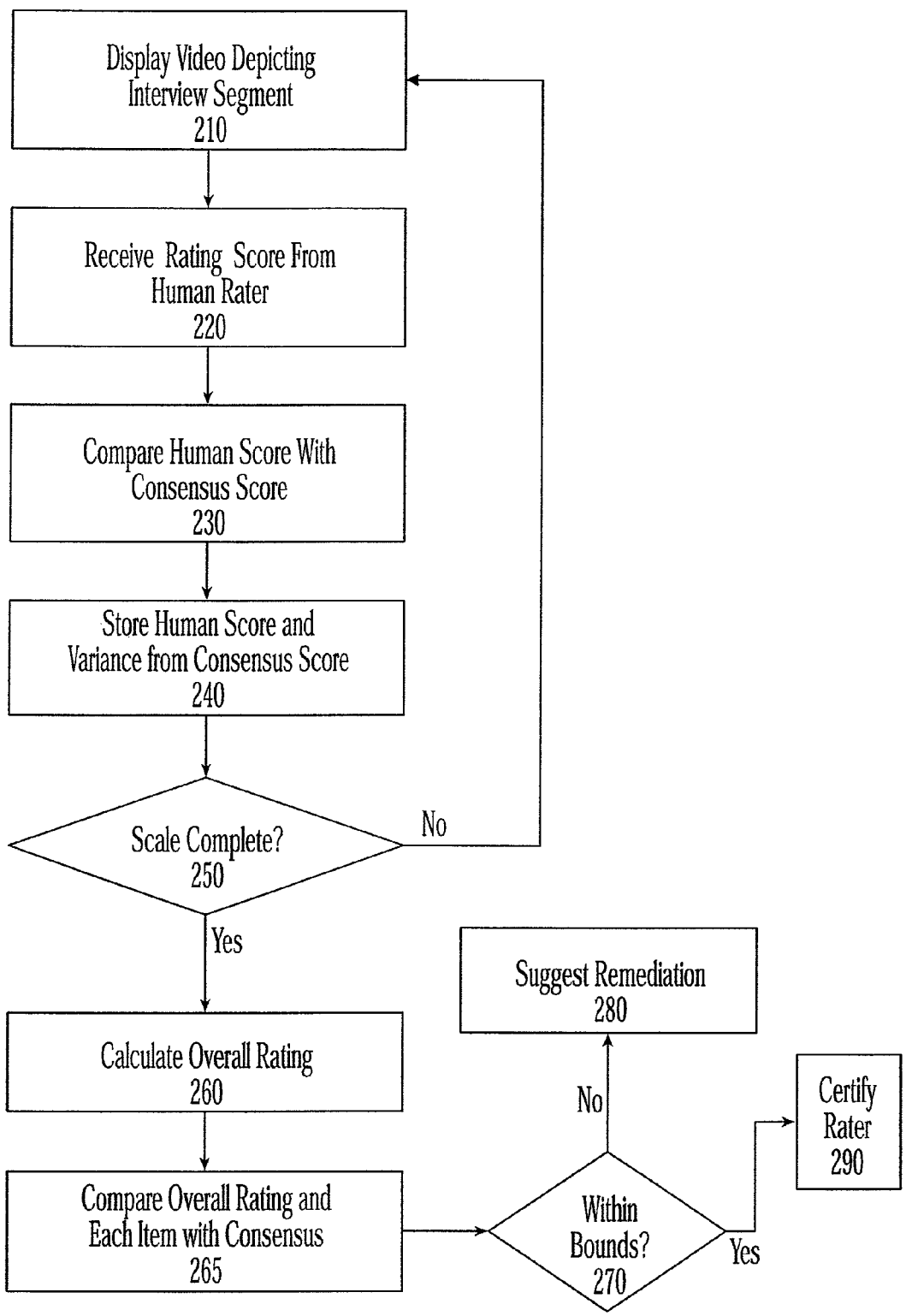
FIG. 2 schematically depicts an example of a preferred embodiment of the invention for rater certification.

As schematically illustrated in FIG. 2, in this aspect, a method of the present invention, during step 210, displays an audio, video, or multimedia depiction of a segment of an interview with a patient, and prompts the human rater to enter a score for an item corresponding to the interview segment. During the next step 220, the system receives rater's score, and compares it with stored consensus score during step 230. By way of an example, the rater's score may be received in the form of entries to a web page displaying a form. Such a form is preferably integrated with a script or a semi-script. Following determination of both the human rater's score and the variance of the human rater's score, they are stored during step 240. If the human rater has not completed all scoring items necessary to calculate a rating at step 250, then control flows back to step 210, which results in repeating steps 220, 230, and 240. Once the entries are complete, control flows from step 250 to step 260, during which the system calculates the overall rating based on the human rater's entries. Next, during step 265, the human rater's overall rating is compared with the consensus overall rating, and the variance of each of the rater's scores is compared with the consensus scores 265 with control passing to step 270. If, at step 270, the overall rating and the individual scores are within pre-established bounds for rating and scoring, then at step 290 the human rater is determined to be certifiable or re-certifiable. Alternatively, control flows from step 270 to step 280 and remediation is suggested.

Instead of consensus ratings in step 265, alternative embodiments may use the ratings by one or more trainers. Thus, many of the steps in FIG. 2 including step 265, may be useful in alternative embodiments of the invention, in monitoring or training raters. Re-certification may be required in response to such monitoring. In alternative embodiments, re-certification may be in response to regulatory, voluntary or part of the design of the clinical trial itself. In alternative embodiments of the invention, this process can result in certification of a rater as well. Such certification is of significant value since it is economical, efficient and reliable while permitting introduction of raters in the trial after the launch of the trial.

In one embodiment, the invention provides an Interactive Computer Interview (ICI) that elicits symptom severity data either directly from a patient (e.g., by presenting prompts of questions to the patient, who then enters a response by means of a suitable input device), or via an intermediary, who need not be a trained rater, thereby using a computer to simulate a skilled clinician's administration of the rating scale. The ICI system may incorporate script and/or semi-scripts and may provides prompts or questions in the form of audio, video, or multimedia segments. The system can provide prompts (such as "yes or no" or multiple choice questions) to the subject. Questions may be presented on a screen or may be read aloud to the subject, such as by playing a pre-recorded message or by computer-generated speech. Preferably, the questions appear on a screen (or are read to the subject) one at a time, the next question being presented after the subject has responded to the prior question. Preferably, the ICI does not use a rigid standardized script, but is capable of asking questions that depend upon a subject's responses to previous questions (e.g. a given question is selected from a number of possible alternatives depending on the subject's response to the immediately preceding question or to an earlier question or depending on the subject's responses to multiple prior questions). In this way, the system can pose probing or follow up questions to a subject. In a preferred embodiment, when the system determines that sufficient data have been collected for a specific item, the ICI records a score for the subject and moves on to the next item, thereby advantageously avoiding the need to present unnecessary or irrelevant questions to the subject during the ICI.

In one embodiment, an interactive computer interview (ICI) of a subject is performed in conjunction with assessment of that subject by a human rater. Preferably, the ICI is performed within 24 hours before or after assessment by the human rater, more preferably at the same clinic visit, and ideally immediately after assessment by the human rater, before the subject leaves the clinic. A rating comparison program can compare the results of the ICI with results obtained by the human rater. Based on the results of the comparison, the system can provide ongoing feedback to a rater, can indicate (e.g. to a supervisor or trial administrator) that remedial measures are needed, or can provide remedial measures to the deviating rater to help improve that rater's performance, e.g. to keep that rater's scores within acceptable variance from benchmark or reference ratings. Alternatively, inaccurate raters (e.g. raters whose scores deviate from reference or benchmark scores by greater than a given threshold or raters whose scores are persistently discordant) can be suspended or eliminated from further participation, or scores of inaccurate raters can be eliminated or ignored for purposes of analysis. In a preferred embodiment, a protocol for a clinical trial prospectively specifies standards for identifying inaccurate raters and for eliminating the scores of inaccurate raters from analysis.

In a further embodiment, the invention provides a method and system for evaluating severity of symptoms enabling use of ICI to evaluate patients, for instance during a clinical trial (such as a Phase I, Phase II or Phase II trial) or in order to screen patients for inclusion in or exclusion from a trial such as a clinical trial. In this aspect the present invention provides a system and method for automated evaluation of patients without the involvement of a human rater. Replacement of human raters in the manner taught by the invention is possible with calibration of computer rating, for instance with the aid of one or a plurality of experts.

Alternatively, these ratings may be incorporated into routine clinical practice in mental health, as a means of gathering additional information for the medical record prior to the patient's visit with the clinician. In this embodiment, the patient completes the ICI prior to the clinical visit: for example, while in the waiting room, or from home prior to the appointment. The use of branching logic allows for a far more detailed inquiry into symptoms and severity than a standard waiting-room form allows. The clinician may also draw upon the information gathered in this format to perform a more focused or detailed assessment during the face-to-face visit. These and other applications of ICI are further described in the accompanying illustrative figures and flowcharts.

Figure 3:
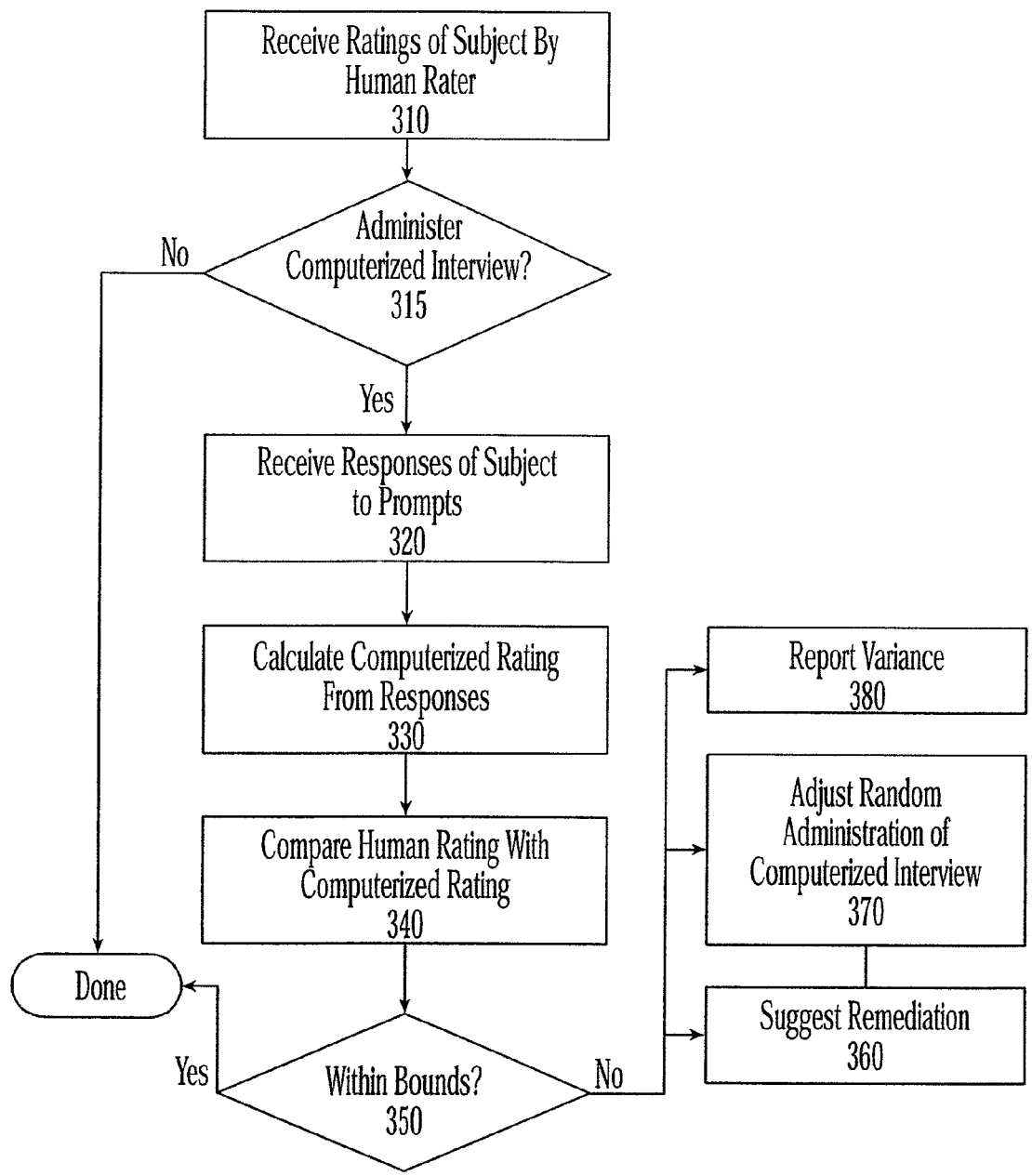
FIG. 3 schematically depicts an example of a preferred embodiment of the invention for rater reliability monitoring.

As schematically illustrated in FIG. 3, following administration of a rating scale by a human rater, during step 310, the ratings are received by system. Next, during step 315, a test is applied to determine whether an ICI should be administered to subject. Preferably, unless otherwise indicated, the subject is selected in a random manner consistent with unbiased sampling of the pool of subjects. This described strategy is not intended to be limiting and alternative embodiments of the invention may implement other strategies for selecting subjects and/or human raters for evaluation. If ICI is not to be administered the method terminates. Otherwise, control passes to step 320.

During step 315, if an ICI is to be administered to the subject, the system generates a series of prompts comprising a computerized interview, prompting the subject for information needed to calculate a computerized rating. During step 320, the system receives responses of the subject, and then, during step 330, calculates a computerized rating from the received responses. The system then, during step 340, compares the computerized rating with the human rating. During step 350, if the two are within acceptable variance bounds of each other, the session is complete. Otherwise, the variance is reported to clinical administrator during step 380 and remedial action suggested for the human rater during step 360. The rules for administering the test are also preferably adjusted during step 370 so that an ICI will be administered to the next subject rated by the human rater, and to the subject rated in this session the next time the subject is rated.

A preferred computerized implementation for the Young Mania Rating Scale (YMRS) is schematically described in APPENDIX A1, wherein the various items numbered from I to XI correspond to the scripts illustrated in FIGS. 5-15 respectively. Each of the items is a list of questions that are presented in accordance with the corresponding figure. Also shown are the acceptable answers for the questions. These answers may be presented, for example, as choices in a drop down menu, or a box to be selected, or as information to be entered. The responses to one or more questions may be automatically evaluated to ensure that they are acceptable responses. Thus, if a subject enters the letter "P" in response to a question calling for a "Y" (for yes) or "N" for no, then the question may be presented again in response to detecting an entry other than Y or N. Such optional automatable checking for consistency makes the administration of the script further resistant to inadvertent errors by the subjects.

Figure 5:
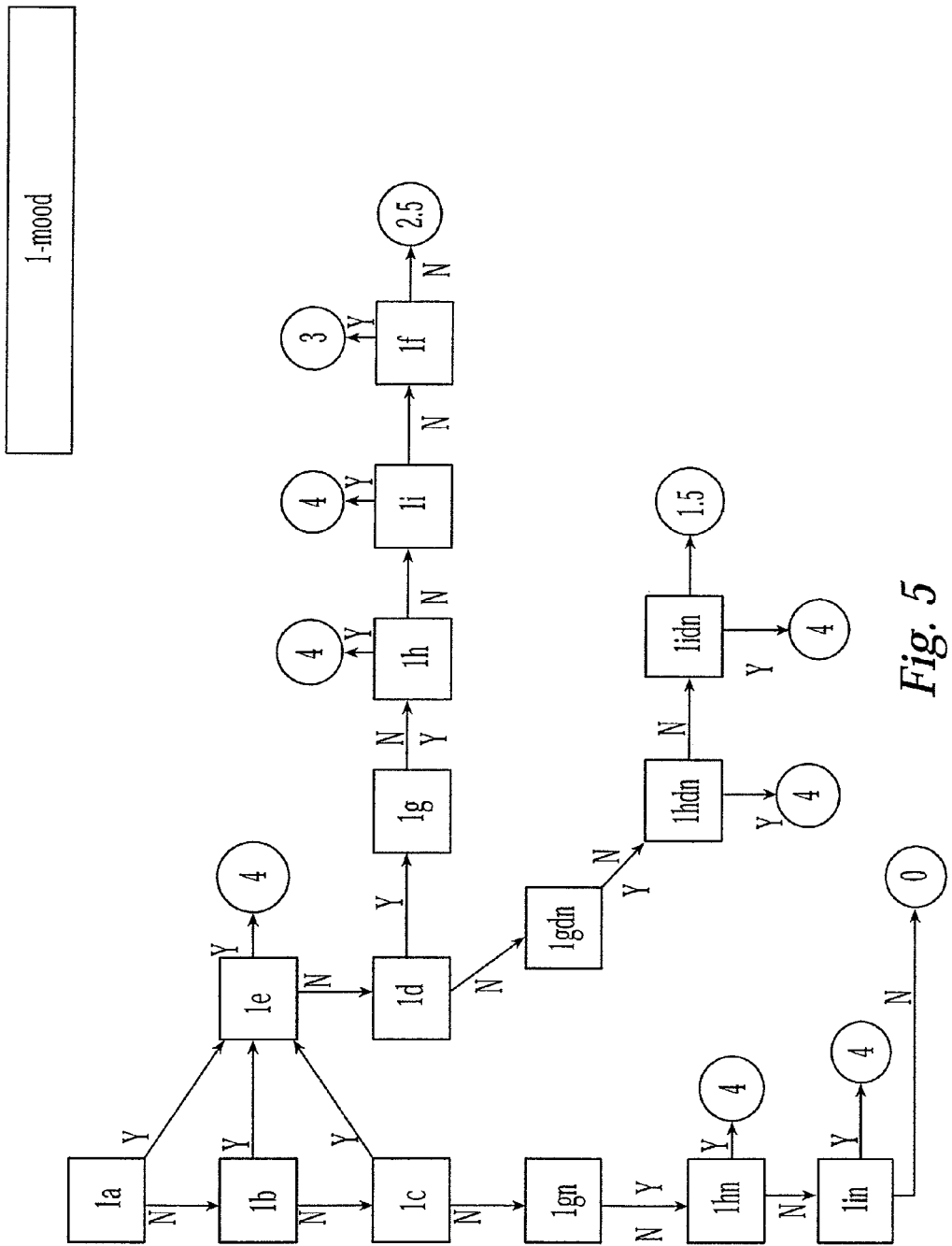
FIG. 5 illustrates a flowchart for a script associated with the Young Mania Rating Scale (YMRS) to measure the "mood" item.
Figure 6:
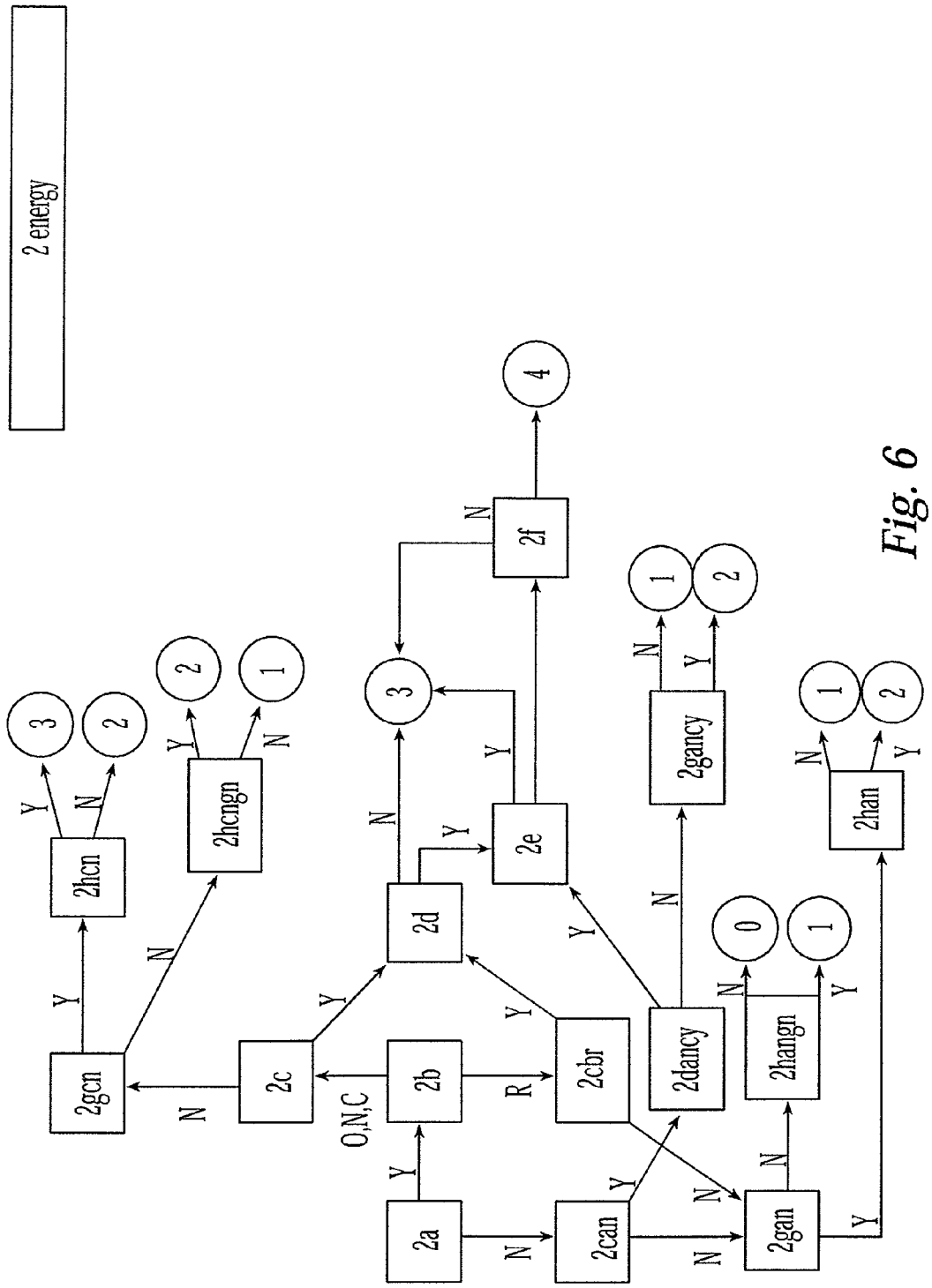
FIG. 6 illustrates a flowchart for a script associated with the YMRS to measure the "energy" item.
Figure 7:
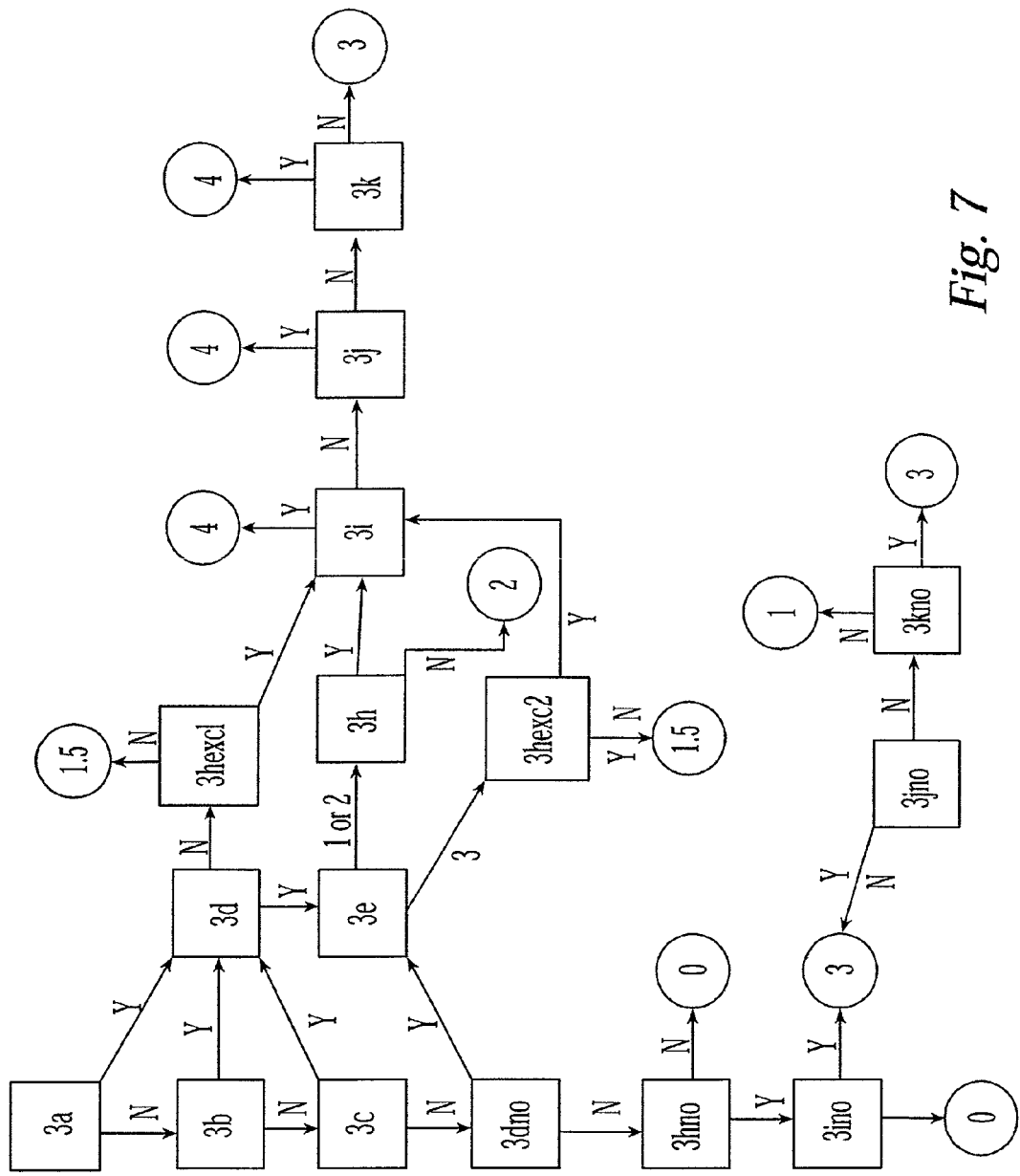
FIG. 7 illustrates a flowchart for a script associated with the YMRS to measure the "sexual interest" item.
Figure 8:
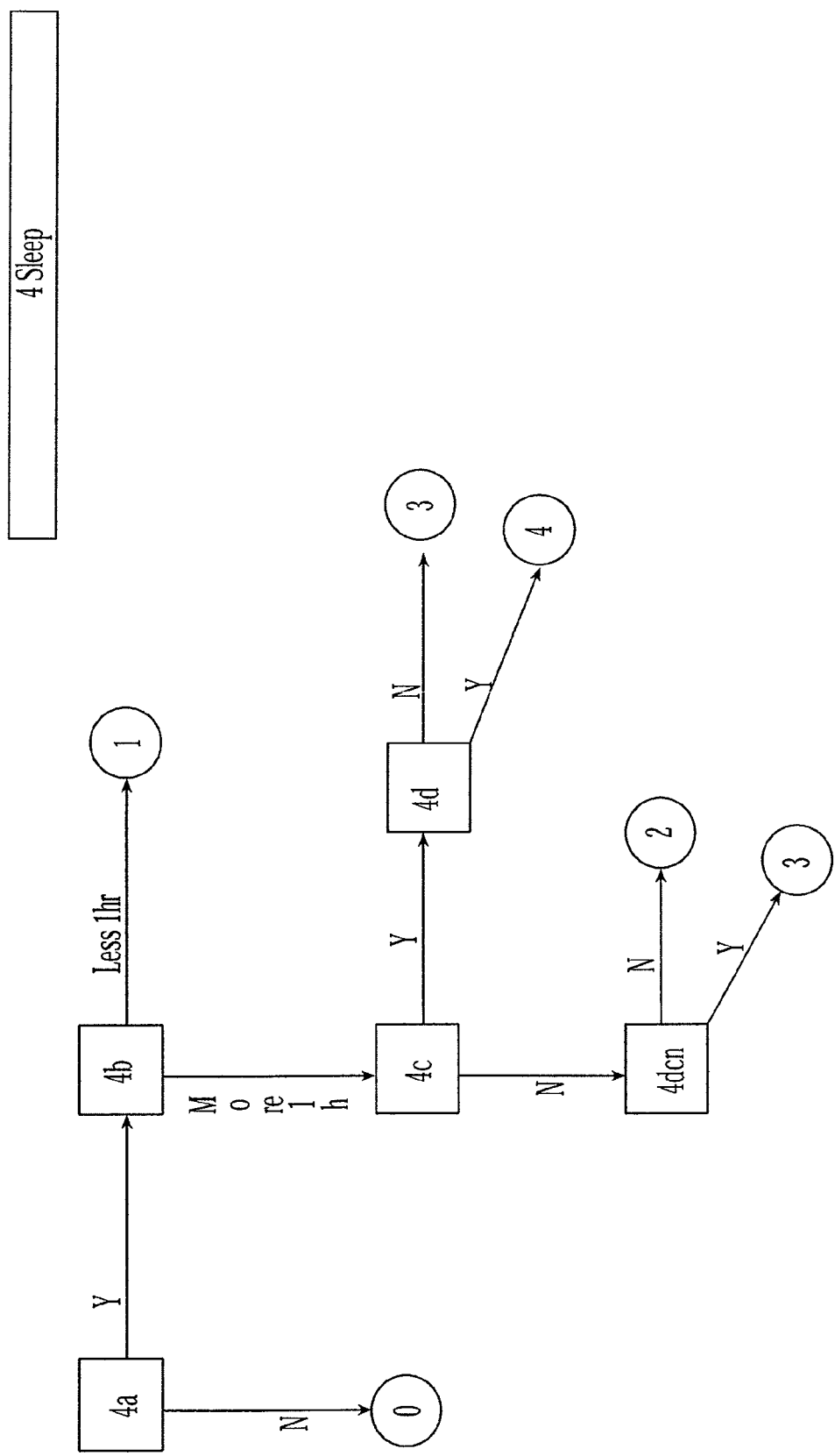
FIG. 8 illustrates a flowchart for a script associated with the YMRS to measure the "sleep" item.
Figure 9:
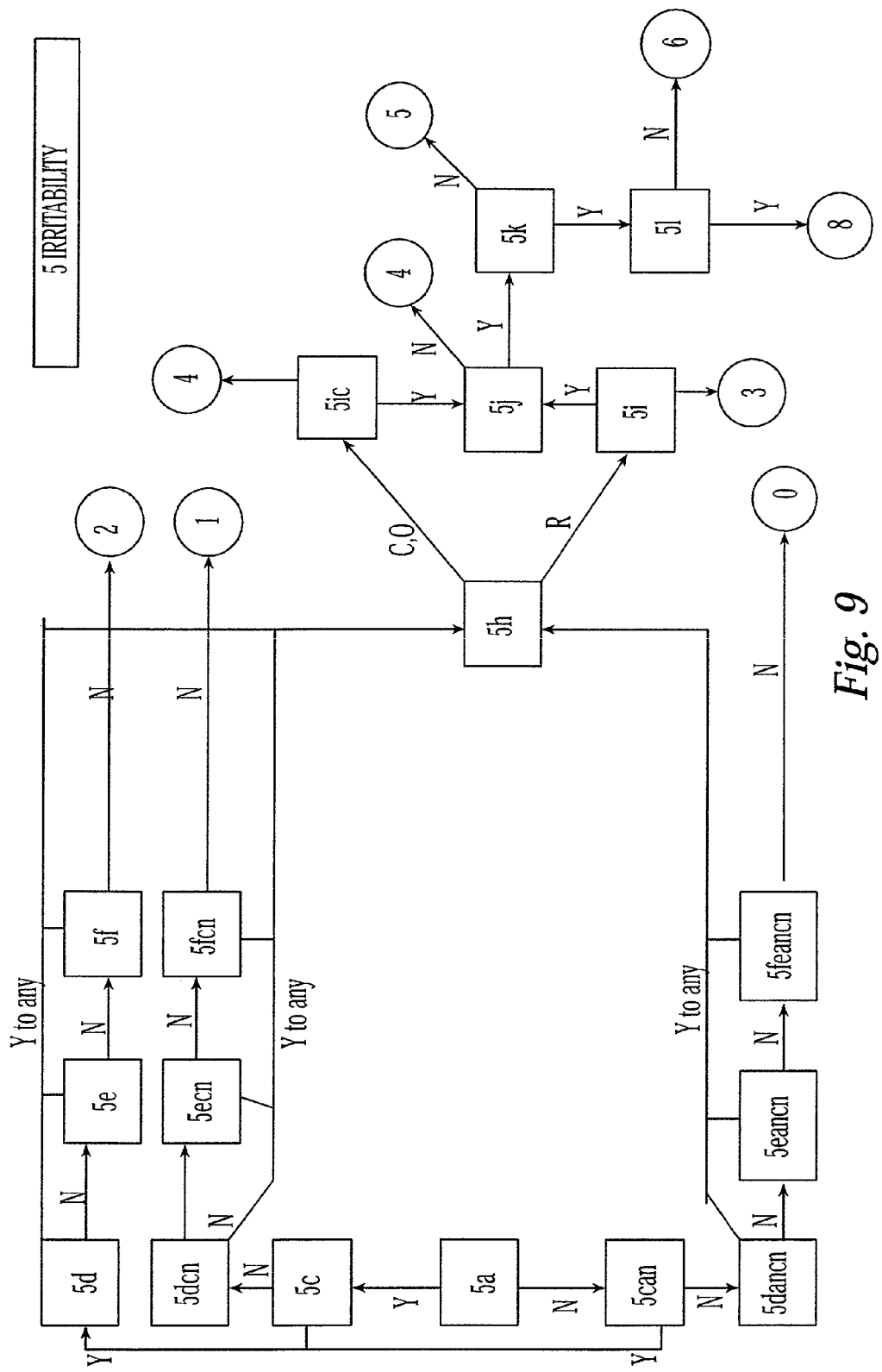
FIG. 9 illustrates a flowchart for a script associated with the YMRS to measure the "irritability" item.
Figure 10:
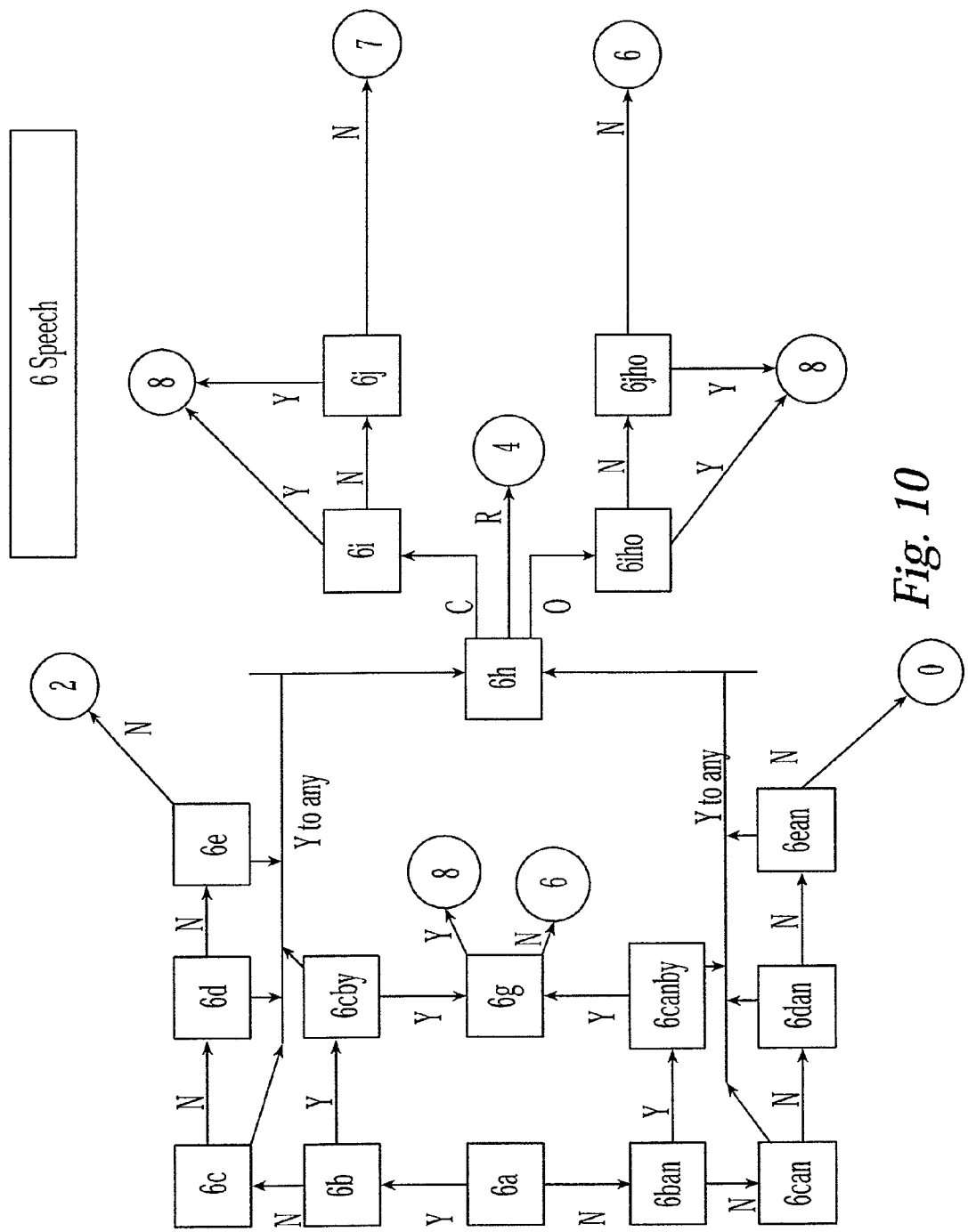
FIG. 10 illustrates a flowchart for a script associated with the YMRS to measure the "speech" item.
Figure 11:
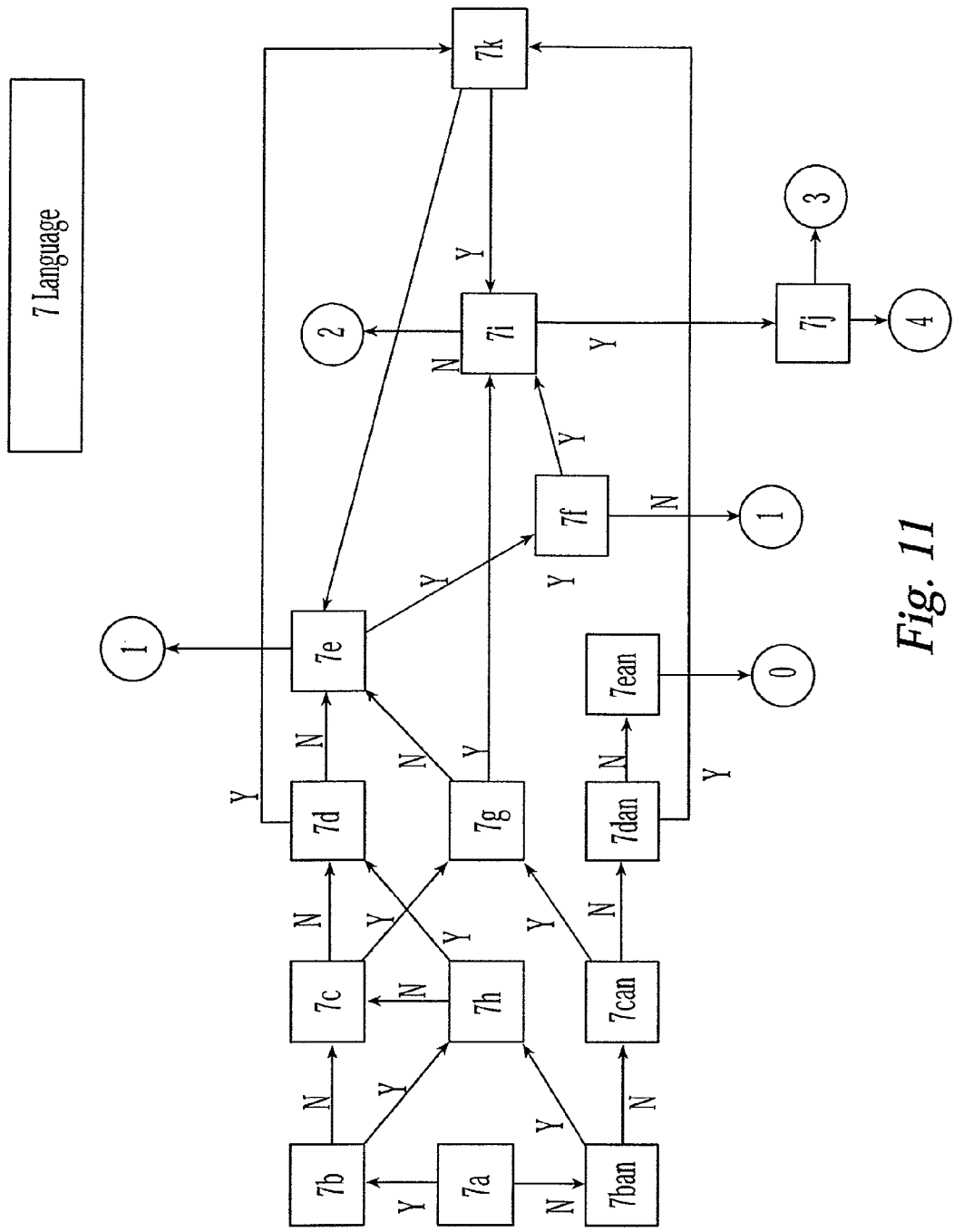
FIG. 11 illustrates a flowchart for a script associated with the YMRS to measure the "language" item.
Figure 12:
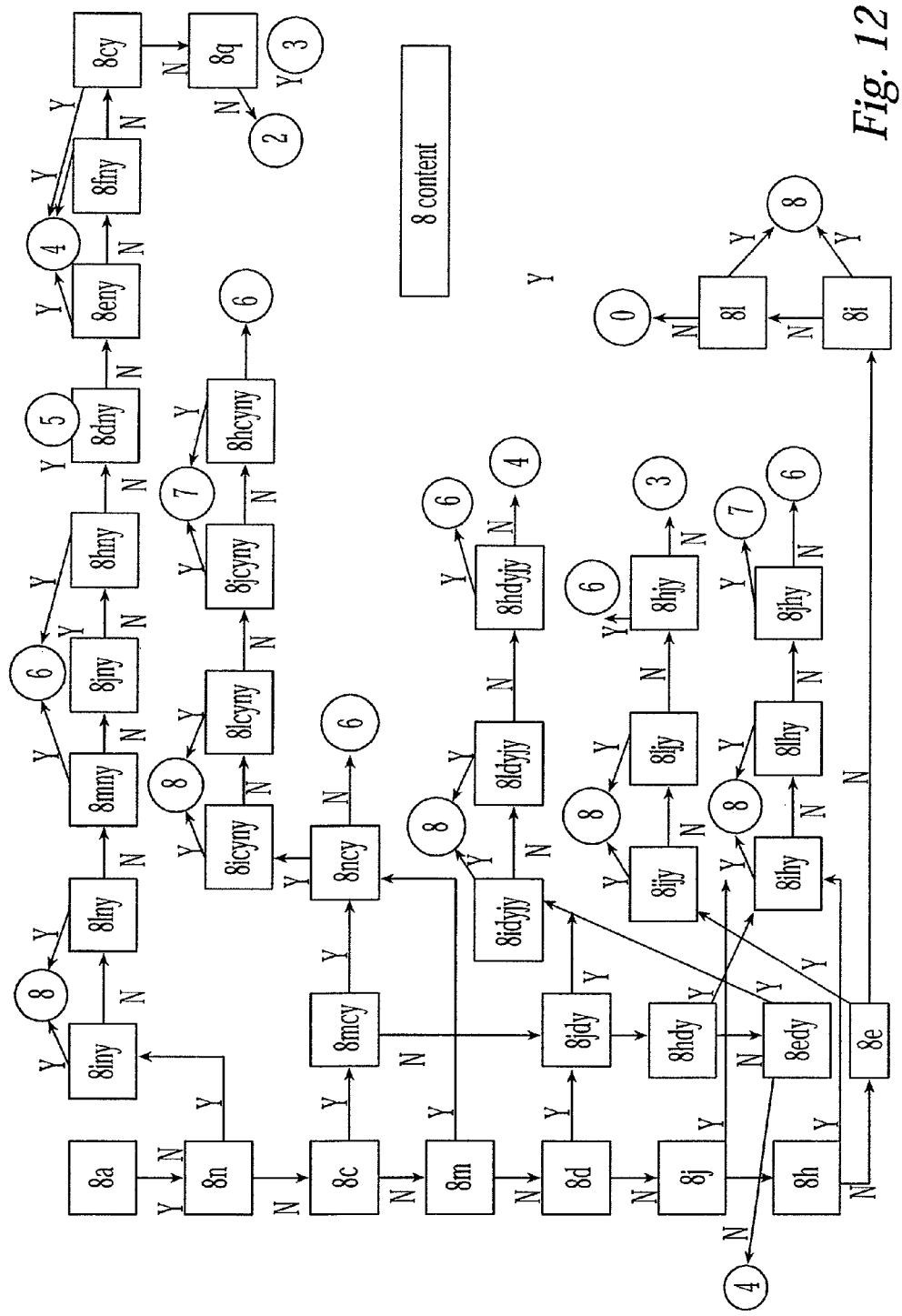
FIG. 12 illustrates a flowchart for a script associated with the YMRS to measure the "content" item.
Figure 13:
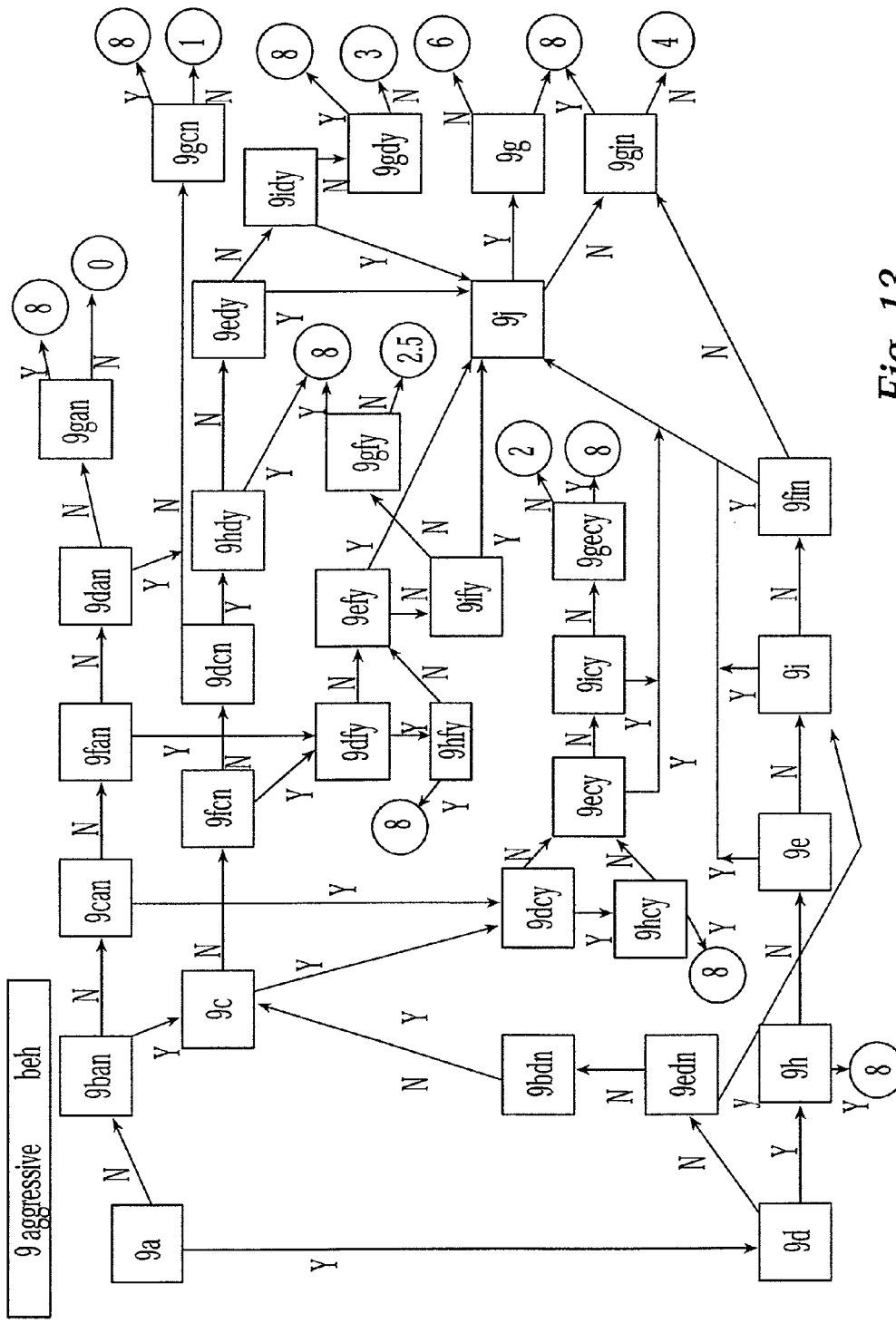
FIG. 13 illustrates a flowchart for a script associated with the YMRS to measure the "aggressive behavior" item.
Figure 14:
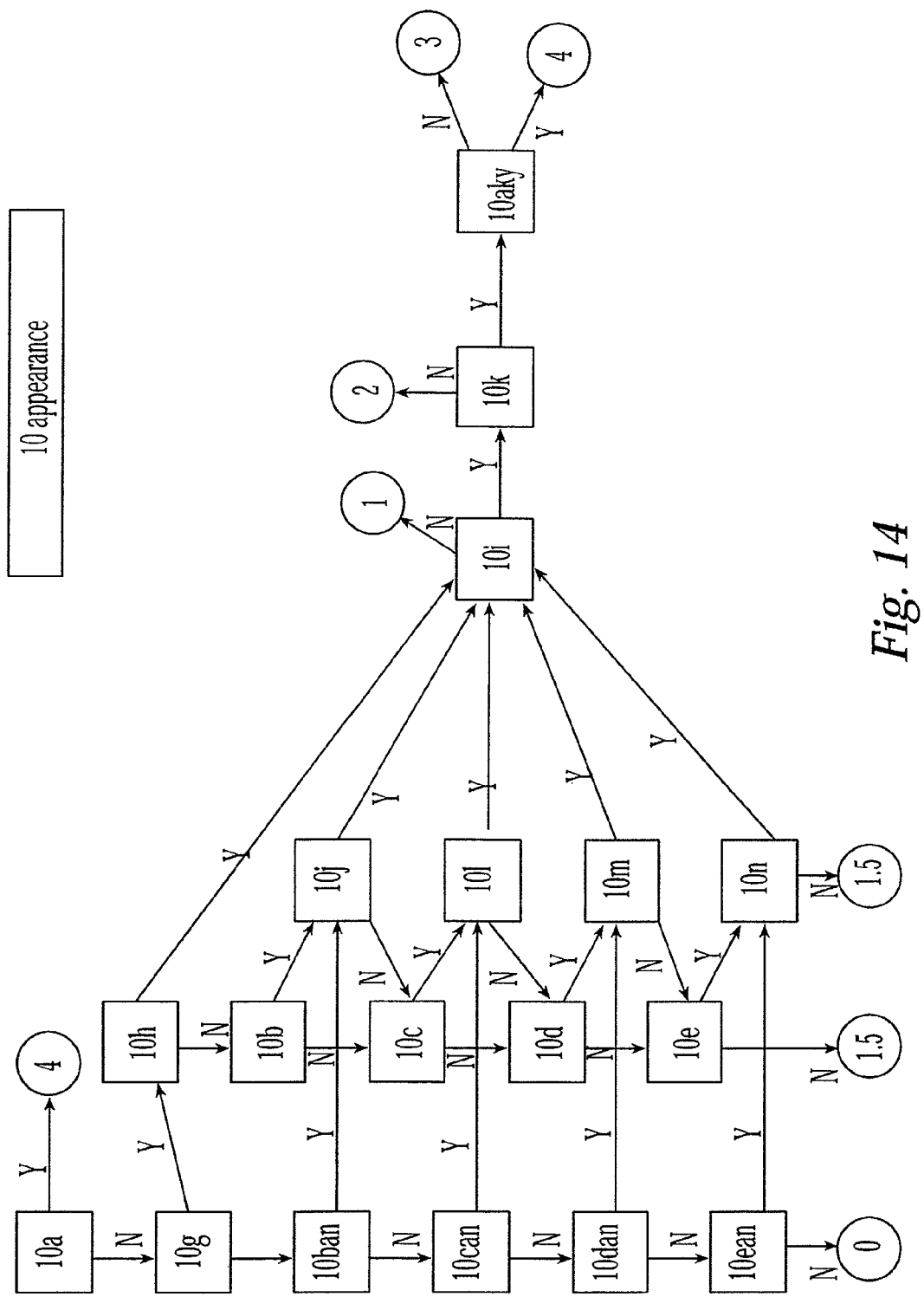
FIG. 14 illustrates a flowchart for a script associated with the YMRS to measure the "appearance" item.
Figure 15:
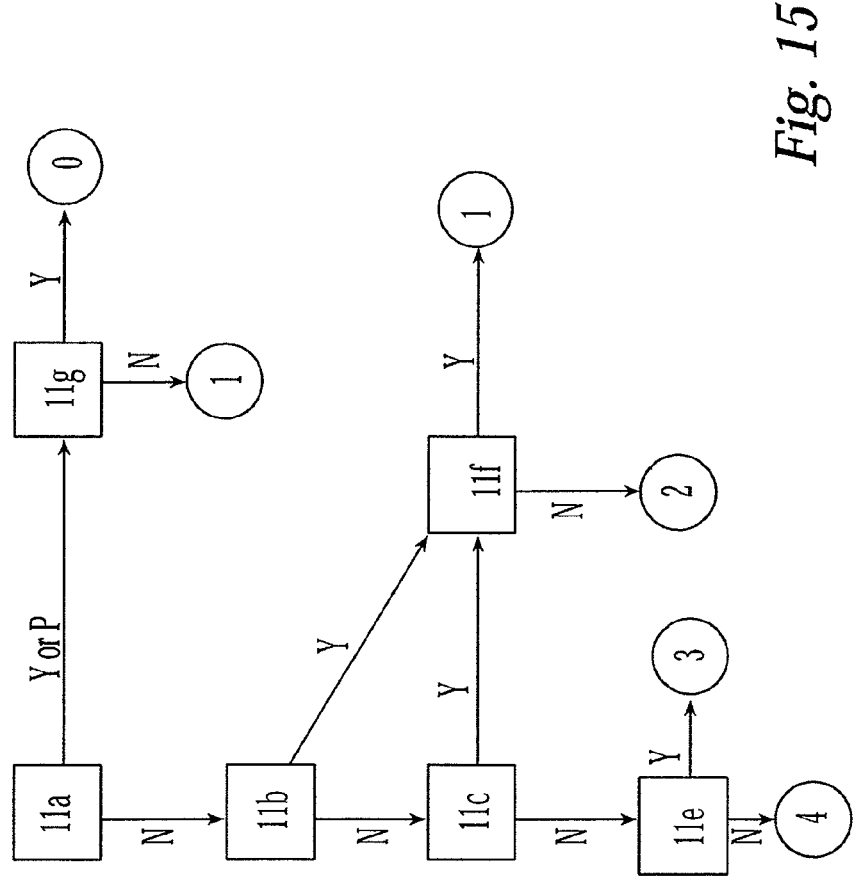
FIG. 15 illustrates a flowchart for a script associated with the YMRS to measure the "insight" item.
Figure 16:
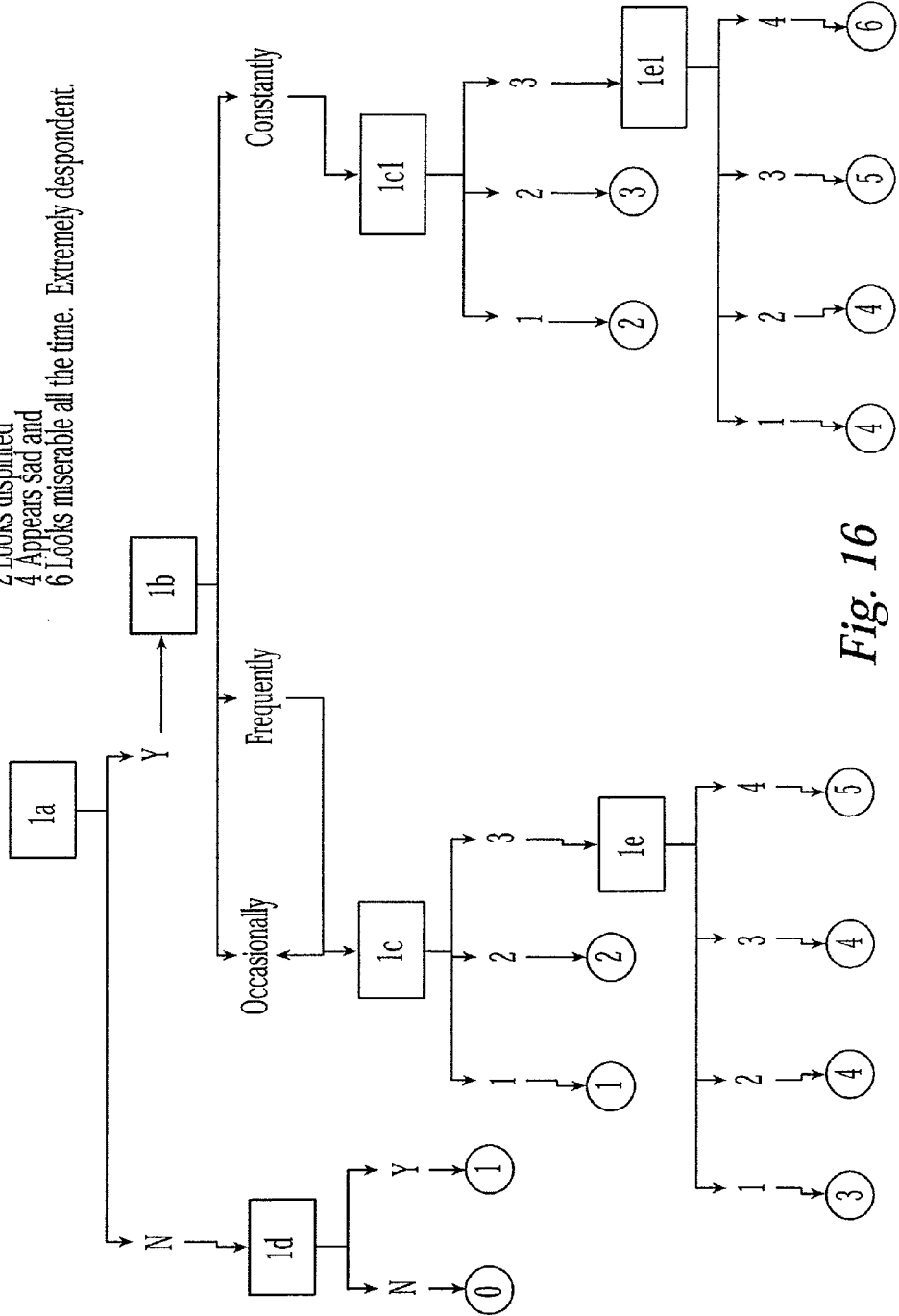
FIG. 16 illustrates a flowchart for a script associated with the MADRS to measure the "apparent sadness" item.
Figure 17:
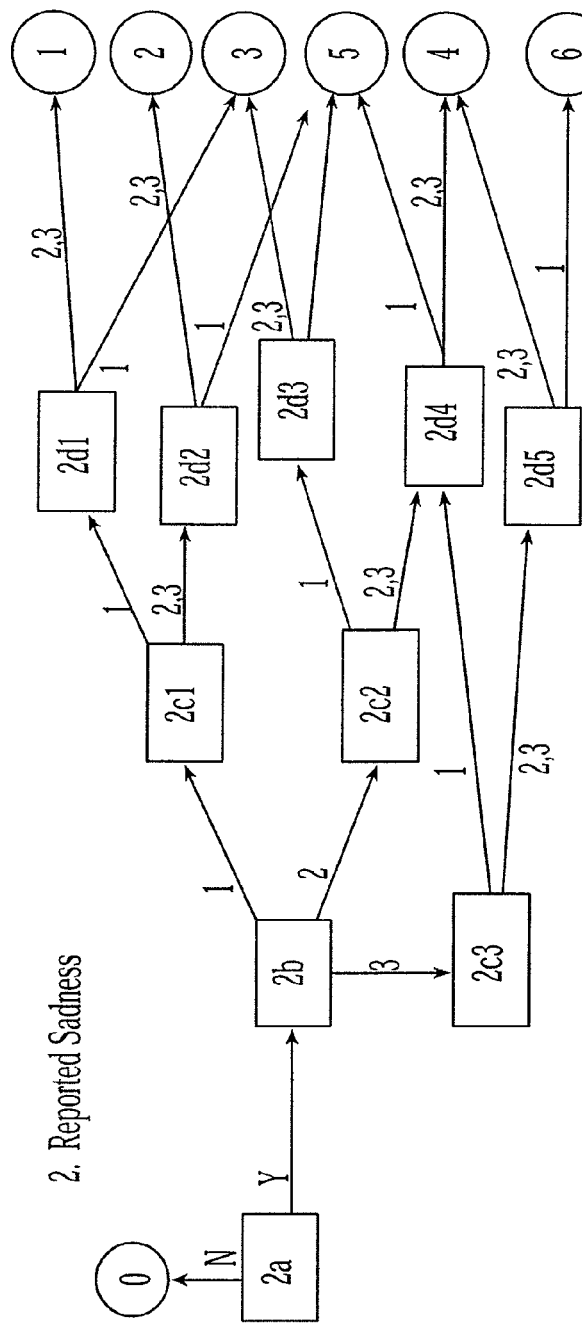
FIG. 17 illustrates a flowchart for a script associated with the MADRS to measure the "reported sadness" item.
Figure 18:
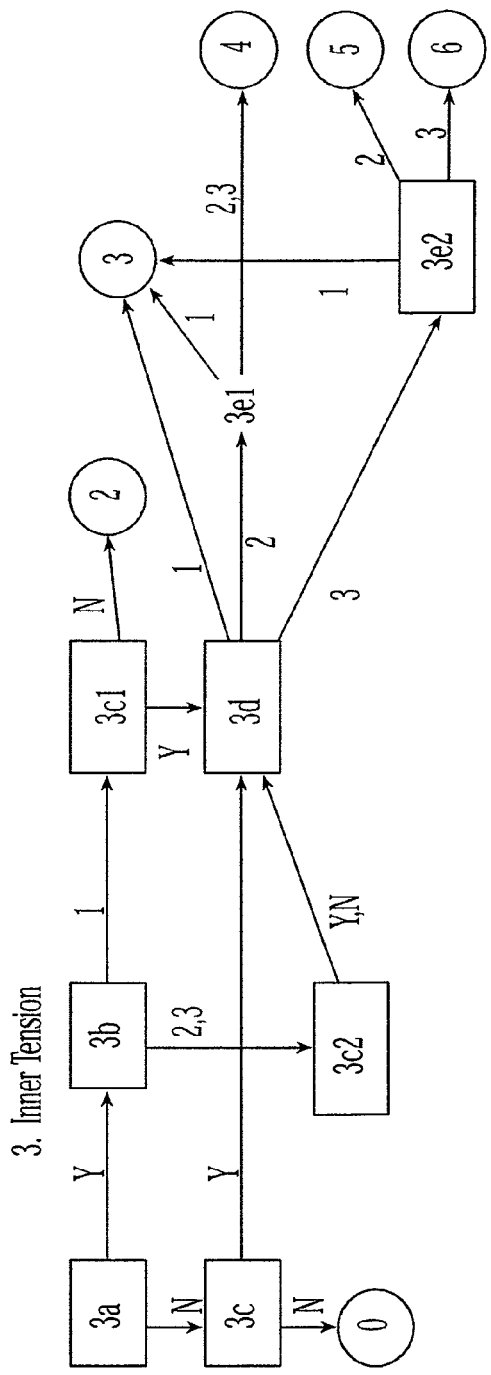
FIG. 18 illustrates a flowchart for a script associated with the MADRS to measure the "inner tension" item.
Figure 19:
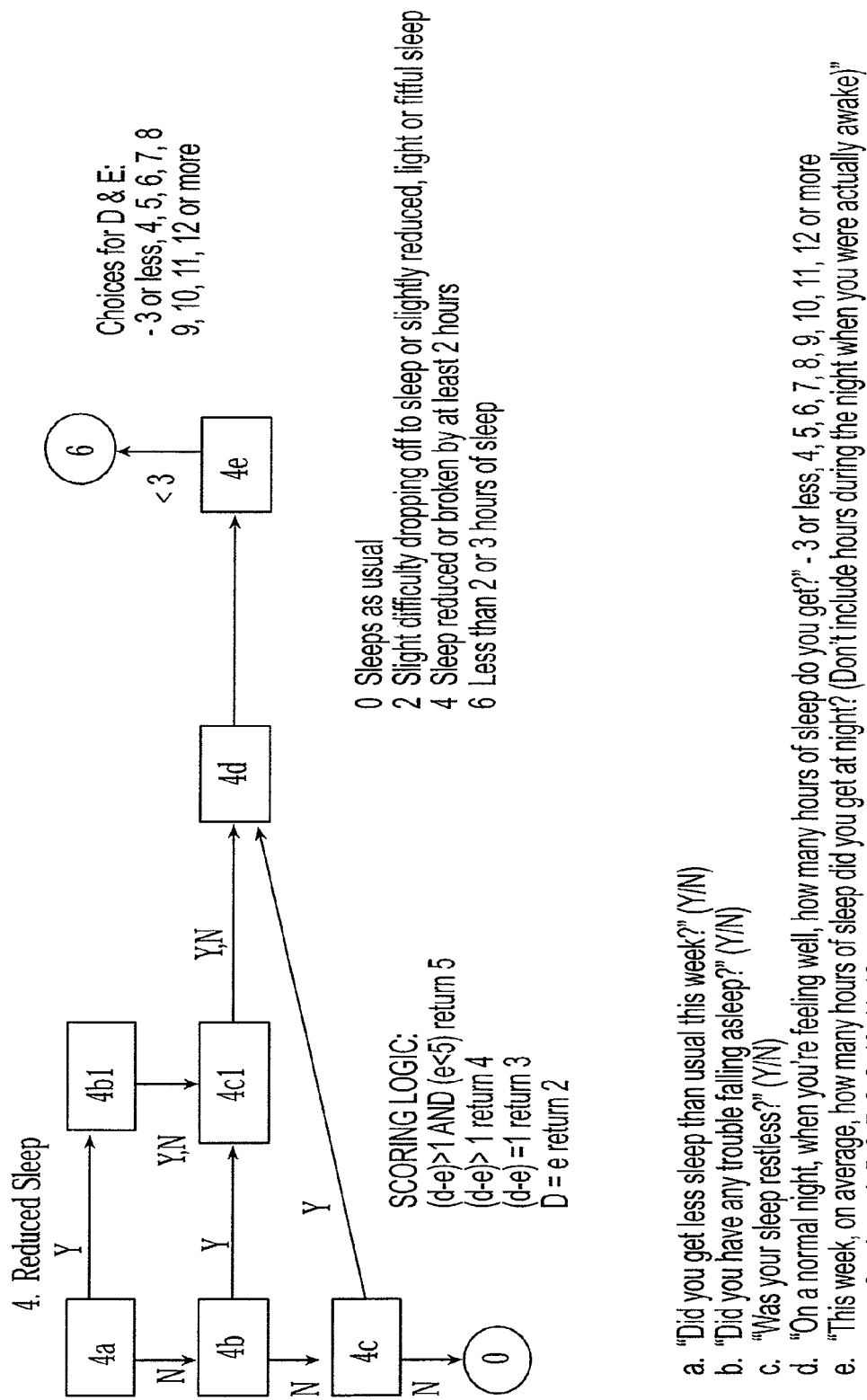
FIG. 19 illustrates a flowchart for a script associated with the MADRS to measure the "reduced sleep" item.
Figure 20:
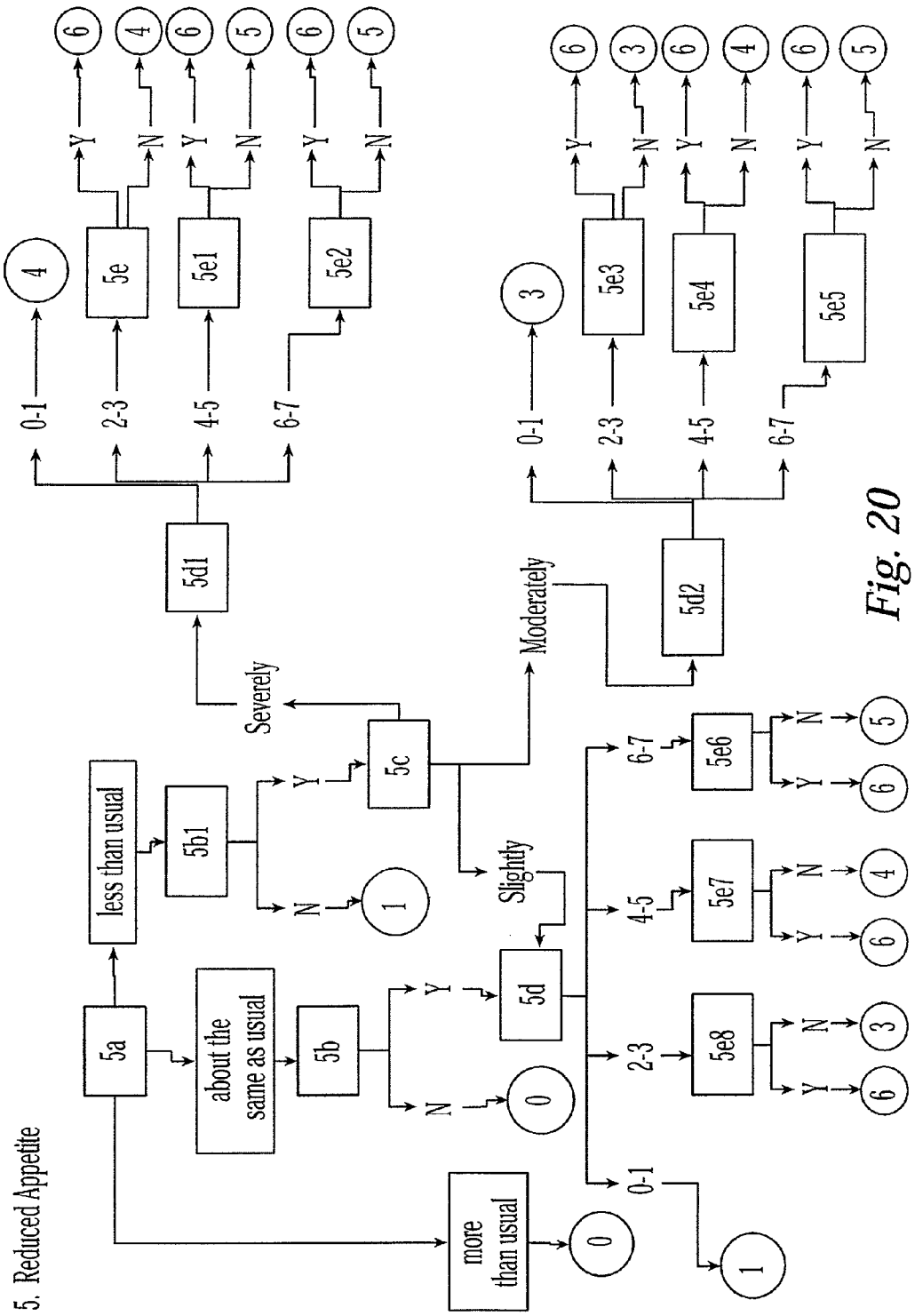
FIG. 20 illustrates a flowchart for a script associated with the MADRS to measure the "reduced appetite" item.
Figure 22:
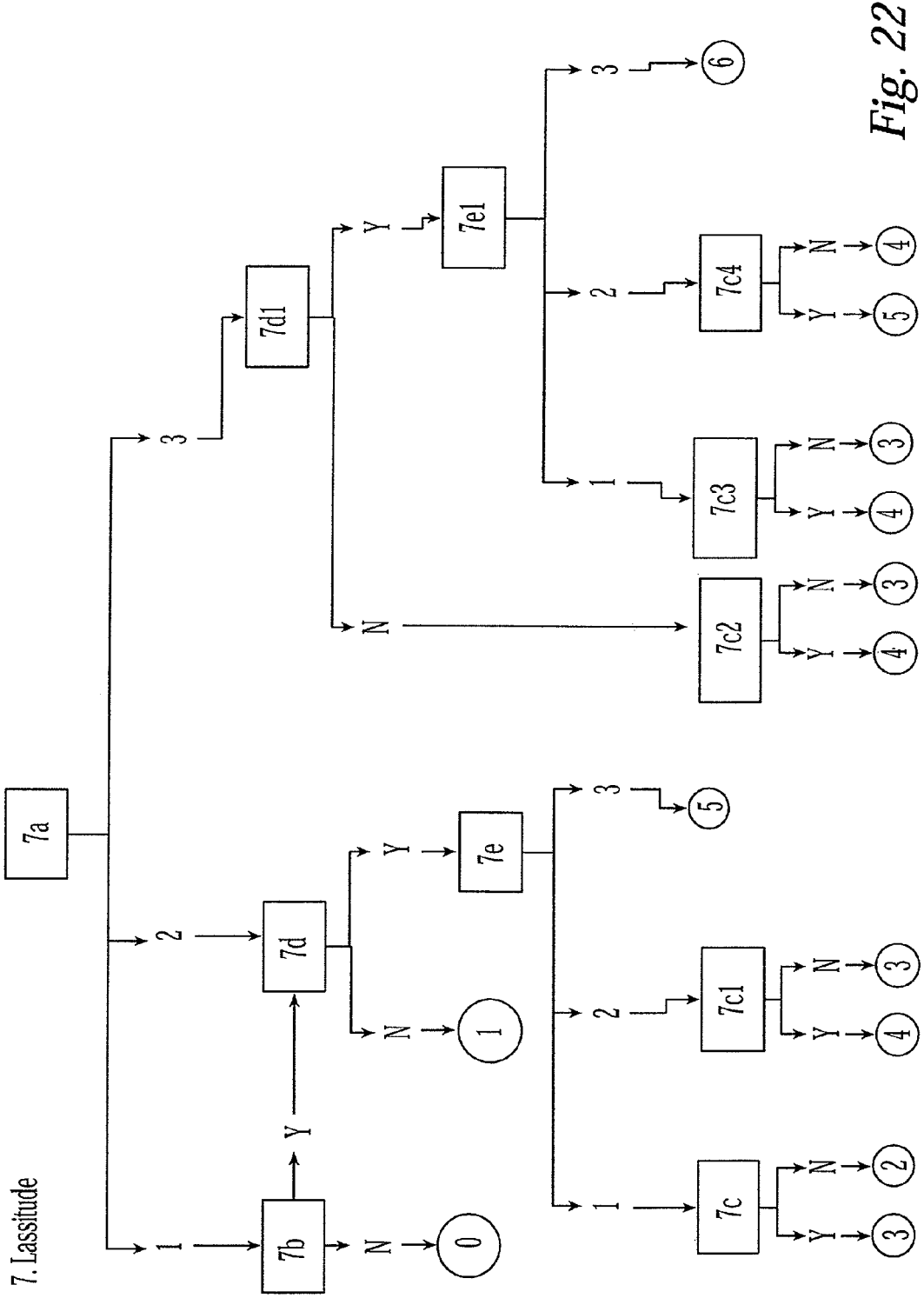
FIG. 22 illustrates a flowchart for a script associated with the MADRS to measure the "lassitude" item.
Figure 23:
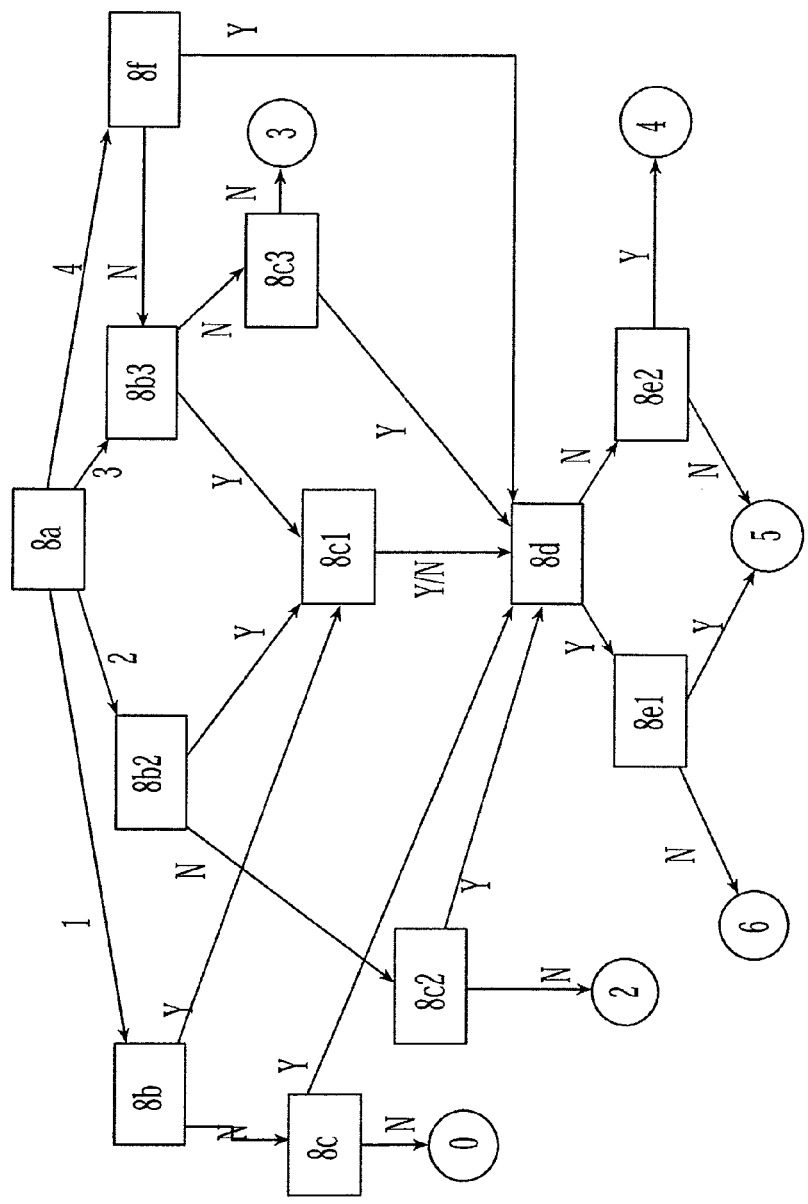
FIG. 23 illustrates a flowchart for a script associated with the MADRS to measure the "inability to feel" item.
Figure 24:
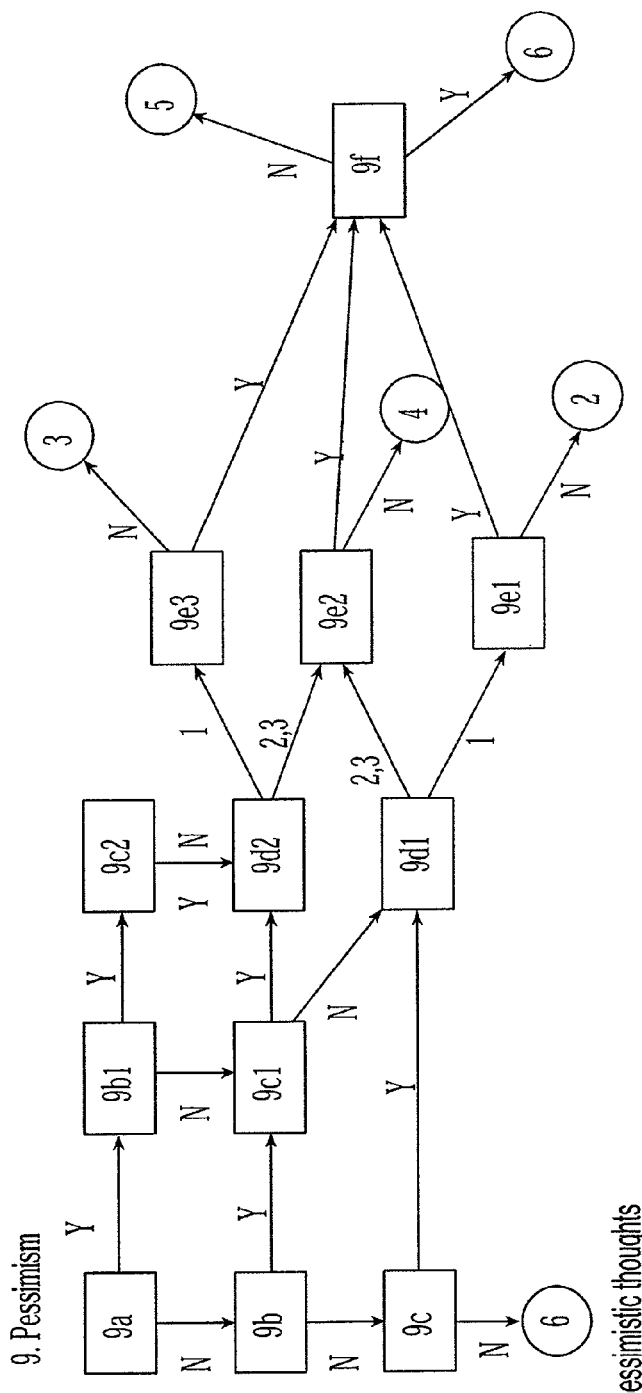
FIG. 24 illustrates a flowchart for a script associated with the MADRS to measure the "pessimism" item.
Figure 25:
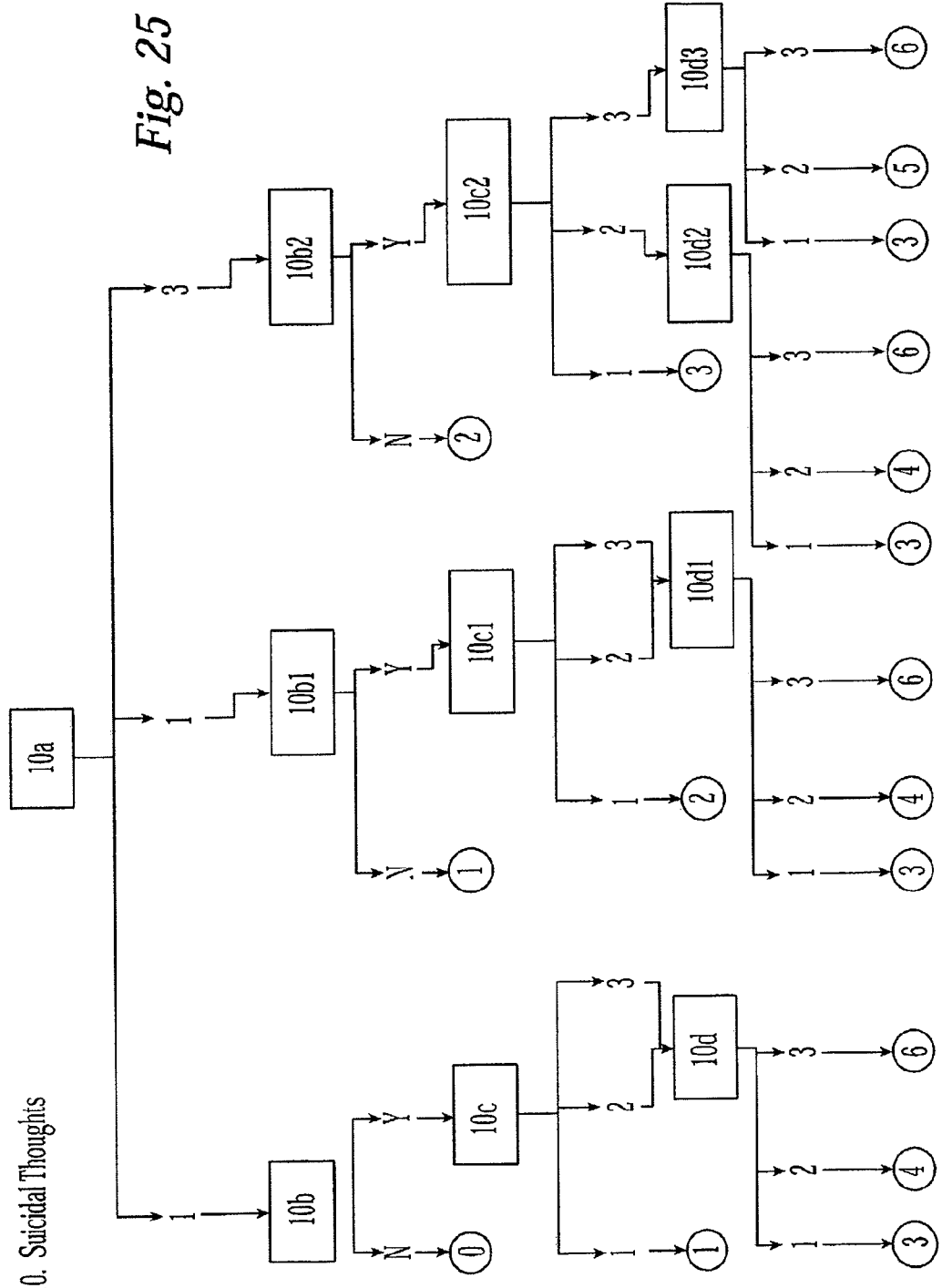
FIG. 25 illustrates a flowchart for a script associated with the MADRS to measure the "suicidal thoughts" item.
Figure 26:
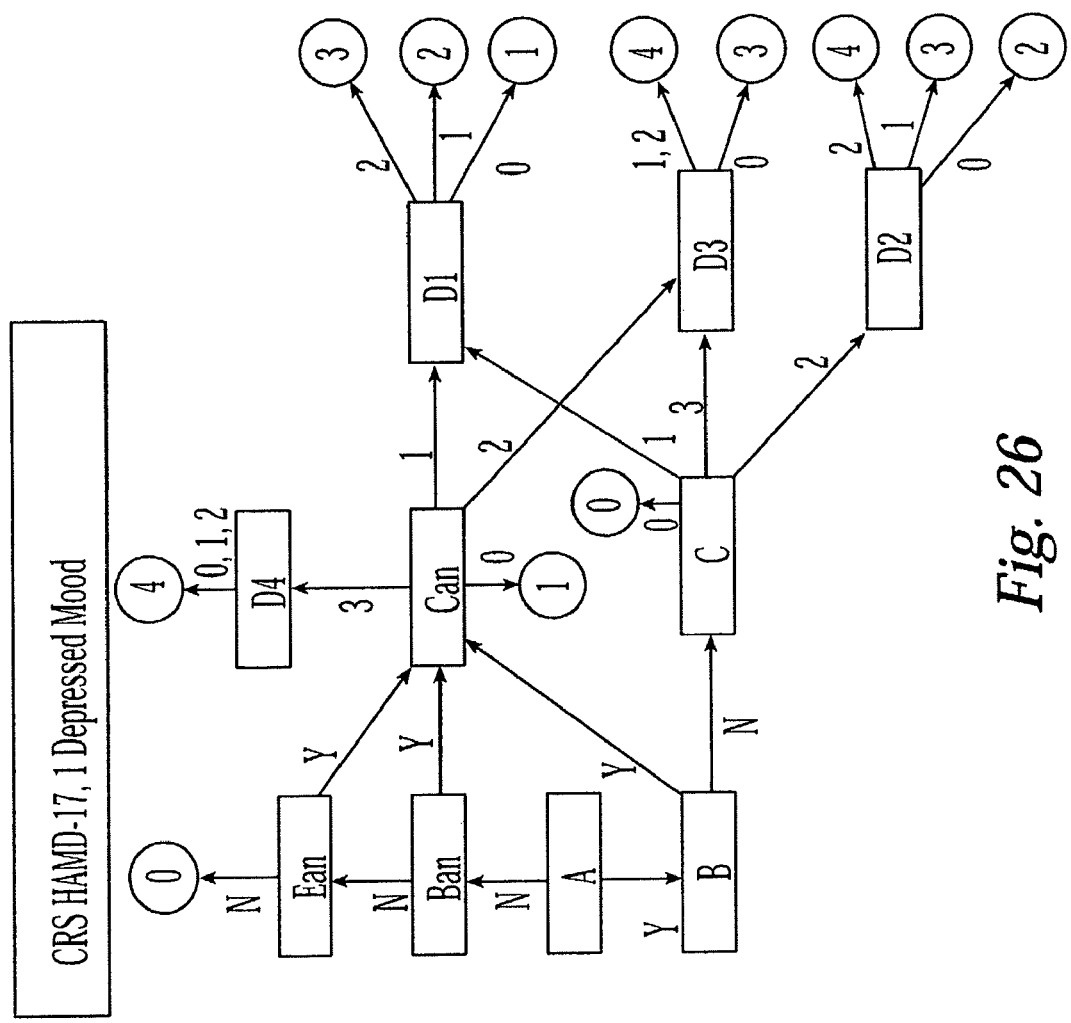
FIG. 26 illustrates a flowchart for a script associated with the HAMD to measure the "depressed mood" item.
Figure 27:
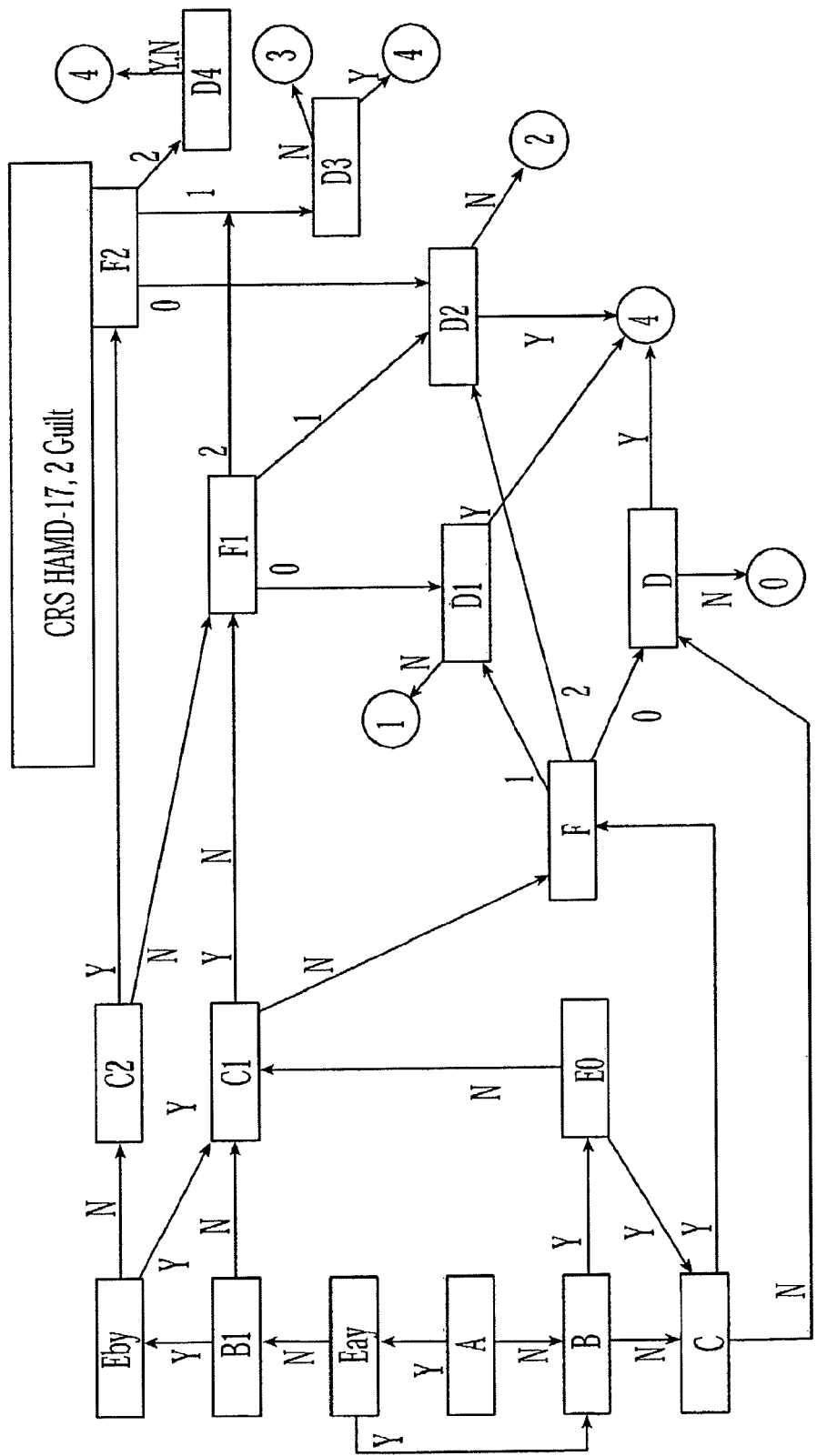
FIG. 27 illustrates a flowchart for a script associated with the HAMD to measure the "guilt" item.
Figure 28:
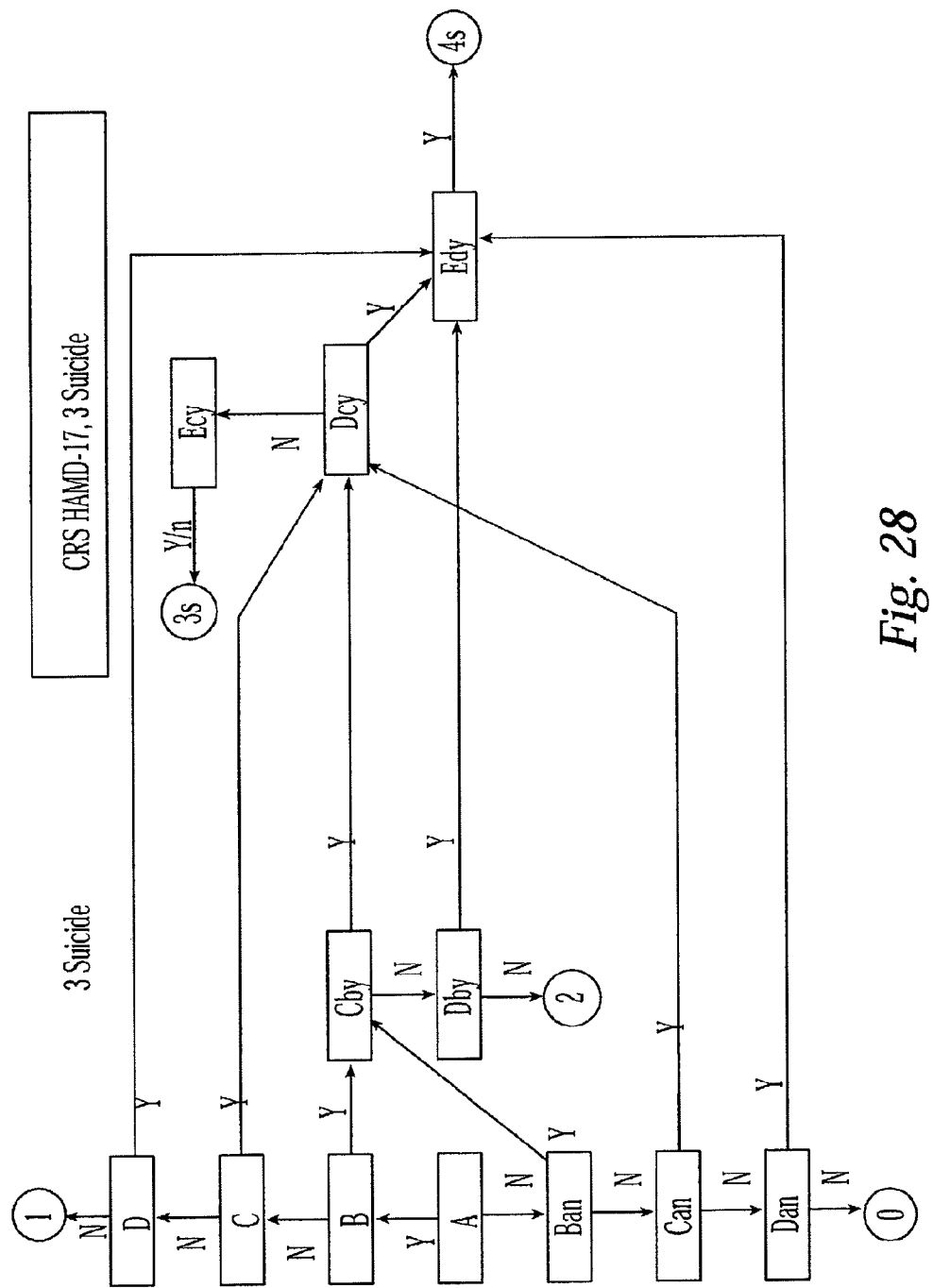
FIG. 28 illustrates a flowchart for a script associated with the HAMD to measure the "suicide" item.
Figure 29:
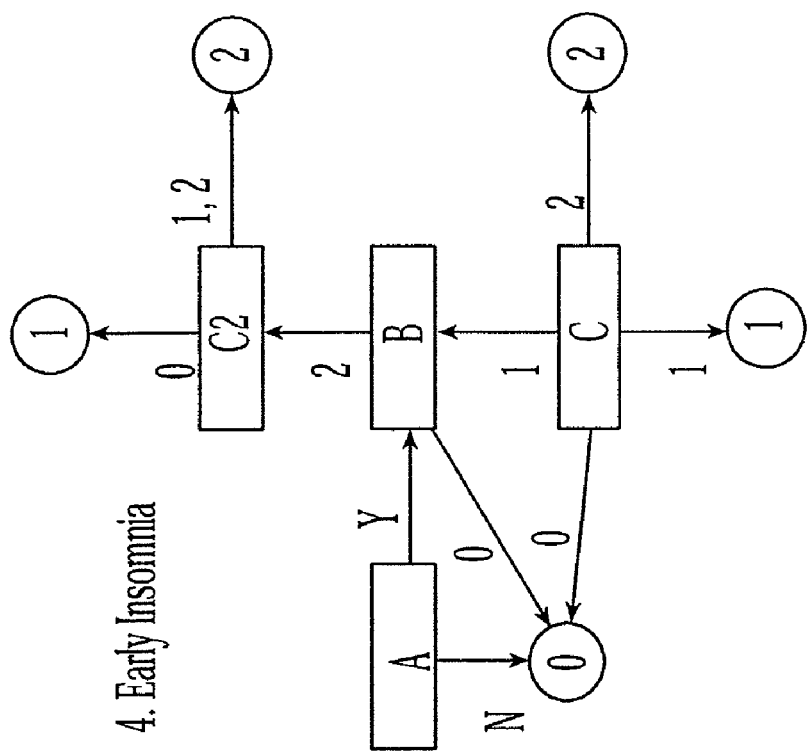
FIG. 29 illustrates a flowchart for a script associated with the HAMD to measure the "early insomnia" item.
Figure 30:
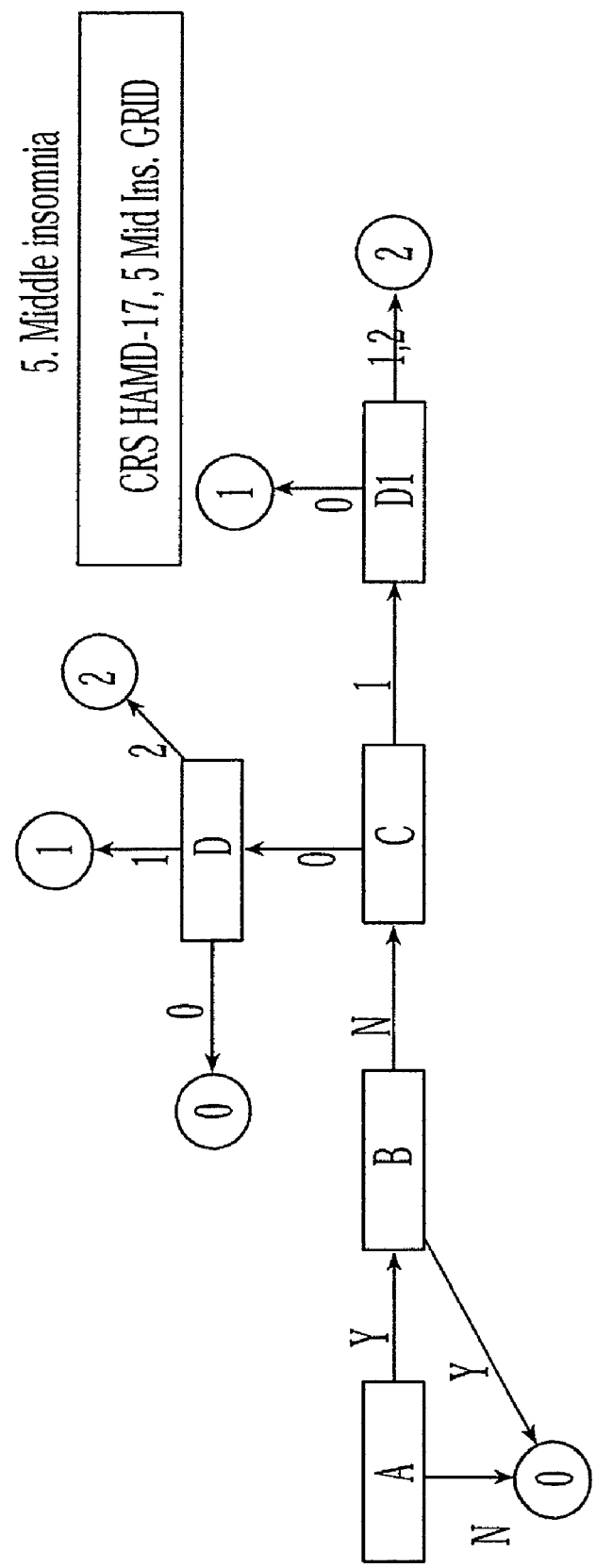
FIG. 30 illustrates a flowchart for a script associated with the HAMD to measure the "middle insomnia" item.
Figure 31:
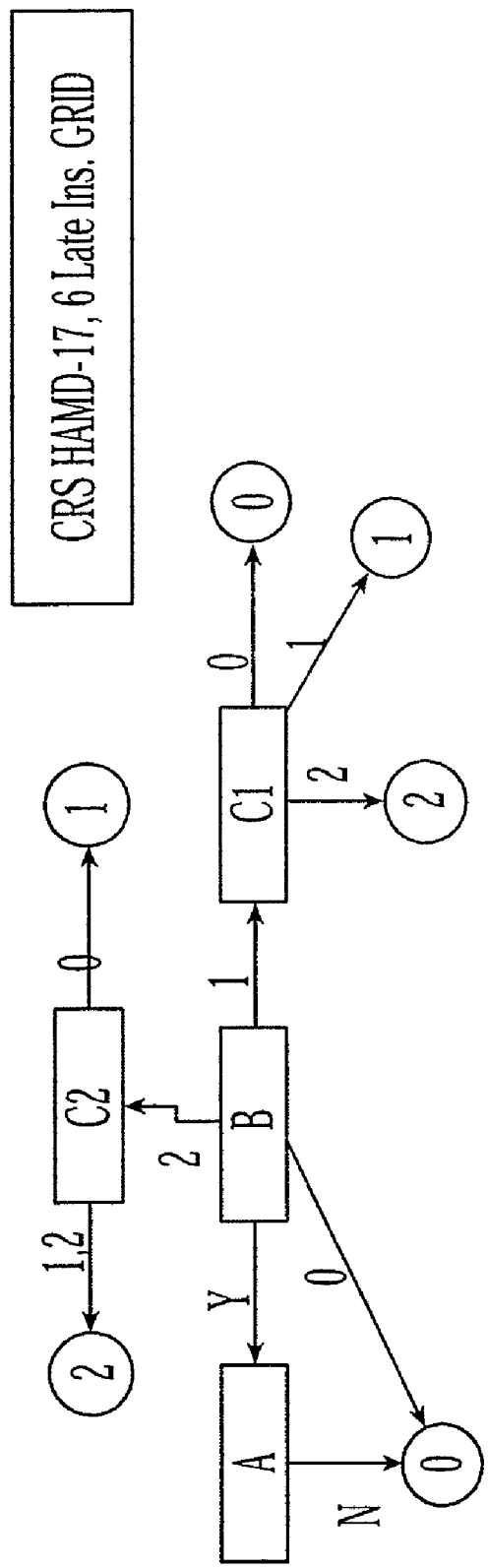
FIG. 31 illustrates a flowchart for a script associated with the HAMD to measure the "late insomnia" item.
Figure 32:
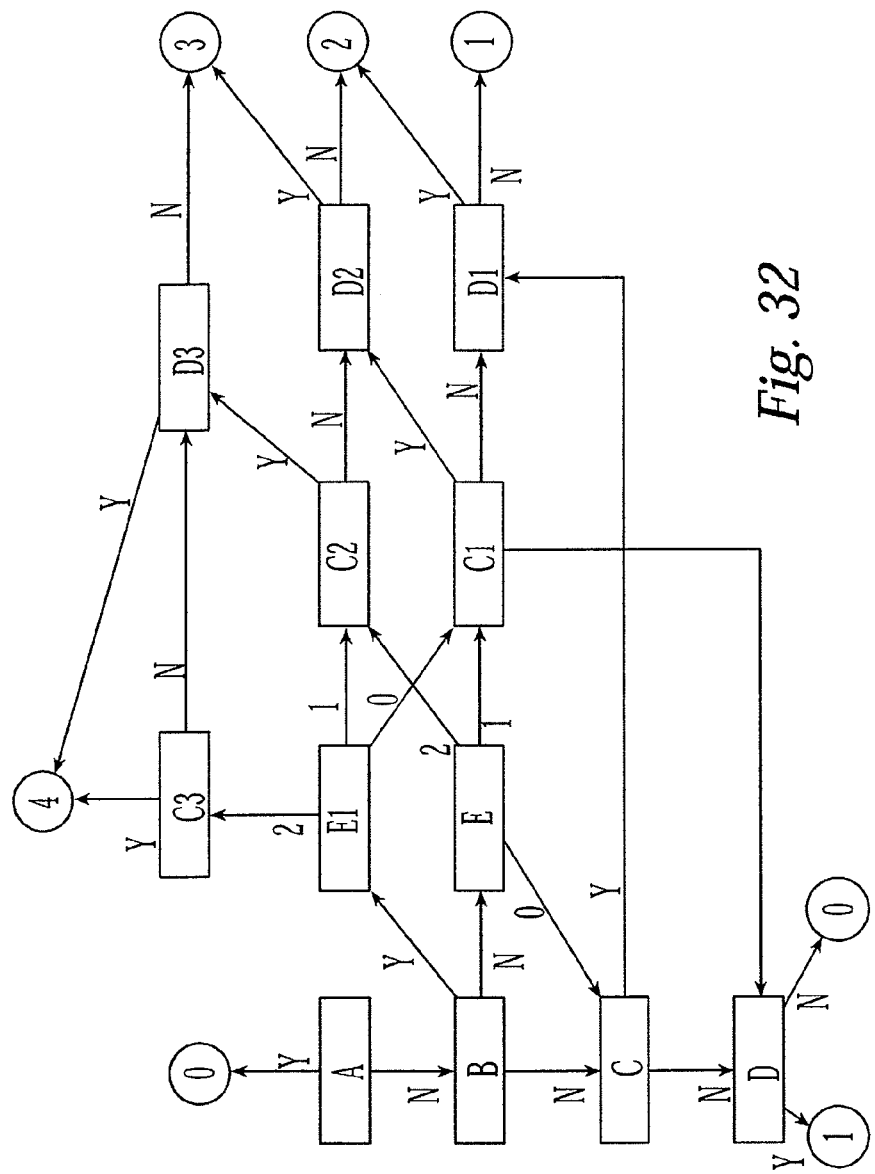
FIG. 32 illustrates a flowchart for a script associated with the HAMD to measure the "work activities" item.
Figure 33:
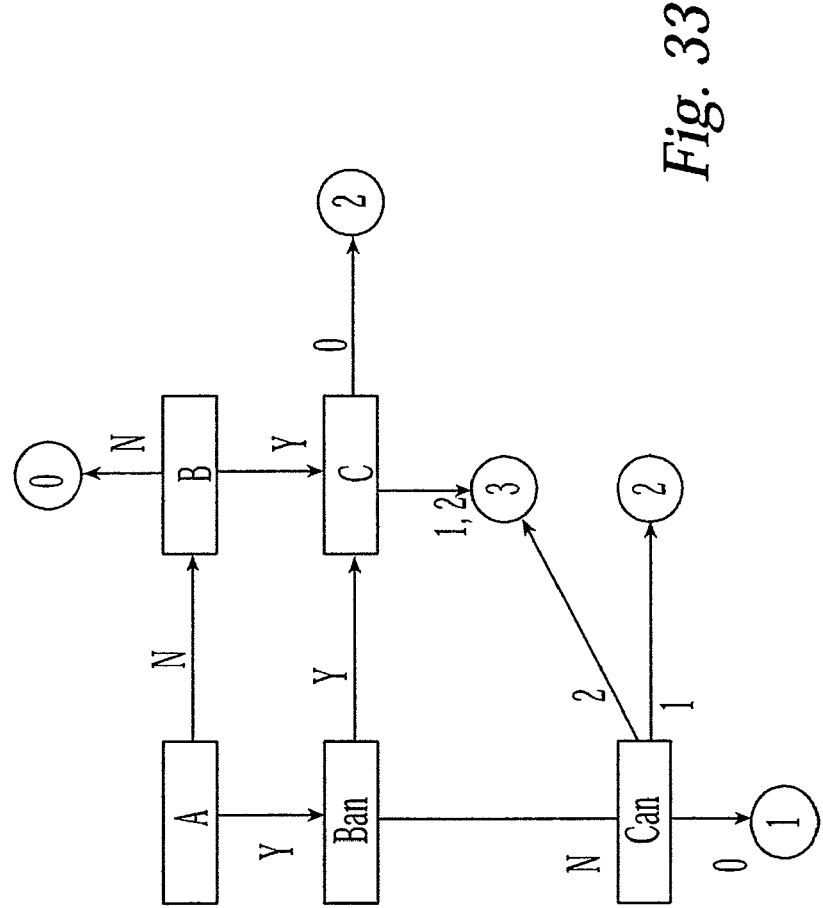
FIG. 33 illustrates a flowchart for a script associated with the HAMD to measure the "retardation" item.
Figure 34:
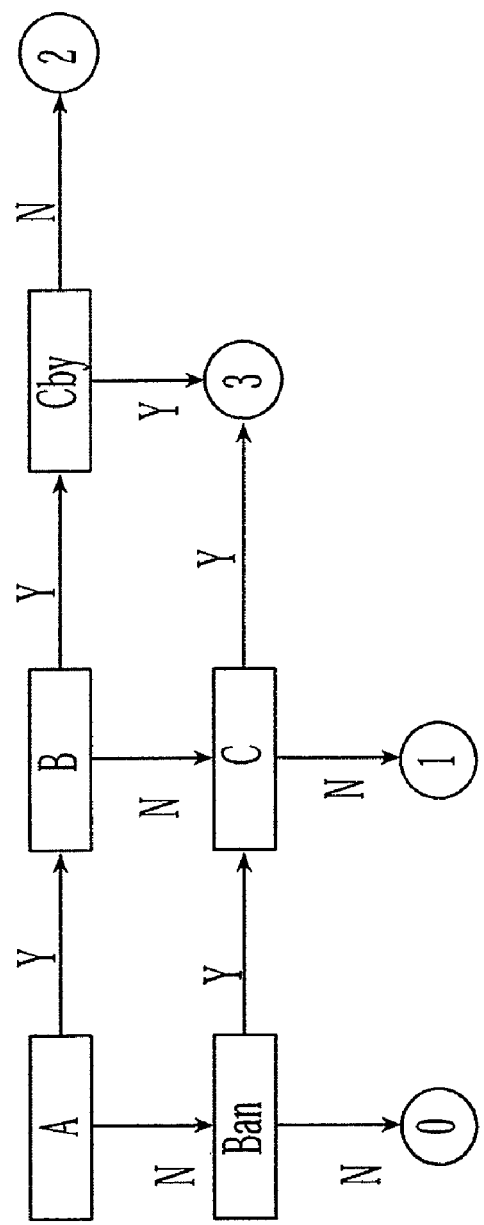
FIG. 34 illustrates a flowchart for a script associated with the HAMD to measure the "agitation" item.
Figure 35:
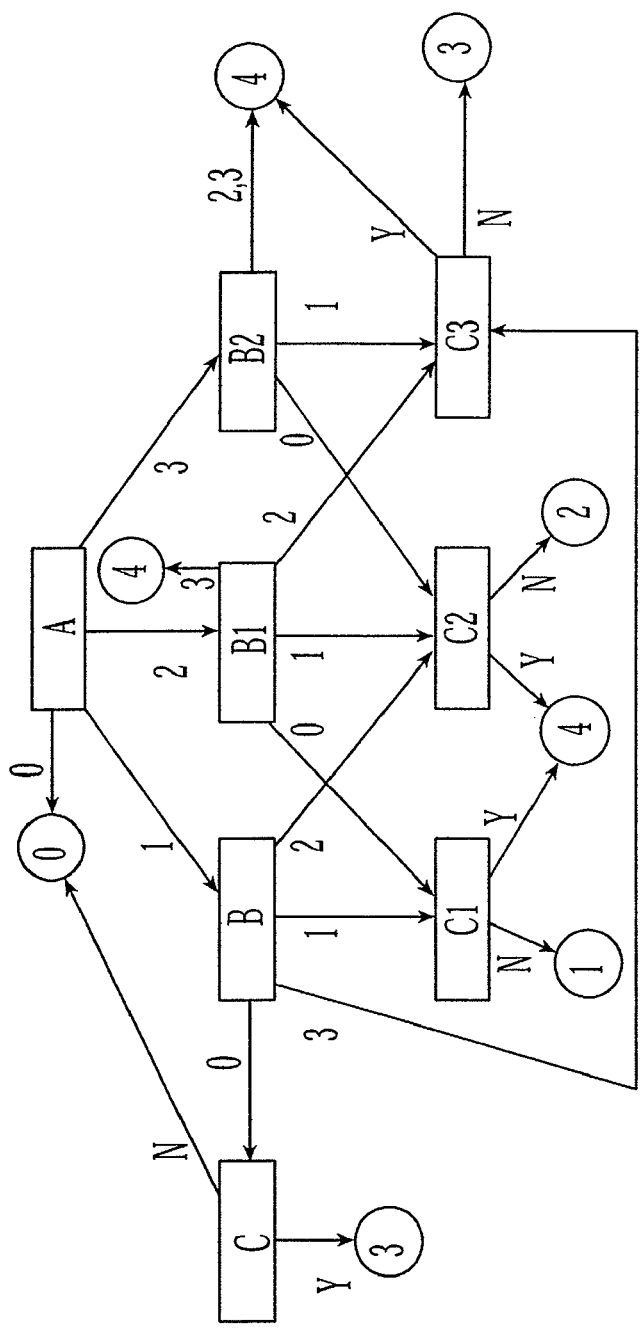
FIG. 35 illustrates a flowchart for a script associated with the HAMD to measure the "anxiety psychic (G/S)" item.
Figure 36:
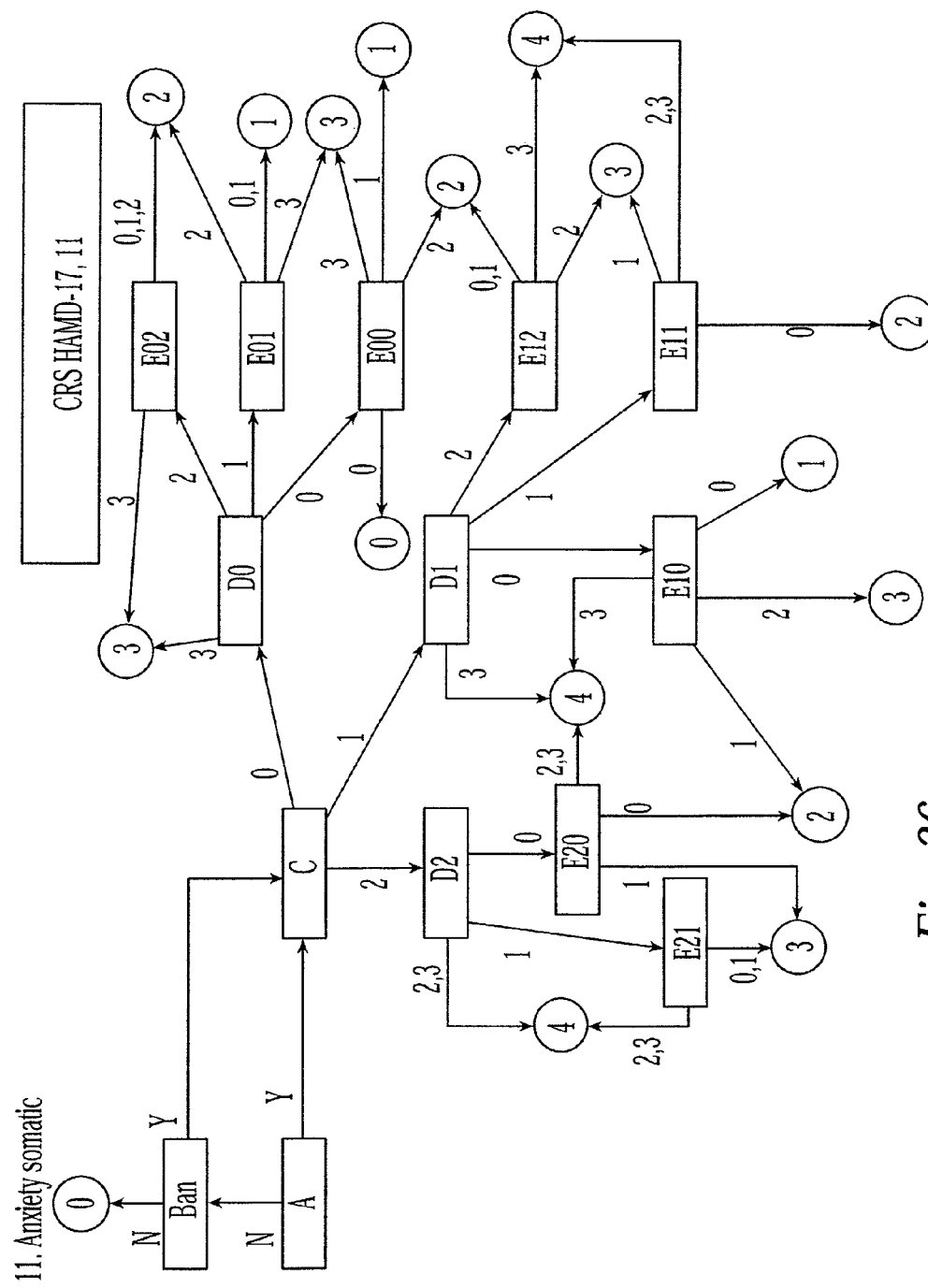
FIG. 36 illustrates a flowchart for a script associated with the HAMD to measure the "anxiety somatic" item.
Figure 37:
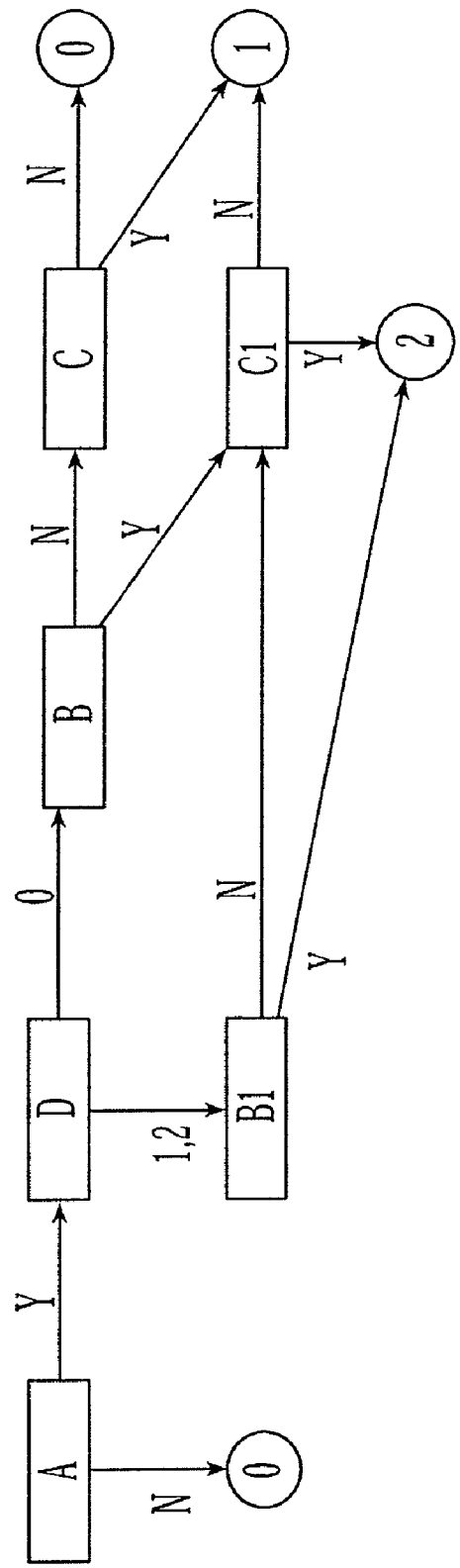
FIG. 37 illustrates a flowchart for a script associated with the HAMD to measure the "appetite" item.
Figure 38:
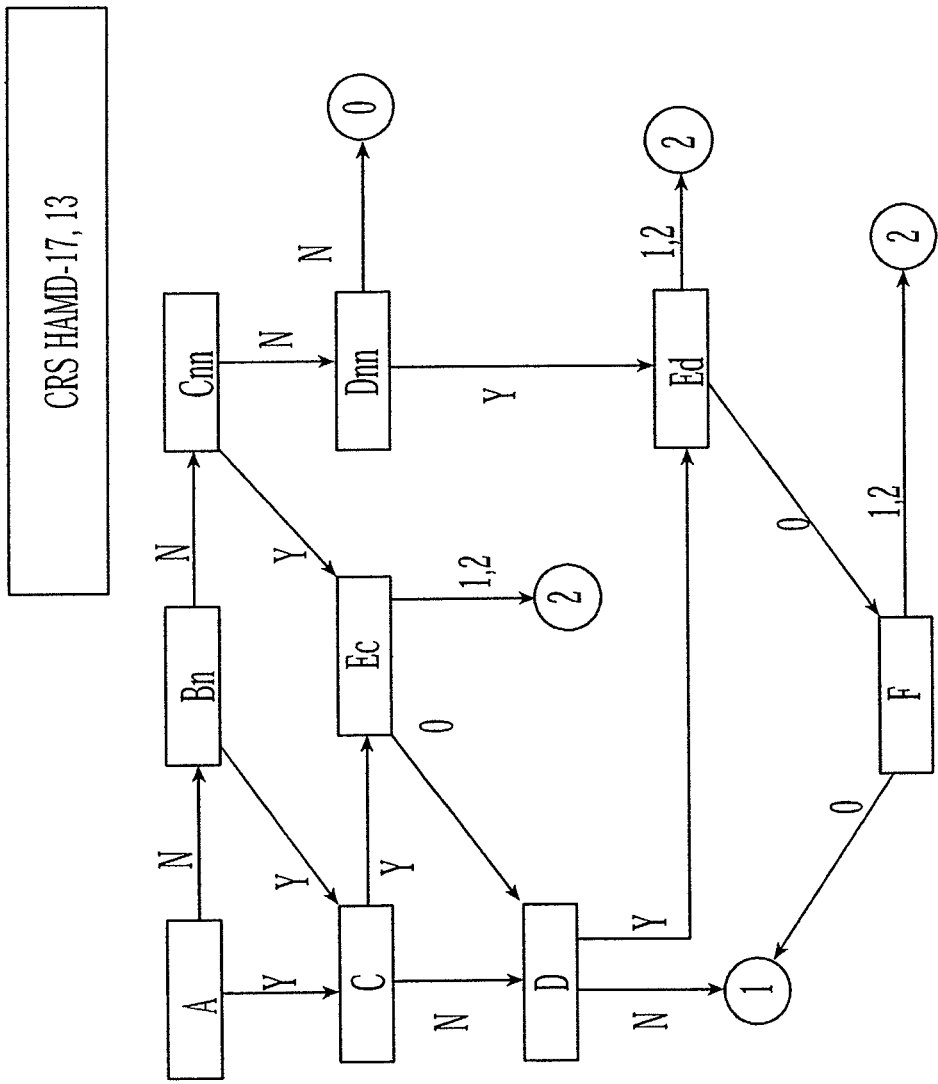
FIG. 38 illustrates a flowchart for a script associated with the HAMD to measure the "somatic symptoms" item.
Figure 39:
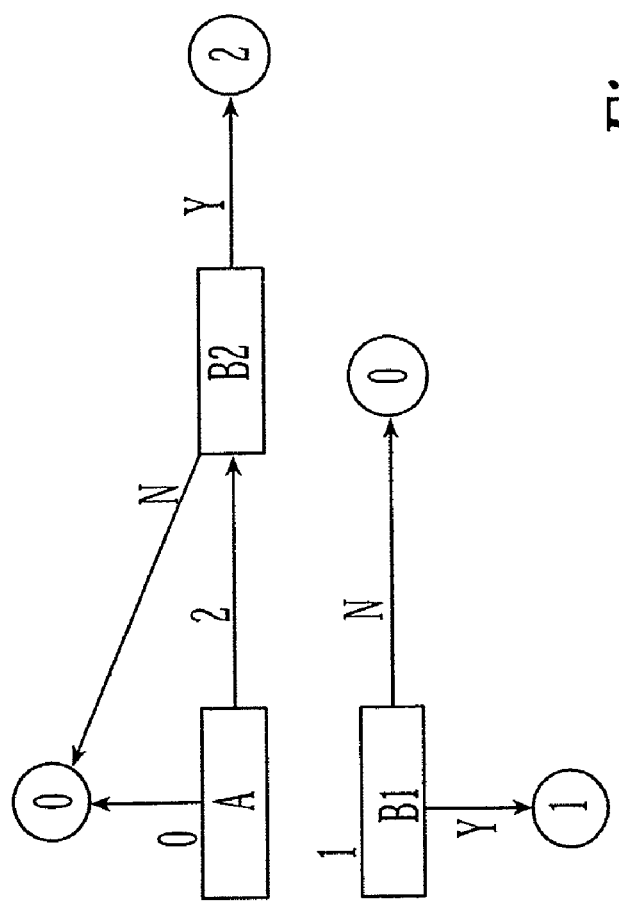
FIG. 39 illustrates a flowchart for a script associated with the HAMD to measure the "sexual interest" item.
Figure 40:
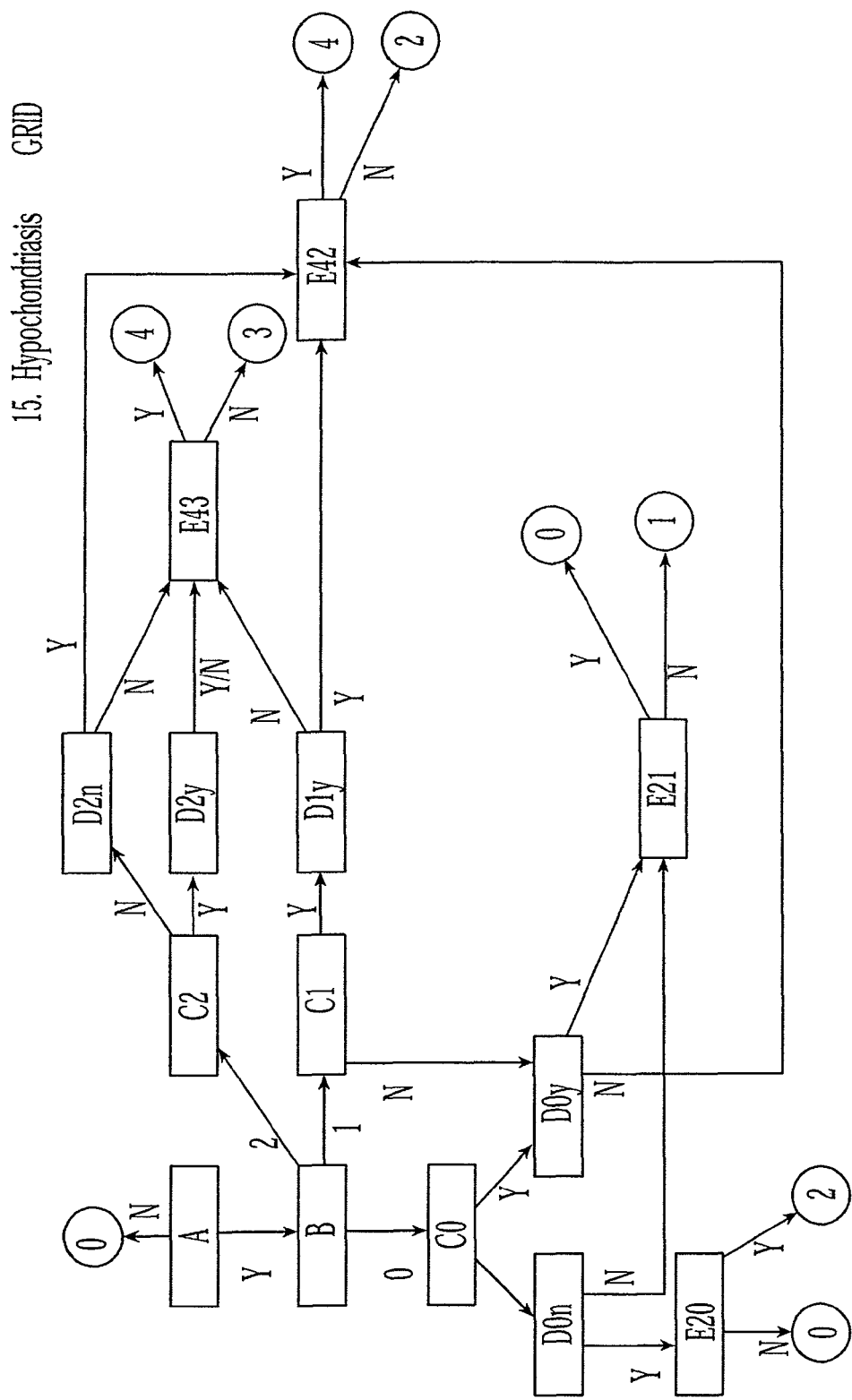
FIG. 40 illustrates a flowchart for a script associated with the HAMD to measure the "hypochondriasis GRID" item.
Figure 41:
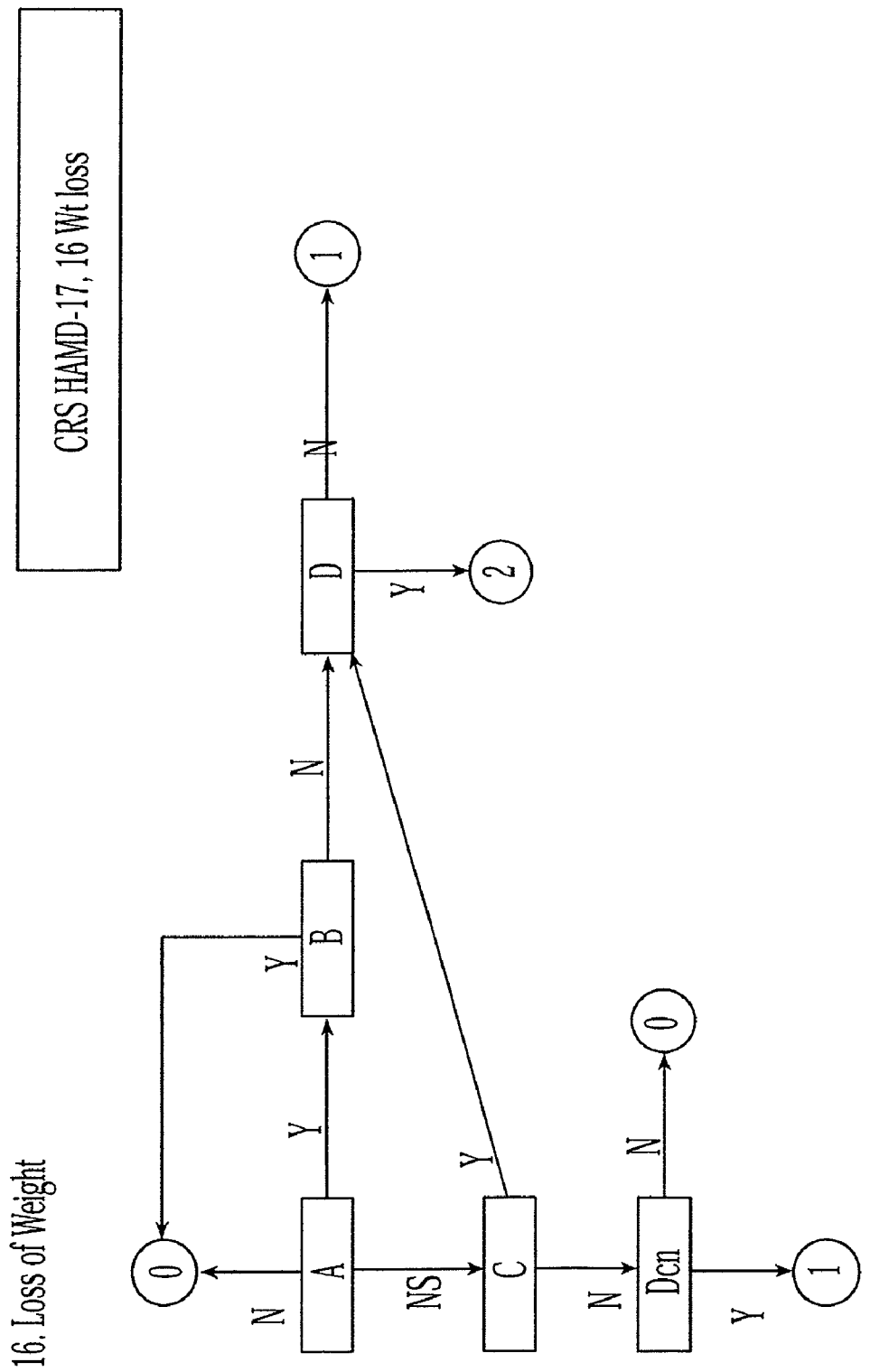
FIG. 41 illustrates a flowchart for a script associated with the HAMD to measure the "weight loss" item.
Figure 42:
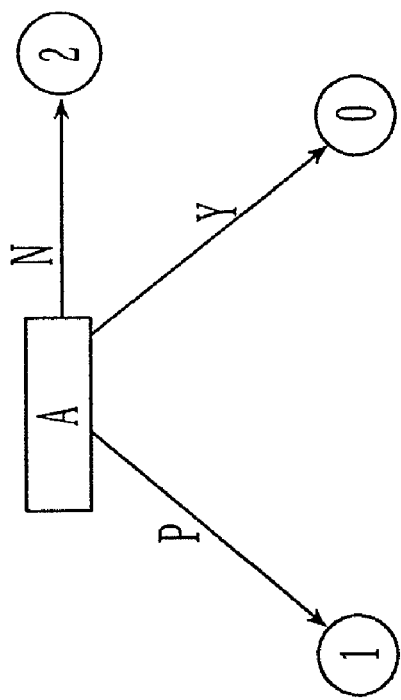
FIG. 42 illustrates a flowchart for a script associated with the HAMD to measure the "insight" item.

In the YMRS set of question in APPENDIX A1, item I lists the various questions referenced in the YMRS Mood item scoring script illustrated in FIG. 5. The squares correspond to question prompts, and the lines connecting squares correspond to responses from the patient. Thus the square 1a corresponds to the question 1a, which is listed under item I in APPENDIX A1 as "This past week were there any times when even briefly you were feeling optimistic about the future, or just in a really good mood?" If the patient responds "yes," then the patient is next prompted with question 1e, and if the patient responds "no," then the patient is next prompted with question 1b. If a response leads to a circle in the diagram, the circle contains the score for that item. Thus, if after responding "yes" to question 1a, the patient responds "yes" to question 1e, no more prompts are administered for the Mood item, and the Mood item is scored 4. It should be noted that since the scoring is influenced by the location of a question due to previous answers, different instances of the same question are distinguished from each other. For example, question 1g is the same question as question 1gn but in a different path of the ICI flowchart. In other words, the suffix of question 1g identifies a location for question 1g in the ICI flowchart. This choice of prefixes, suffixes, or questions is illustrative only and should not be interpreted as limiting the scope of the claimed invention to the exemplified scheme.

The use of scripts also results in a particular subject being presented with fewer questions than if the questions were administered using a printed form. This advantage is illustrated, for instance, in the script illustrated in FIG. 5. Following administration of question 1a, if the subject responds with a Y question 1e is presented next. If the subject then responds with another Y, then the script terminates with the subject being successfully being rated with a score of 4 for item MOOD of YMRS. The subject is also, optionally, spared an encounter with questions 1b, 1c, 1d, 1f, 1g, 1h, or 1i.

In a manner similar to that described for YMRS in the description above, additional ICI scripts are illustrated for the MADRS and the HAMD scales. For the MADRS scale, APPENDIX A2 presents questions for items I through X. Each of this items corresponds to the script flowcharts illustrated in FIGS. 16-25, respectively. APPENDIX A3 presents items I through the XVII of the HAMD scale, while corresponding scripts are shown in FIGS. 26-42. Additional as well as alternative scripts may be used to automate the administration of a scale of choice. For each item in the scale that is scored, the script preferably presents a set of questions that end with determining the score for the item. While the answer to a question in the script determines the next question, this should not be interpreted as requiring that for each answer to a particular question in the script there is one and only one next question. For instance, in FIG. 12, both acceptable answers to question 8a result in question, 8b being posed next.

Turning to administration of a script in a study, the study subjects are preferably entered into the system after an introduction to the hardware and assistance with the completion of an online introduction and registration procedure, as soon as the local site study coordinator believes that the subject is able.

Subjects are preferably asked to complete a baseline ICI immediately following their last inpatient rating and/or their first outpatient visit. After administration by a human rater of the clinical rating (e.g., the Young Mania Rating Scale), study staff enter the subject's study ID number, date and ratings into the computer. Subjects are then given access to a computer implementing the ICI. A staff person preferably starts the system, and asks the subject to complete the computerized interview. While the subject completes the interview, staff preferably remain available to answer questions about completing the interview.

During study visits (including follow-up visits), subjects may once again be evaluated according to the clinical protocol and an ICI may again be administered. Such an ICI may be either an abbreviated ICI asking the patient a plurality of questions, e.g., 5-7 questions about their health status during the preceding week (e.g., physical pain, missed medication, most hours slept, least hours slept, and their weight) or a full ICI reviewing items on the ratings scales (e.g. YMRS), and preferably a plurality of questions, e.g., six general health questions and three care satisfaction questions. A random test may be conducted to determine whether an abbreviated ICI or a full ICI is administered.

When a subject completes the ICI, the coordinator or their designate preferably completes an online ICI checklist that requests entry of scores for each item on the ratings scales (e.g. YMRS). If a subject refuses the ICI, the local site coordinator, or their designate, will complete an online ICI checklist and an online ICI refusal form.

The system uses a comparison program to generate a report of the concordance between the results of the ICI and live interview. This report is preferably sent to one or more of the study sponsor, local site principal investigator, and a system principal investigator. When the report indicates that concordance is below acceptable levels, a remediation call is made to the rater, and the system adjusts the randomization schedule such that a full ICI is obtained at both the next visit conducted by that rater and the next visit made by that subject.

At the time of the final study visit, subjects are assessed according to the clinical protocol. Subsequently, subjects are administered an ICI and preferably asked a plurality of questions, e.g., 5 multiple choice questions comparing the ICI to live interviews (e.g. Compared with your interview with Dr XYZ, this interview was: A) Harder to understand, B) Easier to Understand, C) About the same).

Figure 4:
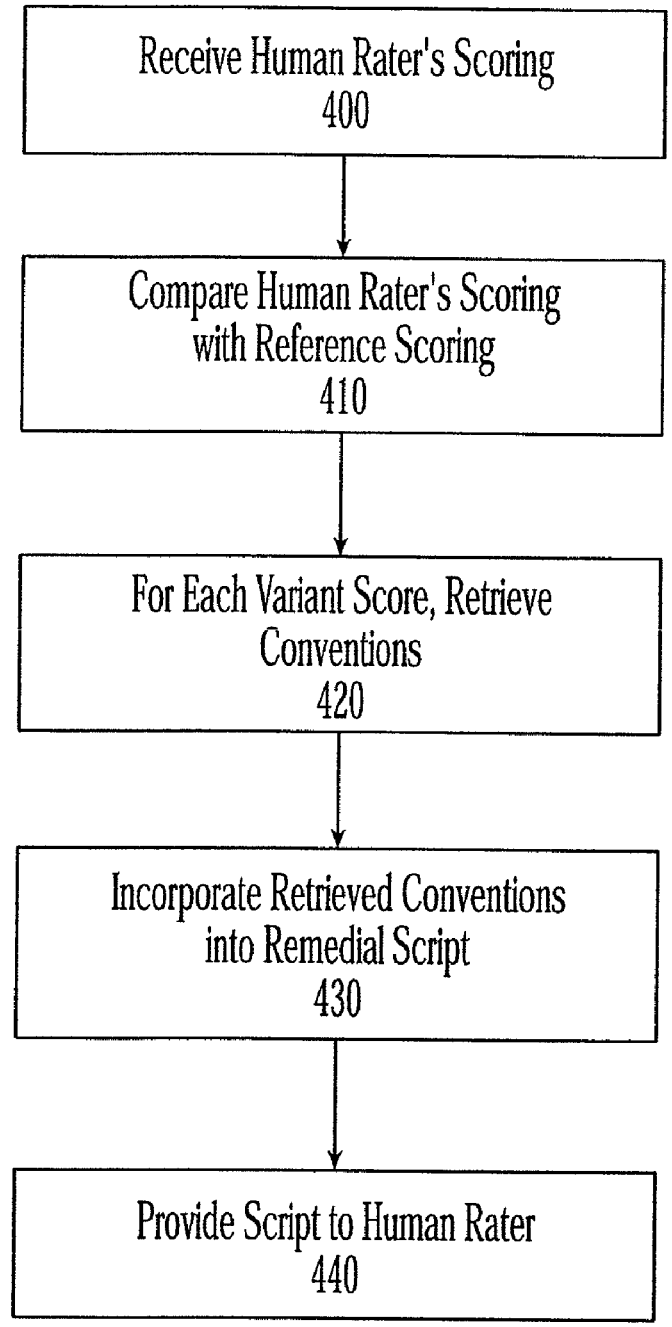
FIG. 4 schematically depicts an example of a preferred embodiment of the invention for rater remediation.

In another aspect, the invention comprises a system for providing remedial training for human raters. As schematically illustrated in FIG. 4, the system receives, during step 400, the human rater's scoring of a subject or set of training interviews. Next, during step 410, the system then compares the rater's scoring with reference scoring of the same subject or training interviews, such as computerized scoring, consensus scoring, or expert scoring. For each score (e.g. Mood on YMRS) that differs significantly from the reference scores, during step 420, the system retrieves scoring conventions from previously stored scoring conventions. The scoring conventions may comprise text, audio, video, multimedia or other explanatory material indicating how the reference score was derived from the subject interview. Next, during step 430, the scoring conventions are incorporated into remedial script, which is then, during step 440, provided to human rater 440. The remedial script may be a script or semi-script for a human expert, or a computerized training program that explains the scoring conventions.

As noted previously, ICI is not limited to the scripts presented in FIGS. 5-42 based on the YMRS, the MADRS, or the HAMD scales. Any scales now known or devised in the future may be used, alone or in combination, in the methods and system of the present invention. Many useful scales are described in greater detail in the Handbook of Psychiatric Measures, CD-ROM Plus, American Psychiatry Association (2000) (which is incorporated herein by reference). These scales are referred to herein as the APA group of scales, and include the following: Abnormal Involuntary Movement Scale (AIMS); Addiction Severity Index (ASI); Alcohol Dependence Scale (ADS); Alcohol Expectancy Questionnaire (AEQ); Alcohol Outcomes Module (AOM); Alcohol Timeline Followback (TLFB); Alcohol Use Disorders Identification Test (AUDIT); Alzheimer's Disease Assessment Scale (ADAS); Anger, Irritability, and Assault Questionnaire (AIAQ); Barnes Akathisia Rating Scale (BARS); Barratt Impulsiveness Scale, Version 11 (BIS-11); Behavior and Symptom Identification Scale (BASIS-32); Behavioral and Emotional Rating Scale (BERS); Behavioral Pathology in Alzheimer's Disease Rating Scale (BEHAVE-AD); Body Dysmorphic Disorder Examination (BDDE); Body Shape Questionnaire (BSQ); Brief Psychiatric Rating Scale (BPRS); Brief Sexual Function Inventory (BSFI); Brief Social Phobia Scale (BSPS); Burden Interview (BI); Buss-Durkee Hostility Inventory (BDHI); CAGE Questionnaire; Calgary Depression Scale for Schizophrenia (CDSS); Center for Epidemiologic Studies of Depression Scale (CES-D); Child Dissociative Checklist (CDC); Child Health Questionnaire (CHQ); Children's Global Assessment Scale (CGAS); Clinical Dementia Rating (CDR) Scale; Clinical Global Impressions (CGI) Scale; Clinical Institute Withdrawal Assessment for Alcohol (CIWA-AD); Clinician Administered Rating Scale for Mania (CARS-M); Clinician Alcohol Use Scale (AUS); Clinician Drug Use Scale (DUS); Columbia Impairment Scale (CIS); COMPASS OP; Confusion Assessment Method (CAM); Cornell Scale for Depression in Dementia (CSDD); Crown-Crisp Experiental Index (CCEI) [often referred to as Middlesex Hospital Questionnaire (MHQ)]; Dartmouth COOP Functional Assessment Charts (COOP); Defense Style Questionnaire (DSQ); Depression Outcomes Module (DOM); Diagnostic Interview for Borderline Patients-Revised (DIB-R); Diagnostic Interview for DSM-IV Personality Disorders (DIPD-IV); Dissociative Disorders Interview Schedule (DDIS); Dissociative Experiences Scale (DES); Drug Attitude Inventory (DAI); Epworth Sleepiness Scale (ESS); Excessive Daytime Sleepiness and Nocturnal Sleep Subscales of the Sleep/Wake Activity Inventory (SWAI); Family Assessment Device (FAD); Fear Questionnaire (FQ); Functional Assessment Staging (FAST); Galveston Orientation and Amnesia Test (GOAT); Geriatric Depression Scale (GDS); Global Assessment Scale (GAS); Global Deterioration Scale (GDS); Health of the Nation Outcomes Scales (HoNOS); Impact of Event Scale (IES); Internal State Scale (ISS); Inventory of Depressive Symptomatology (IDS); Lawton Instrumental Activities of Daily Living Scale (Lawton IADL); Life Skills Profile (LSP); Massachusetts General Hospital (MGH) Hairpulling Scale; McGill Pain Questionnaire (MPQ); MEDWatch; Mini-Mental State Examination (MMSE); Mississippi Scale (MSS); Mobility Inventory for Agoraphobia (MI); Multnomah Community Ability Scale (MCAS); Neurobehavioral Cognitive Status Examination (NCSE or COGNISTAT); Obsessive Compulsive Drinking Scale (OCDS); Overt Aggression Scale-Modified (OAS-M); Padua Inventory (PI); Panic Disorder Severity Scale (PDSS); Patient Satisfaction Questionnaire (PSQ); Penn State Worry Questionnaire (PSWQ); Pittsburgh Sleep Quality Index (PSQI); Primary Care Evaluation of Mental Disorders (PRIME-MD); Psychiatric Institute Trichotillomania Scale (PITS); Quality of Life Index (QLI); Quality of Life Interview (QOLI); Quality of Life Scale (QLS); Questionnaire on Eating and Weight Patterns-Revised (QEWP-R); Rating Scale for Extrapyramidal Side Effects (Simpson-Angus EPS Scale); Recent Life Changes Questionnaire (RLCQ); Scale for the Assessment of Negative Symptoms (SANS); Scale for the Assessment of Positive Symptoms (SAPS); Schedule for Affective Disorders and Schizophrenia for School Age-Children: Present and Lifetime Version (K-SADS-PL); Schizophrenia Outcomes Module (SCHIZOM); Screen for Caregiver Burden (SCB); Screener for Somatoform Disorders; Service Satisfaction Scale 30 (SSS-30); Sexual Arousability Inventory (SAI); SF-36 Health Survey (SF-36); Sheehan Disability Scale; Somatoform Disorders Schedule (SDS); Somatoform Disorders Symptom Checklist; South Oaks Gambling Screen (SOGS); Systematic Assessment for Treatment Emergent Events-General Inquiry (SAFTEE-GI); Three-Area Severity of Depression (Raskin) Scale; Treatment Services Review (TSR); TWEAK Test; West Haven-Yale Multidimensional Pain Inventory (WHYMPI); Whitley Index of Hypochondriasis; Wisconsin Quality of Life Index (W-QLI); Yale Global Tic Severity Scale (YGTSS); Yale-Brown Obsessive Compulsive Scale (Y-BOCS); Yale-Brown Obsessive Compulsive Scale Modified for Body Dysmorphic Disorder (BDD-YBOCS); YMRS; and Zung Self-Rating Depression Scale (Zung SDS).

Additional useful scales, referred to herein as the Additional Psychiatry Scales, are the Duke University Severity of Illness ("DUSOI") Scale (Shiels et al., 1997, *Family Practice* 14(6): 466-471); Positive and Negative Syndrome Scale ("PANSS") (Muller et al., 1998, *Schizophrenia Res.* 32: 151-160); DSM-IV Diagnostic Category of Schizoaffective Disorder Scale (Maj et al., 2000, *J. Affective Disorders* 57: 95-98); Perceived Need for Care Questionnaire ("PNCQ") (Meadows et al., 2000, *Soc. Psychiatry Psychiatr. Epidemiol.* 35: 427-435); Brief Psychiatric Rating Scale ("BPRS") (Crippa et al., 2001, *Acta Psychiatrica Scand.* 103: 465-470); Health of Nation Outcome Scales ("HoNOS") (Preston, 2001, *J. Psychiatric and Mental Health Nursing* 8: 405-409); Schedule for Affective Disorders and Schizophrenia, Current symptom version ("SAD-C") (Swann et al., 1999, *Psychiatry Res.* 88: 55-61); Montgomery-Asberg Depression Rating Scale ("MADRS") (Tohen et al., 2001, *J. Affective Disorders* 67: 133-140); Hamilton Anxiety Rating Scale ("HAMA") and Structured Interview ("SIGH-A") (Shear et al., 2001, *Depression and Anxiety* 13: 166-178); and Hamilton Depression Scale ("HAMD") (Williams, 2001, *Eur. Arch. Psychiatry Clin. Neurosci.* 251(Suppl. 2): II6-12).

Additional useful scales, referred to herein as the Geriatric/Cognitive Scales, are the Geriatric Depression Scale ("GDS") (Yeasavage et al., 1983, *J. Psychiatr. Res.* 17: 37-49), Modified Barthel Index ("MBI") (Wade & Collin, 1998, *Int. Disabil. Stud.* 10: 64-67); Folstein Mini Mental Examination ("MMSE") (Folstein et al., 1975, *J. Psychiatr. Res.* 12: 189-198); Executive Clock Drawing ("CLOX") (Royall et al., 1998, *J. Neurology, Neurosurgery & Psychiatry,* 64(5): 588-594); Cambridge Cognitive Exam ("CAMCOG") (Heinik et al., 2000, *Int., J, Geriat. Psychiatryl* 5: 638-643); and Clock Drawing (Shulman, 2000, *Int., J. Geriat. Psychiatry* 15: 548-561).

More useful scales, referred to herein as the Other Cognitive Assessments, are: the AD/HD Rating Scale (Scholte et al., 2001, *J. Child Psychol. Psychiat.* 42: 341-346); Cognitive Capacity Screening ("CCSE") (Meyer et al., 2001, *Int., J. Geriat. Psychiatry* 16: 430-435); Expressed Emotion ("EE") ratings by the Camberwell Family Interview ("CFI") (Mino et al., 2000 *Psychiatry Res.* 94: 221-227); Life Chart Schedule ("LCS") (Susser et al., 2000, *Schizophrenia Res.* 42: 67-77); and Christo Inventory For Substance Misuse Services ("CISS") (Christo et al., 2000, *Drug and Alcohol Dependence* 59: 189-197).

Finally, several useful scales that deal with non-psychiatric measurements, referred herein as the Non-CNS Scales, are: Rheumatoid Arthritis Pain Scale ("RAPS") (Anderson, 2001, *Arthritis Rheum.* 45: 317-323); Arthritis Impact Measurement Scales Health Status Questionnaire ("AIMS" and "AIMS2") (Meenan et al., 1992, *Arthritis Rheum.* 35:1-10); SF-36 Arthritis Specific Health Index ("ASHI") (Ware et al., 1999, *Med. Care* 37(5) Suppl. MS40-MS50); Illness Intrusiveness Ratings Scale ("IIRS") (Devins et al., 2001, *Med. Care* 39: 1097-1104); Work Limitations Questionnaire ("WLQ") (Lerner et al., 2002, *J. Clin. Epidemiology* 55: 197-208); Social Withdrawal Scale (Rigby et al., 1999, *J. Neurological Sciences* 169: 26-34); Rheumatoid Arthritis Severity Scale ("RASS") (Bardwell et al., 2002, *Rheumatology* 41: 38-45); Barthel Index ("BI") and Modified Rankin Scale in acute stroke trials ("MRS") (Sulter et al., 1999, *Stroke* 30: 1538-1541); and Arthritis Impact Measurement Scale ("AIMS2") (Salaffi et al., 2000, *Rheumatology* 39: 720-727).

As one skilled in the art will appreciate, the disclosed invention is susceptible to many variations and alternative implementations without departing from its teachings or spirit. Such modifications are intended to be within the scope of the claims appended below. Each reference cited above is hereby incorporated herein by reference in its entirety.

APPENDIX A1

ICI Scripts for YMRS

I. Mood Elevation:
1a. This past week were any times when even briefly you were feeling optimistic about the future, or just in a really good mood? [Y/N]
1b. What about times when you were feeling very SELF CONFIDENT or especially GOOD about yourself (did you feel optimistic about the future)? [Y/N]
1c. How about the times when someone who was with you would have seen you to be CHEERFUL (would you have felt in a really good mood)? [Y/N]
1d. At those times would people who know you and understood what was happening at the time have thought it was a bit TOO MUCH for the circumstances? [Y/N]
1e. At any time this past week, did you feel EUPHORIC or ON TOP OF THE WORLD? [Y/N]
1f Were the good days this week really TOO GOOD, or just BETTER than the bad days, but not better than normal? [Y/N]
1g. In the past week, were there times when you LAUGHED about things you ordinarily WOULDN'T find funny? [Y/N]
1h. In the past week, did you laugh or JOKE about things that other people didn't find funny (or thought in POOR TASTE)? [Y/N]
1i. Were there times you felt so good you actually started to SING? [Y/N]
II. Energy:
2a. This past week, have you felt particularly FULL OF ENERGY? [Y/N]
2b. HOW OFTEN in the past week did you feel that way (full of energy)? [1=Rarely, 2=Often, 3=Nearly Every Day, 4=Constantly]
2c. Did you feel particularly restless this week (or have trouble sitting still)? [Y/N]
2d. When you felt restless, was it hard to CALM DOWN? [Y/N]
2e. If you had to calm down or sit still, were you ABLE to? [Y/N]
2f. At those times when you couldn't sit still were you CONTINUOUSLY IN MOTION for more than a just a few minutes? [Y/N]
2g. This past week, were you more PHYSICALLY ACTIVE than usual? [Y/N]
2h. This past week, did you find you got a lot MORE DONE than usual? [Y/N]
III. Sexual Interest:
3a. This past week, was sex more interesting to you than usual? [Y/N]
3b. Were you thinking about sex more frequently than usual? [Y/N]
3c. Were you talking or joking about sex more than you normally do? [Y/N]
3d. Were you engaging in sexual activity more than you normally do? [Y/N]
3e. How much more frequently did you engage in sexual activity? 1=Mild Increase, 2=Moderate increase, 3=Extreme Increase
3h. This past week, did you do anything sexual that is unusual for you? [Y/N]
3i. This week, did you talk or joke about sex in situation or environments where it may been inappropriate? [Y/N]
3j. This past week, did you make any sexual advances that may have been inappropriate? [Y/N]
3k. Did you do anything sexual that may have been risky or dangerous this week? [Y/N]
IV. Sleep:
4a. On any night during the past week, were you sleeping LESS than normal? [Y/N]
4b. How much more or less sleep were you getting this week? [More than one hour, Less than one hour]
4c. Did you still feel rested even though you were getting less sleep than usual? [Y/N]
4d. Do you think you could have gotten through the week without sleeping at all? [Y/N]
V. IRRITABILITY:
5a. This past week, were you ANNOYED about things that happened or how people treated you? [Y/N]
5c. This past week, did you do anything which let other people know you were irritable? [Y/N]
5d. This past week, did you get into any ARGUMENTS? [Y/N]
5e. This past week, did you RAISE YOUR VOICE or SHOUT at anyone? [Y/N]
5f. This past week, did anyone complain that you were BEING HOSTILE? [Y/N]
5h. This past week, HOW OFTEN did you find yourself arguing, raising your voice, or being hostile or irritable with people around you? [1=Rarely, 2=Often, 3=Constantly
5i. This past week, did you find it irritating to be QUESTIONED about your symptoms, even by the clinical staff? [Y/N]
5j. Was it so bothersome that you got ANGRY at the person talking to you? [Y/N]
5k. Did you show ANGER or lose your TEMPER at any of your interviews today? [Y/N]
5l. Did your irritability cause you to STOP without completing an interview? [Y/N]
VI. Speech:
6a. This past week, have you been more TALKATIVE than usual? [Y/N]
6b. This past week, have you been speaking more QUICKLY than usual? [Y/N]
6c. Were there times this past week that you SPOKE SO QUICKLY that people had trouble understanding you? [Y/N]

6d. In the last week, did anyone COMPLAIN that they couldn't get a word in? [Y/N]
6e. This past week, did you find it hard to stop talking once you got started? [Y/N]
6g. Were there any times in the past week that your speech was so fast or disorganized that most people would not have been able to follow what you were saying at times, or any times that what you said came out as GIBBERISH? [Y/N]
6h. How FREQUENTLY in the past week have you been more talkative? [1=Rarely, 2=Often, 3=Constantly]
6i. Were there times in the past week that you just KEPT TALKING even though someone was trying to interrupt? [Y/N]
6j. Was it actually IMPOSSIBLE for you to have a conversation this past week? [Y/N]

VII. Language:
7a. This past week, have you had more ideas than usual or any particularly GOOD IDEAS? [Y/N]
7b. Was your thinking especially keen or clear this week? [Y/N]
7c. Were there times this week when you noticed your thoughts seemed overly detailed or UNNECESSARY DETAILS kept coming into your thinking? [Y/N]
7d. This week, did it feel like your thoughts were RACING? [Y/N]
7e. This past week, did you find you were EASILY DISTRACTED? [Y/N]
7f. Did you find it difficult to stay FOCUSED on even simple things like reading an article in the newspaper? [Y/N]
7g. Did you find yourself JUMPING from one topic to another? [Y/N]
7h. Has the flow of your thoughts seemed FASTER than usual this past week? [Y/N]
7i. Were you getting so lost in details or have so many ideas that it was hard to follow? [Y/N]
7j. Were there times your thoughts were so jumbled, that despite your best efforts, it was IMPOSSIBLE TO COMMUNICATE with you? [Y/N]
7k. Did you sometimes have so many ideas that you lost track of what you were saying? [Y/N]

VIII. Content:
8a. Were you more capable or more SELF CONFIDENT than usual this week? [Y/N]
8c. This week, have you taken on any IMPORTANT MISSIONS? [Y/N]
8d. This week, did you find you could UNDERSTAND things more deeply than usual? [Y/N]
8e. Were you more involved with RELIGION this past week? [Y/N]
8f. Did you have any special RELIGIOUS INSIGHTS? [Y/N]
8h. Did you find special significance in THINGS THAT HAPPENED or the way things were arranged around you? [Y/N]
8i. Did you NOTICE things that other people missed this week? [Y/N]
8j. Did you have the sense that people were TALKING ABOUT YOU? [Y/N]
8l. Did your senses play tricks on you, like SEEING THINGS that others couldn't see or HEARING THINGS that others couldn't hear? Did you have any HALLUCINATIONS? [Y/N]
8m. Were there times this week you felt especially smart, attractive, or powerful? Were there times other people thought your behavior was ARROGANT? [Y/N]
8n. Would someone who knew you be CONCERNED about anything you said or did this week? [Y/N]
8q. Did you ACCOMPLISH anything special this week? [Y/N]

IX. Aggressive Behavior:
9a. This past week, have you had any difficulty GETTING ALONG with other people? [Y/N]
9b. Have you been cooperative this past week? [Y/N]
9c. Were there times this week you were LOUD or SARCASTIC? [Y/N]
9d. Have you had any CONFRONTATIONS with people this week? [Y/N]
9e. This week, were there times you were DEMANDING? [Y/N]
9f. This past week did you SHOUT or YELL at anyone? [Y/N]
9g. This week, did you find yourself THROWING things or doing anything DESTRUCTIVE? [Y/N]
9h. Did you PHYSICALLY ASSAULT (hitting, punching, pushing, etc.) anyone this week? [Y/N]
9i. Were there any times this week when you MADE THREATS? [Y/N]
9j. Were there any times this week when you THREATENED the staff or your care providers? [Y/N]

X. Appearance:
10a. Was there anytime you were dressed in a manner someone who knows you would regard as BIZARRE? [Y/N]
10b. Were there occasions when people thought you were OVER-DRESSED or UNDER-DRESSED this past week? [Y/N]
10c. Did you choose DIFFERENT COLORS from usual this week? [Y/N]
10d. Did you wear more JEWELRY or MAKE-UP than usual this week? [Y/N]
10e. Were there times this week that you NEGLECTED your GROOMING? [Y/N]
10g. This past week, did you have any difficulty keeping up your APPEARANCE and GROOMING? [Y/N]
10h. Were there times this week, you HAIR was noticably out of place or your CLOTHING was messy? [Y/N]
10i. Sometimes when grooming is not quite up to par and it makes little difference, was there something about your appearance that really STOOD OUT? [Y/N]
10j. Was this really inappropriate for the circumstances you were in at the time? [Y/N]
10k. Were there times you were clearly DISHEVELED, or appeared in public PARTIALLY CLOTHED or in your underwear? [Y/N]

XI. Insight:
11a. Do you believe that you have a bipolar mood disorder? [Y=yes, P=Possibly, N=No]
11b. As you look back on the week, were there things you did that stand out as UNUSUAL BEHAVIOR for you? [Y/N]
11c. As you look back on the week, did you experience SYMPTOMS of any mental illness?
11e. Is it possible that someone who knew you would think your BEHAVIOR this week was DIFFERENT than usual? [Y/N]
11f. Is it possible that some of this might have happened because of an illness? [Y/N]
11g. Do you feel that you need treatment for bipolar mood disorder? [Y/N]

APPENDIX A2

ICI Scripts for MADRS

I. Apparent Sadness:
1a. If a friend had been with you for the last hour, would there have been any times when they would have known that you were sad or depressed just by looking at you? (Yes/No)
1b. About how much the past hour did your appearance show your were sad or depressed?(Occasionally/Frequently/Constantly)
1c. How sad do you think you appeared? (1=maybe a little, 2=definitely noticeable that I am a little sad or depressed, 3=definitely noticeable that I am a very sad or depressed)
1d. If a friend had been with you for all of the past week, would there have been any times when they would have known that you were sad or depressed just by looking at you? Yes/No
1.e This week were there times you felt so truly miserable that people around you could tell how bad you felt just by looking at you?
(1=Not at all, 2=sometimes but not the last hour, 3=frequently but not the last hour, 4=Frequently, including the last hour)
II. Reported Sadness:
2a. "Have you felt down or depressed at all this week? (Y/N)
2b. "Of the past 7, how many days did you feel this way?" (1-3 days=1, 4-5 days=2, 6-7 days=3)
2c. "On average, how much of the day did you feel this way?" (occasionally=1, much of the day=2, all day=3)
2d. "Can you feel better when pleasant things happen—for example, hearing a good joke or receiving good news?" (never=1, occasionally=2, often=3)
III. Inner Tension:
3a. "Did you feel especially nervous or tense at any point this week?" (Y/N
3b. "How often did you feel this way?" occasionally=1, often=2, almost all the time=3
3c. "Were there times this week when you felt panic or were very afraid?" (Y/N)
3d. "How uncomfortable were these feelings (nervousness, tension or panic) for you?" (slightly=1, somewhat=2, very=3)
3e. "How hard was it for you to control these feelings?" (not hard=1, somewhat hard=2, impossible=3)
IV. Sleep:
4a. "Did you get less sleep than usual this week?" (Y/N)
4b. "Did you have any trouble falling asleep?" (Y/N)
4c. "Was your sleep restless?" (Y/N)
4d. "On a normal night, when you're feeling well, how many hours of sleep do you get?"—3 or less, 4, 5, 6, 7, 8, 9, 10, 11, 12 or more
4e. "This week, on average, how many hours of sleep did you get at night? (Don't include hours during the night when you were actually awake)"—3 or less, 4, 5, 6, 7, 8, 9, 10, 11, 12 or more
Scoring Logic:
(4d-4e)>1 AND (4e<5) return 5
(4d-4e)>1 return 4
(4d-4e)=1 return 3
4D=4e return 2
V. Reduced Appetite:
5a Compared to when you are well, how was your appetite or enjoyment of food this week? (about the same as usual, less than usual, more than usual)
5b. Over the past 7 days, were there any days that you are considerably less or you skipped meals you would usual have eaten? (Y/N)
5c Compared to usual how much has your appetite or enjoyment of food decreased?(Slightly, Moderately, Severely)
5d. How many days in the past week did you eat less or skip one or more meals? (0-1, 2-3, 4-5, 6-7)
5e. Was your interest in food so low that you would not have eaten at all unless someone one actually encouraged you to eat? (Y/N)
VI. Concentration:
6a. "Did you have any difficulty concentrating or collecting your thoughts this week?" (Y/N)
6b. "How often was this a problem for you?" (occasionally=1, sometimes=2, often=3)
6c. "Did this problem interfere with having conversations, or with reading? (Y/N)
6d. "How much did this problem interfere with having conversations, or with reading?" ((just a little=1, a fair amount=2, a great deal=3);
VII. Lassitude:
7a. Compared to usual when you are well, did you have difficulty starting activities this week? (1=Hardly any difficulty, 2=Occasional difficulty, 3=Frequent Difficulty)
7b. Did you feel as though your usual activities required more effort this week? (Y/N)
7c. Did you have difficulty starting even simple activities this week (for example, bathing or getting dressed)? (Y/N)
7d. Did you require help this week to do things you would ordinarily do for yourself? (Y/N)
7e. As you went through your routine activities, how much help did you need this week?
(1=rarely needed help with difficult tasks, 2=often need help with difficult tasks, 3=almost always needed help even with simple tasks)
VIII. Inability to Feel:
8a. Compared to when you are feeling well, how much have you been able to enjoy your daily activities or hobbies this week?
(1. about as much as usual, 2. some decrease but still enjoy most things, 3. decreased for all but a couple activities, 4. unable to enjoy any of the things that usually give me pleasure)
8b. Have you been less interested in doing things or seeing people this week? (Y/N)
8c. Were you less interested than usual in friends, family or acquaintances? (Y/N)
8d. Did you feel entirely numb? (For example, did you find that you could not feel anger or cry?) (Y/N)
8e. Did you have any feelings for friends, family, or acquaintances this week? (Y/N)
8f: Were there really no activities that you enjoyed, even recreation, hobbies, or sex? (Y/N)
IX. PESSIMISM:
9a. This week, were you sometimes pessimistic about the future? (Y/N)
9b. Were there times this week when you felt guilty, or like you'd let people down? (Y/N)
9c. Were there times this week that you felt like a failure, or thought you were worthless? (Y/N)
9d. This week, how often did you have these feelings of pessimism, guilt, or failure? (occasionally=1, often=2, nearly always=3)
9e. Do you feel like you've done something so terrible it can't be fixed, or like you've ruined your life? (Y/N)
9f. If someone told you that your life could be turned around, or your past mistakes corrected, would you believe them? (Y/N)

X. Suicidal Thoughts:

10a. Have you generally been able to enjoy life or were there any times this week when you felt life wasn't worth living or just felt weary of life?
(1=Generally Enjoying life; 2=sometime weary of life, 3=often feel life isn't worth living)

10b. Did you think about suicide at any point this week, even if only briefly? (Y/N)

10c. This week were there any times you found yourself thinking you might be better off dead or about ending your life? (1=Never: 2=sometimes: 3=often)

10d. Were there times this week when you felt you'd really be better off dead?
(1=No; 2=Yes but I have no plan or intent to hurt myself; 3=Yes, have tried to hurt myself or intend to hurt myself if I get the chance)

10f. Have you done anything with the intent to end your life or have you made any plans for suicide this week? Y/N 10g. Do you wish to commit suicide? Y/N 10h. Would you inform your family or care takers if you had urges to hurt yourself? Y/N

APPENDIX A3

ICI SCRIPTS for HAMD

I. Depressed Mood:
a. Have you been feeling down, depressed, sad or blue this week? [Y/N]
b. Have you been feeling hopeless, helpless or worthless this week? [Y/N]
c. How intense were these feelings this week? [mild=0, moderate=1, severe=2, extremely severe=3]
d. How often did you have these feelings this week? [occasionally=0, much of the time=1, almost all the time=2]

II. Guilt:
2a. Have you been especially critical of yourself this week, feeling like you did things wrong or let others down? [Y/N]
2b. Have you been feeling guilty about anything you've done or not done? [Y/N]
2c. Have you thought that you brought this depression (or this situation) on yourself in some way, or that you're being punished? [Y/N]
2d. Have you heard voices or seen visions that said you were guilty, or threatened you? [Y/N]
2e. Did you have these feelings because you were ill, and not able to do the things you usually do? [Y/N]
2f. This week, how often did you feel critical of yourself, ashamed, or guilty? [occasionally=0, much of the time=1, almost all the time=2]

III. Suicide:
3a. This past week have you had thoughts that life is not worth living? [Y/N]
3b. Have you wished you were dead, or thought about your death? [Y/N]
3c. Have you thought about hurting or killing yourself? [Y/N]
3d. Did you do anything to harm yourself intentionally this week? [Y/N]
3e. How likely is it that you'll do something to hurt yourself before your next visit with your psychiatrist? [very unlikely, possible, somewhat unlikely, very likely]

IV. Early Insomnia:
4a. Have you had any trouble this week falling asleep at the beginning of the night? [Y/N]
4b. How long has it been taking you to fall asleep? [less than 30 minutes=0, 30-60 minutes=1, more than 1 hour=2]
4c. How many nights did you have trouble falling asleep? [1-2=0, 3-5=1, 6 or more=2]

V. Middle Insomnia:
5a. During the past week, have you been waking up in the middle of the night? [Y/N]
5b. Was this only to go to the bathroom? [Y/N]
5c. How long did it take you to fall back to sleep? [less than an hour=0, an hour or more=1]
5d. How many nights did you have this problem? [1 or 2=0, 3-5=1, 6 or more=2]

VI. Late Insomnia:
6a. Are you waking up in the morning, unintentionally, earlier than usual? [Y/N];
6b. How much earlier than usual did you wake up? [less than 30 minutes=0, 30-59 minutes=1, an hour or more=2]
6c. How often did you have this problem? [1 or 2 days=0, 3-5 days=1, 6 or more days=2]

VII. Work and Activities:
7a. This week, were you able to enjoy activities such as work, hobbies, and time spent with family or friends as much as you usually do? [Y/N]
7b. This week, did you have to push yourself to complete work or participate in outside activities such as hobbies that you usually enjoy? [Y/N]
7c. Were there any activities that you stopped doing this week? [Y/N]
7d. Did you have to stop working this week, or give up all of your activities, because you felt you were unable to do them? [Y/N]
7e. How often this week did you enjoy activities less, or take less interest in them than usual? [occasionally=0, sometimes=1, nearly always=2]

VIII. Retardation:
8a. Did you feel your thinking, speaking or movement was slowed down this week? [Y/N]
8b. Did anyone else notice that your thinking, speaking, or movement was slowed down this week? [Y/N]
8c. How much slower were you thinking, moving, or speaking? [just a little=0, somewhat=1, very much=2]

XI. Agitation:
9a. Did you fidget more than usual this week, or did others notice you were fidgeting? [Y/N]
9b. Did you feel very restless or agitated? [Y/N]
9c. Was it difficult to sit still, even briefly? [Y/N]

X. Anxiety (Psychological):
10a. This week, how often did you feel unusually tense, anxious or worried? [never=0, occasionally=1, much of the time=2, almost all the time=3]
10b. How much did these feelings interfere with your ability to do the things you ordinarily do during the week? [not at all=0, a little=1, a lot=2, completely=3]
10c. Did these feelings prevent you from working, or doing basic tasks at home? [Y/N]

XI. Anxiety (Somatic):
11a. Over the past week, have you had any of the following symptoms: dry mouth, gas, indigestion, diarrhea, cramps, belching? [Y/N]
11b. Over the past week, have you had any of the following symptoms: heart palpitations, headaches, hyperventilating (breathing fast), sighing, having to urinate frequently, sweating? [Y/N]
11c. How often did you have these symptoms this week? [occasionally (fewer than 3 days)=0, much of the time (3-5 days)=1, almost all the time (6-7 days)=2]
11d. How severe were they? [a little=0, somewhat=1, severe=2, very severe=3]
11e. How much did they interfere with your ability to function? [not at all=0, a little=1, somewhat=2, a great deal=3]

XII. Appetite:
12a. Did you have less appetite than usual this week, or no appetite at all? [Y/N]
12b. Did other people have to urge you to eat? [Y/N]
12c. Did you have to force yourself to eat? [Y/N]
12d. How often was your appetite decreased? [occasionally (fewer than 3 days)=0, much of the time (3-5 days)=1, almost all the time (6-7 days)=2]
XIII. Somatic Symptoms:
13a. Was your energy level decreased this week? [Y/N]
13b. Did you feel fatigued this week? [Y/N]
13c. Did you have backaches, headaches or muscle aches this week? [Y/N]
13d. Did you feel any heaviness in your arms, legs, back or head this week? [Y/N]
XIV. Sexual Interest:
14a. How has your interest in sex been this week? [normal=0, mildly decreased=1, greatly decreased=2]
14b. If the "person of your dreams" knocked on your door, do you think your interest in sex would still be decreased? [Y/N]
XV. Hypochondriosis:
15a. In the past week, have you been more concerned than usual about your physical health or how your body is working? [Y/N]
15b. How often did you think about your physical health? [occasionally [fewer than 3 days)=0, much of the time (3-5 days)=1, almost constantly (6-7 days)=2]
15c. Are you concerned that you might have a serious undiagnosed physical illness? [Y/N]
15d. If your doctor examined you and told you that you were healthy, would that reassure you? [Y/N]
15e. Do you believe something extremely severe or unusual is affecting your body? [Y/N]
XVI. Weight loss:
16a. Have you lost any weight this week? [Y/N/Not sure]
16b. Have you been trying to lose weight this week? [Y/N]
16c. Do your clothes feel any looser this week? [Y/N]
16d. Did you lose a pound (half a kilogram) or more this week? [Y/N]
XVII. Insight:
17a. Do you think you are suffering from depression, or were recently suffering from depression? [Y/N/Possibly}

What is claimed is:

1. A method for recertifying or monitoring performance of a clinical rater participating in a clinical trial comprising:
   receiving one or more rater inputs reflecting the rater's clinical evaluation of a severity of a previously diagnosed condition in a subject;
   performing a computerized assessment of the subject to quantify severity of the previously diagnosed condition in the subject through a computerized interview that comprises:
      presenting a first question to the subject and receiving a first input from the subject in response thereto;
      based on the first input, selecting a second question from a plurality of questions;
      presenting the selected second question to the subject and receiving a second input from the subject in response thereto; and
      based on one or more inputs received from the subject, determining in accordance with a clinical rating scale a computerized severity score for the previously diagnosed condition in the subject; and
   determining, via a processor, whether the one or more rater inputs are in accordance with the computerized severity score.

2. The method according to claim 1, wherein the previously diagnosed condition is a psychiatric illness.

3. The method according to claim 1, wherein the clinical rating scale is in accordance with one of the following scales: the Young Mania Rating Scale (YMRS); the Montgomery-Asberg Depression Rating Scale (MADRS); the Hamilton Depression Scale (HAMD); the Schedule for Affective Disorders and Schizophrenia, Current symptom version mania Rating Scale (SADS-C); an Additional Psychiatry Scale; a Geriatric/Cognitive Scale; an Other Cognitive Assessment; a Non-CNS Scale; or a member of the APA group of scales.

4. The method according to claim 1, wherein at least one unselected question is not presented to the subject.

5. The method according to claim 1, further comprising:
   based on the second input, selecting a third question from the plurality of questions; and
   presenting the selected third question to the subject and receiving a third input from the subject in response thereto.

6. The method according to claim 5, wherein selection of the third question is based on a plurality of inputs by the subject.

7. The method according to claim 1, wherein the questions are presented by visual, audio, or multimedia display.

8. The method according to claim 1, wherein the inputs are received directly from the subject by means of a keyboard, a pointing device, a touch-screen device, or voice response.

9. The method according to claim 1, wherein the computerized assessment is performed within 24 hours after a clinical interview at which the clinical evaluation is made.

10. The method according to claim 1, wherein the clinical interview and computerized assessment are performed during the same clinic visit.

11. The method according to claim 1, wherein the step of receiving comprises receiving a plurality of rater inputs reflecting a given rater's clinical evaluation of severity of the previously diagnosed condition in a plurality of subjects at a plurality of clinical interviews; and
   wherein the step of determining comprises determining whether the plurality of rater inputs are in accordance with computerized severity scores for the previously diagnosed condition in the subjects.

12. The method according to claim 1, wherein the step of receiving comprises receiving a plurality of rater inputs reflecting a given rater's clinical evaluation of severity of a previously diagnosed condition in a single subject at a plurality of clinical interviews of that subject; and
   wherein the step of determining comprises determining whether the plurality of rater inputs are in accordance with a plurality of computerized severity scores for the previously diagnosed condition in that subject determined in conjunction with the plurality of clinical interviews.

13. A method for improving performance of a clinical rater participating or being trained to participate in a clinical trial, comprising:
   receiving one or more rater inputs reflecting the clinical rater's clinical evaluation of a severity of a previously diagnosed condition in a subject;
   performing a computerized assessment of the subject to quantify severity of the previously diagnosed condition in the subject through a computerized interview that comprises:
      presenting a first question to the subject and receiving a first input from the subject in response thereto;
      based on the first input, selecting a second question from a plurality of questions;

presenting the selected second question to the subject and receiving a second input from the subject in response thereto; and based on one or more inputs received from the subject, determining in accordance with a clinical rating scale a computerized severity score for the previously diagnosed condition in the subject;

determining, via a processor, whether the one or more rater inputs are in accordance with the computerized severity score; and if the one or more rater inputs substantially differs from the computerized severity score, providing an indication that the clinical rater is in need of remedial training or providing remedial training to the clinical rater.

14. The method of claim 13, wherein the remedial training includes one or more of the following: providing explanatory material concerning how to evaluate the severity of the previously diagnosed condition, presenting a remedial script, and presenting a remedial semi-scripted interview to the clinical rater.

15. A computing device comprising:
a processing unit; and
a memory having computer executable instructions stored thereon that when executed by the processor cause the processor to perform the following steps:
receive one or more rater inputs reflecting the clinical rater's clinical evaluation of a severity of a previously diagnosed condition in a subject;
perform a computerized assessment of the subject to quantify severity of the previously diagnosed condition in the subject through a computerized interview that comprises:
presenting a first question to the subject and receiving a first input from the subject in response thereto;
based on the first input, selecting a second question from a plurality of questions;
presenting the selected second question to the subject and receiving a second input from the subject in response thereto; and
based on one or more inputs received from the subject, determining in accordance with a clinical rating scale a computerized severity score for the previously diagnosed condition in the subject;
determine, via a processor, whether the one or more rater inputs are in accordance with the computerized severity score; and
if the one or more rater inputs substantially differs from the computerized severity score, provide an indication that the clinical rater is in need of remedial training or providing remedial training to the clinical rater.

16. A computer readable medium wherein the computer readable medium is not a transient signal having stored thereon instructions that, when executed by a processor, cause the processor to perform the following steps:
receive one or more rater inputs reflecting the clinical rater's clinical evaluation of a severity of a previously diagnosed condition in a subject;
perform a computerized assessment of the subject to quantify severity of the previously diagnosed condition in the subject through a computerized interview that comprises:
presenting a first question to the subject and receiving a first input from the subject in response thereto;
based on the first input, selecting a second question from a plurality of questions;
presenting the selected second question to the subject and receiving a second input from the subject in response thereto; and
based on one or more inputs received from the subject, determining in accordance with a clinical rating scale a computerized severity score for the previously diagnosed condition in the subject;
determine, via a processor, whether the one or more rater inputs are in accordance with the computerized severity score; and
if the one or more rater inputs substantially differs from the computerized severity score, provide an indication that the clinical rater is in need of remedial training or providing remedial training to the clinical rater.

17. A system comprising:
an output device configured to present selected questions to a subject;
an input device configured to accept inputs from the subject; and
one or more computing devices configured to:
present, via the output device, a first question to the subject;
receive, via the input device, a first input from the subject in response to the first question;
based on the first input, select a second question from a plurality of questions;
present, via the output device, the selected second question to the subject;
receive, via the input device, a second input from the subject in response to the second question; and
determine a computerized severity score, based on the inputs received from the subject in accordance with a rating scale, wherein the computerized severity score quantifies a severity of a previously diagnosed condition in the subject.

18. A computerized method for assisting or training a rater for clinical trials to evaluate severity of symptoms in a subject participating in a clinical trial and having a previously diagnosed medical condition, comprising:
presenting a first output to the rater, wherein the first output to the rater conveys a first suggestion concerning a question to be posed to the subject or a clinical observation to be made concerning the subject;
receiving a first input from the rater in response to the first output;
based on the first input that was received in response to the first output, selecting, processor, a second output from a plurality of alternative second outputs, wherein the second output concerns a question to be posed to the subject by the rater in an interview for the clinical trial or a clinical observation to be made by the rater concerning the subject in the interview for the clinical trial; and
presenting the second output to the rater.

19. The method according to claim 18, further comprising:
based on the first input and the second input received from the rater, determining in accordance with a clinical rating scale a computerized severity score for the medical condition.

20. The method according to claim 18, wherein the rater is a health care provider evaluating the severity of symptoms in a patient or evaluating a response of a patient to treatment or placebo.

21. A computing device configured to assist or train a rater for clinical trials to evaluate severity of symptoms in a subject participating in a clinical trial and having a previously diagnosed medical condition, the computing device comprising:
 a processing unit; and
 a memory having computer executable instructions stored thereon that when executed by the processor cause the processor to perform the following steps:
  present a first output to the rater, wherein the first output to the rater conveys a first suggestion concerning a question to be posed to the subject or a clinical observation to be made concerning the subject;
  receive a first input from the rater in response to the first output;
  based on the first input that was received in response to the first output, select, via a processor, a second output from a plurality of alternative second outputs, wherein the second output concerns a question to be posed to the subject by the rater in an interview for the clinical trial or a clinical observation to be made by the rater concerning the subject in the interview for the clinical trial; and
  present the second output to the rater.

22. A computer readable medium wherein the computer readable medium is not a transient signal configured to assist or train a rater for clinical trials to evaluate severity of symptoms in a subject participating in a clinical trial and having a previously diagnosed medical condition, the computer readable medium having stored thereon instructions that, when executed by a processor, cause the processor to perform the following steps
 present a first output to the rater conveying a first suggestion concerning a question to be posed to the subject or a clinical observation to be made concerning the subject;
 receive a first input from the rater in response to the first output; and
 based on the first input that was received in response to the first output, select a second output from a plurality of alternative second outputs concerning a question to be posed to the subject by the rater in an interview for the clinical trial or a clinical observation to be made by the rater concerning the subject in the interview for the clinical trial; and
 present the second output to the rater.

23. A system configured to assist or train a rater for clinical trials to evaluate a severity of symptoms in a subject participating in a clinical trial and having a previously diagnosed medical condition, the system comprising:
 an output device configured to present outputs to the rater;
 an input device configured to accept inputs from the rater; and
 one or more computers configured to perform the following steps:
  present, via the output device, a first output to the rater conveying a first suggestion concerning a question to be posed to the subject or a clinical observation to be made concerning the subject;
  receive, via the input device, a first input from the rater in response to the first output; and
  based on the first input that was received in response to the first output, select a second output from a plurality of alternative second outputs concerning a question to be posed to the subject by the rater in an interview for the clinical trial or a clinical observation to be made by the rater concerning the subject in the interview for the clinical trial; and
  present the second output to the rater.

24. A computerized method for implementing a clinical rating scale to evaluate a previously diagnosed condition in a subject presented with a series of questions to determine whether to include the subject in a clinical trial, the method comprising:
 establishing a bank of questions directed to measurement of an item in the clinical rating scale;
 presenting to the subject a first question selected from the bank of questions and receiving a first input from the subject in response to the first question;
 presenting to the subject a second question selected from the bank of questions based on the first input and receiving a second input from the subject in response to the second question; and
 based on the received first input and the received second input:
  generating, via a processor, a score for the item in the clinical rating scale, wherein a given response to at least one question results in different scores for the item dependent on the place of the at least one question within the series of questions; and
  determining whether to include or exclude the subject in the clinical trial.

25. The method of claim 24, wherein each input to a question results either in generating a score for the item in the clinical rating scale or in selection of another question from the bank of questions.

26. The method of claim 24, wherein the step of establishing comprises establishing a plurality of banks of questions, each bank directed to measurement of a distinct item in the clinical rating scale; and
 the step of generating comprises generating scores for a plurality of items in the clinical rating scale.

27. The method according to claim 24, further comprising the step of:
 determining whether at least one input to a question is an acceptable input and presenting the question to the subject again if the at least one input is not acceptable.

28. The method according to claim 24, wherein the series of questions includes a multiple choice question such that the subject selects from a list of inputs for responding to the multiple choice question.

29. The method according to claim 28, wherein two or more inputs in the list of inputs result in a common question being presented to the subject.

30. The method according to claim 24, further comprising:
 automatically determining by previously established criteria whether or not the subject qualifies for inclusion in the clinical trial.

31. A computer readable medium wherein the computer readable medium is not a transient signal having stored thereon instructions that, when executed by a processor, cause the processor to perform the following steps:
 establish a bank of questions directed to measurement of an item in the clinical rating scale;
 present to the subject a first question selected from the bank of questions and receiving a first input from the subject in response to the first question;
 present to the subject a second question selected from the bank of questions based on the first input and receiving a second input from the subject in response to the second question; and
 based on the received first input and the received second input:
  generate a score for the item in the clinical rating scale, wherein a given response to at least one question results in different scores for the item dependent on the place of the at least one question within the series of questions; and determine whether to include or exclude the subject from a clinical trial.

32. A computing device comprising:

a processing unit; and a memory having computer executable instructions stored thereon that when executed by the processor cause the processor to perform the following steps:

establish a bank of questions directed to measurement of an item in the clinical rating scale;

present to the subject a first question selected from the bank of questions and receiving a first input from the subject in response to the first question;

present to the subject a second question selected from the bank of questions based on the first input and receiving a second input from the subject in response to the second question; and based on the received first input and the received second input:

generate a score for the item in the clinical rating scale, wherein a given response to at least one question results in different scores for the item dependent on the place of the at least one question within the series of questions; and determine whether to include or exclude the subject from a clinical trial.

\* \* \* \* \*